US010086043B2

(12) United States Patent
Chien et al.

(10) Patent No.: US 10,086,043 B2
(45) Date of Patent: Oct. 2, 2018

(54) EFFICIENT PROTEIN EXPRESSION IN VIVO USING MODIFIED RNA (MOD-RNA)

(75) Inventors: Kenneth R. Chien, Cambridge, MA (US); Leon M. Ptaszek, Newton, MA (US); Oi-Lan Lui, Boston, MA (US); Lior Zangi, Brookline, MA (US); Wataru Ebina, Boston, MA (US); Derrick J. Rossi, Roslindale, MA (US)

(73) Assignees: THE GENERAL HOSPITAL CORPORATION, Boston, MA (US); CHILDREN'S MEDICAL CENTER CORPORATION, Boston, MA (US)

(*) Notice: Subject to any disclaimer, the term of this patent is extended or adjusted under 35 U.S.C. 154(b) by 0 days.

(21) Appl. No.: 14/009,351

(22) PCT Filed: Mar. 12, 2012

(86) PCT No.: PCT/US2012/028802
§ 371 (c)(1),
(2), (4) Date: Nov. 26, 2013

(87) PCT Pub. No.: WO2012/138453
PCT Pub. Date: Oct. 11, 2012

(65) Prior Publication Data
US 2014/0073687 A1 Mar. 13, 2014

Related U.S. Application Data

(60) Provisional application No. 61/471,166, filed on Apr. 3, 2011, provisional application No. 61/471,584, filed on Apr. 4, 2011.

(51) Int. Cl.
| A61K 38/18 | (2006.01) |
| A01K 67/027 | (2006.01) |
| A61K 48/00 | (2006.01) |
| C12N 15/11 | (2006.01) |
| A61K 31/7115 | (2006.01) |
| A61K 31/4745 | (2006.01) |
| A61K 31/513 | (2006.01) |
| A61K 31/517 | (2006.01) |
| A61K 31/519 | (2006.01) |
| A61K 31/555 | (2006.01) |
| A61K 31/7068 | (2006.01) |
| A61K 33/24 | (2006.01) |
| A61L 31/10 | (2006.01) |
| A61L 31/16 | (2006.01) |

(52) U.S. Cl.
CPC ...... *A61K 38/1866* (2013.01); *A01K 67/0276* (2013.01); *A61K 31/4745* (2013.01); *A61K 31/513* (2013.01); *A61K 31/517* (2013.01); *A61K 31/519* (2013.01); *A61K 31/555* (2013.01); *A61K 31/7068* (2013.01); *A61K 31/7115* (2013.01); *A61K 33/24* (2013.01); *A61K 48/005* (2013.01); *A61L 31/10* (2013.01); *A61L 31/16* (2013.01); *C12N 15/111* (2013.01); *A01K 2207/05* (2013.01); *A01K 2217/075* (2013.01); *A01K 2227/105* (2013.01); *A01K 2267/03* (2013.01); *A01K 2267/0393* (2013.01); *A61L 2300/258* (2013.01); *C12N 2310/11* (2013.01); *C12N 2310/14* (2013.01); *C12N 2800/30* (2013.01)

(58) Field of Classification Search
CPC .............. A61K 31/7115; A61K 48/005; A61K 38/1866; A61K 2300/00; A61K 31/4745; A61K 31/513; A61K 31/517; A61K 31/519; A61K 31/555; A61K 31/7068; A61K 33/24; A61K 2207/05; A01K 67/0276; A01K 2217/075; A01K 2227/105; A01K 2267/03; C12P 21/00; C12N 15/87; C12N 15/63; C12N 15/111; C12N 15/11
USPC ....................................................... 514/44 R
See application file for complete search history.

(56) References Cited

U.S. PATENT DOCUMENTS

| 7,709,450 B2 * | 5/2010 | Eriksson ................ C12N 15/86 514/44 R |
| 2006/0188490 A1 * | 8/2006 | Hoerr et al. .............. 424/93.21 |
| 2008/0076174 A1 | 3/2008 | Selden et al. |
| 2009/0286852 A1 | 11/2009 | Kariko et al. |
| 2010/0047261 A1 | 2/2010 | Hoerr et al. |
| 2012/0251618 A1 | 10/2012 | Schrum et al. |
| 2012/0322864 A1 | 12/2012 | Rossi et al. |
| 2012/0322865 A1 | 12/2012 | Rossi et al. |
| 2015/0291678 A1 | 10/2015 | Rudolph et al. |

FOREIGN PATENT DOCUMENTS

| CA | 2769670 A1 | 2/2011 |
| EA | 013375 | 4/2010 |
| JP | 2002-508299 A | 3/2002 |
| JP | 2010-508014 A | 3/2010 |

(Continued)

OTHER PUBLICATIONS

Heilmann et al., 2003, Eur. J. Cardio-thoracic Surgery 24:785-793.*
Yau et al 2004, Surgery of Acquired Cardiovascular disease 127:1180-1187.*
Jemielity et al 2003, RNA 9:1108-1122.*
Ge et al 2010, RNA 16:118-130.*
Serpi et al 2011, Cardiovascular Research 89:204-213.*
Zangi et al., Nature Biotechnology, published online Sep. 8, 2013. "Modified mRNA directs the fate of heart progenitor cells and induces vascular regeneration after myocardial infarction".

(Continued)

*Primary Examiner* — Christopher M Babic
*Assistant Examiner* — Kimberly A Aron
(74) *Attorney, Agent, or Firm* — Nixon Peabody LLP

(57) ABSTRACT

Aspects of the invention described herein relate to synthetic, modified RNAs and their use in vivo to modulate gene expression. Aspects of the invention further relate to the use of these synthetic, modified RNAs in myocytes, cardiomyoctes, and tumors.

5 Claims, 35 Drawing Sheets

Specification includes a Sequence Listing.

(56) References Cited

FOREIGN PATENT DOCUMENTS

| WO | 99/14346 A2 | 3/1999 |
| WO | 2004/065600 | 8/2004 |
| WO | 2008/052770 A2 | 5/2008 |
| WO | 2009127230 A1 | 10/2009 |
| WO | 2010144678 A2 | 12/2010 |
| WO | 2011/012316 A2 | 2/2011 |
| WO | 2011/012316 A3 | 2/2011 |
| WO | 2011/130624 A2 | 10/2011 |
| WO | 2011130624 | 10/2011 |
| WO | 2012/135805 A2 | 10/2012 |
| WO | 2012135805 | 10/2012 |
| WO | 2007024708 A2 | 3/2013 |

OTHER PUBLICATIONS

Lui et al., Cell Research, 1-15 (2013). "Driving vascular endothelial cell fate of human multipotent Isl1+ heart progenitors with VEGF modified mRNA".

U.S. Appl. No. 61/470,451, filed Mar. 31, 2011.

U.S. Appl. No. 61/387,220, filed Sep. 28, 2010.

U.S. Appl. No. 61/325,003, filed Apr. 16, 2010.

Ausoni et al., J Cell Biol, 184(3):357-364 (2009). "From fish to amphibians to mammals: in search of novel strategies optimize cardiac regeneration." Retrieved from the Internet, URL: http://jcb.rupress.org/content/184/3/357.full.pdf.

Chen et al., Genes Dev, 16:2743-2748 (2002). "Inhibition of hedgehog signaling by direct binding of cyclopamine to smoothened." Retrieved from the Internet on May 22, 2012, URL: http://genesdev.cshlp.org/content/16/21/2743.full.

Ferrara et al., Annu Rev Med, 58:491-504 (2007). "Targeting VEGF-A to treat cancer and age-related macular degeneration."

Ma et al., Developmental Biology, 323:98-104 (2008). "Reassessment of Is11 and Nkx2-5 cardiac fate maps using a Gata4-based reporter of Cre activity."

mRNA UTR Structure Exon Intron Cap. Molecular Biology Photo Gallery [online], retrieved from the Internet on Dec. 16, 2007, URL: http://www.molecularstation.com/molecular-biology-images/503-rna-pictures/66-mrna-utr-exo-intron-cap.html.

Thum et al., Nature, 456(18/25):980-986 (2008). "MicroRNA-21 contributes to myocardial disease by stimulating MAP kinase signalling in fibroblasts."

European Search Report; dated Oct. 16, 2014; Related to EP Application No. 12767300.2.

Tavernier et al., "mRNA as gene therapeutic: How to control protein expression", Journal of Controlled Release 150(3):238-247 (2010).

Bechler, "Influence of Capping and Polyadenylation on mRNA Expression and on Antisense RNA Mediated Inhibition of Gene Expression", Biochemical and Biophysical Research Communications 241:193-199 (1997).

Ito, "ISIS 301012 Gene Therapy for Hypercholesterolemia: Sense, Antisense, or Nonsense?", Annals of Pharmacotherapy 41:1669-1678 (2007).

Kormann et al., "Expression of therapeutic proteins after delivery of chemically modified mRNA in mice", Nature Biotechnology 29(2):154-157 (2011).

Li et al., "Overcoming obstacles to develop effective and safe siRNA therapeutics", Expert Opinion on Biological Therapy 9(5):609-619 (2009).

Losordo et al., "Gene Therapy for Myocardial Angiogenesis: Initial Clinical Results With Direct Myocardial Injection of phVEGF165 as Sole Therapy for Myocardial Ischemia", Circulation 98:2800-2804 (1998).

Nagata et al., "Molecular cloning and expression of cDNA for human granulocyte colony-stimulating factor", Nature 319:415-418 (1986).

Nagata et al., "The chromosomal gene structure and two mRNAs for human granulocyte colony-stimulating factor", The EMBO Journal 5(3):575-581 (1986).

Segura et al., "Monitoring Gene Therapy by External Imaging of mRNA: Pilot Study on Murine Erythropoietin", Therapeutic Drug Monitoring 29:612-618 (2007).

Tsuchiya et al. "Isolation and characterization of the cDNA for murine granulocyte colony-stimulating factor", PNAS 33:7633-7637 (1986).

Shintani et al., "Angiogenic Cytokine: VEGF", The Journal of Japanese College of Angiology 46:289-295 (2006) (full Japanese Article with English translation).

* cited by examiner

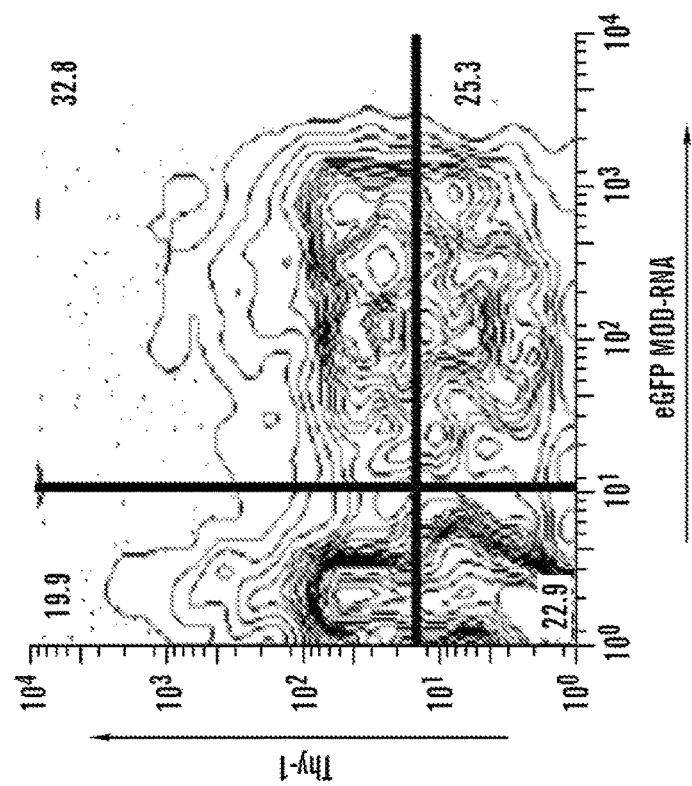
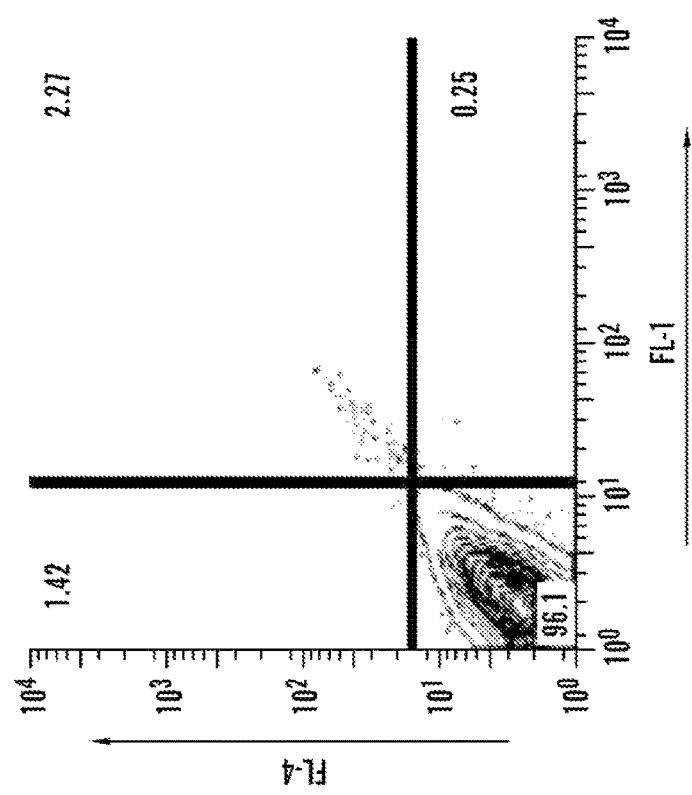
FIG. 1B
FIG. 1A

EFFICIENT PROTEIN EXPRESSION IN VIVO USING MODIFIED RNA (MOD-RNA)

CROSS REFERENCE TO RELATED APPLICATIONS

This application is a 35 U.S.C. § 371 National Phase Entry Application of International Application No. PCT/US2012/028802 filed Mar. 12, 2012, which designates the U.S., and which claims the benefit under 35 U.S.C. § 119(e) of U.S. Provisional Patent Application Ser. No. 61/471,166 filed Apr. 3, 2011 and U.S. Provisional Patent Application No. 61/471,584 filed Apr. 4, 2011, the contents of each of which are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Oct. 1, 2013, is named 030258-070154 SL.txt and is 2,105,672 bytes in size.

FIELD OF THE INVENTION

The present invention relates generally to gene expression in myocytes and cardiomyocytes in vivo using synthetic, modified RNAs, and uses thereof. The present invention further relates generally to modulation of gene expression in tumors using synthetic, modified RNAs and the uses thereof.

BACKGROUND

Cardiovascular disease involves diseases or disorders associated with the cardiovascular system. Such disease and disorders include those of the pericardium, heart valves, myocardium, blood vessels, and veins.

Over the last two decades, the morbidity and mortality of heart failure has markedly increased (Tavazzi, 1998). Therefore, finding an effective therapeutic method is one of the greatest challenges in public health for this century. Although there are several alternative ways for treatment of heart failure, such as coronary artery bypass grafting and whole-heart transplantation, myocardial fibrosis and organ shortage, along with strict eligibility criteria, mandate the search for new approaches to treat the disease. Cell transplantation has also emerged to be able to increase the number of contractile myocytes in damaged hearts. However, cardiomyocytes, which are also known as cardiac muscle cells, are terminally differentiated cells and are unable to divide and their use in cell transplantation is limited by the inability to obtains sufficient quantities of cardiomyocytes for the repair of large areas of infarct myocardium.

Thus, one strategy would be induce gene expression or express proteins in the heart, e.g., in cardiomyocytes after injury to protect the cells from cell death, or as preventative strategies such as introducing agents or genes into cells to increase their resistance to mechanical and/or hypoxia induced stress. Traditional methods for introducing agents or inducing gene expression has been from exogenous DNA, or from recombinant viral vectors, however, the use of such gene therapy methods have potential risks of introducing unintended mutagenic genome changes as well as being potentially toxic to cells and/or elicits an innate immune response. Additionally, protein replacement therapy may also be difficult due to issues with the in vivo delivery of proteins inducing innate immune responses as well as problems with protein stability and/or delivery to particular tissue and cell types. Accordingly, there exists a need for efficient method for in vivo gene expression and/or protein expression for beneficial research and/or therapeutic applications.

SUMMARY OF THE INVENTION

Provided herein is a method for in vivo gene expression using synthetic modified RNA sequence, and in particular for in vivo protein expression in tissues and organs, and also in cell in vivo, e.g., muscle cells including but not limited to cardiomyocytes and myogenic cells. Other aspects of the present invention relate to use of modified-RNAs encoding a protein of interest for treatment of diseases and disorders, for example, but not limited to muscle disorders and cardiovascular diseases and disorders in a subject. Other aspects of the present invention relate to pharmaceutical compositions and kits thereof comprising a least one synthetic modified-RNA encoding a protein of interest for administration to a subject for treatment of diseases or disorders in a subject. In some embodiments, the disease or disorder is a cardiovascular disease or disorder, and the protein of interest expressed by a synthetic modified-RNA is a cardiac function enhancing protein.

Recently, it has been reported that synthetic, modified RNA (herein referred to as "MOD-RNA") can be used for overexpression of a gene of interest in mammalian cells in vitro. The chemical and sequence modifications made in the synthetic mRNA stabilize the molecule and enhance transcription. Expression of polypeptides from MOD-RNA allows for highly efficient, transient expression of a gene of interest in vitro without requiring introduction of DNA or viral sequences that may be integrated into the host cell.

Herein, the inventors demonstrate efficient protein expression in vivo using synthetic, modified RNAs. As demonstrated herein, use of MOD-RNAs to express a protein in vivo occurs rapidly, and is much more efficient and less toxic to cells than introducing non-MOD RNAs (e.g., normal RNA sequences), or direct intracellular introduction of proteins, which can activate the innate immune system. Demonstrated herein is delivery of synthetic modified RNAs using tailored transfection techniques, and in some embodiments, administration of MOD-RNAs in a composition can also comprise specific reagents that inhibit degradation of an introduced, synthetic modified RNA.

One aspect of the present invention relates to compositions, methods and kits for protein expression in vivo by introducing synthetic modified RNA encoding a protein of interest into a tissue. As disclosed herein, in some embodiments the method for introducing at least one in vivo synthetic modified RNA as described here includes several unique features, including a specific transfection protocol, e.g., delivery of MOD-RNA encoding a protein of interest at a high concentration level, e.g., at least about 1 µg/µl or about 100 µg/µl, as well as tissue-specific operative techniques to allow for specific introduction of a composition comprising a modified RNA into an organ and/or tissue of interest.

In some embodiments, the methods, composition and kits as disclosed herein can be tailored for use in methods for protein replacement therapy in vivo. In some embodiments, a synthetic modified RNA encoding a protein of interest can be delivered to a tissue and/or organ for in vivo protein expression in a method for treatment of a variety of different diseases where protein expression is desirable. In some embodiments, a disease can be a loss-of-function disease as disclosed herein, e.g., without limitation muscular dystrophy, cystic fibrosis and other diseases where the level of protein expression of a particular protein is inadequate and/or gene expression results in a non-functional protein.

Additionally, in some embodiments a method for in vivo delivery of synthetic modified RNA technology for in vivo protein expression as disclosed herein can be used to create an animal model platform which can be used to study whole-organ and systemic pathophysiology. In some embodiments, the methods as disclosed herein provide an in vivo system, using both small- and large-animal models, such as primates and porcine models, for testing and/or the development of therapeutics for clinical use in human patients.

In some embodiments, the methods and compositions and kits as disclosed herein for in vivo protein expression using synthetic modified RNAs can be for the development and treatment of a disease or disorder. In some embodiments, a disease or disorder is a genetic and/or acquired disorder that is the result of insufficient expression of a particular protein or expression of a malfunctioning version of a protein. In some embodiments, the disease or disorder is an acquired disorder, for example, cardiovascular disease or disorder as disclosed herein.

In another embodiment, the methods and compositions and kits as disclosed herein for in vivo protein expression using synthetic modified RNAs can be used in regenerative medicine strategies as well. For example, in some embodiments, a composition comprising at least one synthetic modified RNA encoding a protein of interest can also comprise a population of cells of interest. Stated another way, in some embodiments, the present invention provides methods for regenerative cell therapy comprising administering to the subject a combination of at least one synthetic modified RNAs with a population of cells of interest. In some embodiments, a cell population is a stem cell population, and in some embodiments a stem cell population is a population of cardiac precursor cells or cardiac progenitor cells. In some embodiments a stem cell is an Isl1+ stem cell population, or is a vascular progenitor cell population. Such cell populations are well known in the art, and include, but are not limited to the cell populations disclosed in International Patent Applications, WO/2008/054819, WO2010/144678, WO2010/042856, and U.S. Patent Applications 2010/0166714, US2011/0033430, US2010/021713 and US2011/0003327, which are incorporated herein in their entirety by reference. In some embodiments, a cell population is a Isl1+ primordial cell, or a progeny thereof as disclosed in WO2010/144678.

As disclosed herein, one aspect of the present invention relates to the use of synthetic modified RNAs (herein referred to as "MOD-RNA") to induce protein expression in tissues, e.g., heart tissue and muscle tissue, such as but not limited to cardiomyocytes and myocytes both in vitro and in vivo. In some embodiments, the cardiomyocytes are mammalian cardiomyocytes, for example human cardiomyocytes.

In particular, as demonstrated herein in the Examples, transfection of functional cardiomyocytes (CM) with MOD-RNA in vitro and in vivo results in a very rapid onset of protein expression, with protein expression levels significantly higher, e.g., at least about 2-fold higher, as compared to cells transfected than non-MOD RNA. Also demonstrated herein is that an optimal dose range for transfection of mouse neonatal and for human fetal cardiomyocytes in vitro with MOD-RNA is between 10-30 ng per 1000 cells, and that such a dose is non-toxic to cells.

Also demonstrated herein is the highly efficient and rapid protein expression in vivo after transfection of heart and muscle tissue with MOD-RNA. The inventors demonstrate that protein expression occurs by at least 3 hours or earlier after transfection, and that in vivo protein expression from the MOD-RNA occurs for at least a 4-5 days after direct injection of the MOD-RNA into the muscle or heart. As disclosed herein in the Examples, the transfection of heart tissue and muscle with MOD-RNA in vivo results in a low immunological response. Importantly, the inventors demonstrate that the level of protein expression in vivo is dose-dependent on the amount of MOD-RNA injected into the heart or muscle in vivo, enabling one to titrate the amount of MOD-RNA administered to the tissue for the desired amount of protein expression required. Accordingly, the ability to titrate the amount of protein expressed is very useful where the synthetic modified RNAs are being used for in vivo protein expression in protein replacement therapy or other therapeutic methods.

Another aspect of the present invention relate to methods to treat a disease or disorder in a subject comprising administering a composition comprising a synthetic modified RNA encoding a polypeptide to the subject. In some embodiments, a composition can be delivered to a specific tissue in the subject, and in some embodiments, the tissue is muscle tissue. In some embodiments, the muscle tissue is skeletal muscle, cardiac muscle or smooth muscle.

In some embodiments, the methods as disclosed herein comprise delivering a synthetic modified RNA encoding a polypeptide of interest to a muscle tissue in a subject for the treatment of one or more diseases, for example, but not limited to the following muscle diseases: cardiomyopathy (ischemic and non-ischemic), skeletal myopathy, cystic fibrosis, muscular dystrophy. In some embodiments, for the treatment of cardiomyopathy, one can deliver a synthetic modified RNA encoding VEGF, e.g., hVEGF to the heart of the subject. In some embodiments, the synthetic modified RNA encoding VEGF can be delivered to the myocardium via direct intra-myocardial injection.

The inventors have demonstrated herein that the in vivo delivery a synthetic modified RNA encoding a hVEGF polypeptide to the heart of a mouse model of myocardial infarction prevents a myocardial infarct from occurring and significantly prevents damage to the heart after ischemic insult. In some embodiments, in vivo delivery a synthetic modified RNA encoding a hVEGF polypeptide also promoted recovery of the heart from ischemia. Accordingly, in one embodiment, the methods as disclosed herein relate to a method of delivering a synthetic modified RNA encoding VEGF to a heart tissue, e.g., a cardiac muscle tissue in a subject for the treatment heart attack and/or myocardial infarction.

In some embodiments, the methods and compositions are useful in a method for the treatment of muscular dystrophy, where, for example, one can deliver a synthetic modified RNA encoding one or more genes, and can be delivered to one or more muscle tissue targets. For example, in some embodiments where the method is for the treatment of Duchenne/Becker Muscular Dystrophy, one can deliver a synthetic modified RNA encoding a non-mutated version of the Dystrophin protein. In alternative embodiments where the method is for for the treatment of Emery-Dreyfuss muscular dystrophy, one can deliver a synthetic modified RNA encoding a Emerin and/or Lamin protein.

In some embodiments, a synthetic modified RNA encoding dystrophin and/or Emerin and/or Lamin protein can be delivered to a muscle tissue with the most marked disability associated with the condition, notably insufficient respiration due to a weakened thoracic diaphragm and inability to ambulate due to weak postural muscles. For diaphragmatic injection, one can use a thoracoscopic approach for the direct injection of a synthetic modified RNA encoding a dystrophin and/or Emerin and/or Lamin protein into a diaphragm muscle. In some embodiments, one can deliver a synthetic modified RNA encoding dystrophin directly by injection into skeletal muscles, for example, direct injection into a pelvic girdle and shoulder girdle muscles associated with maintenance of posture and gross arm movements, respectively.

In another embodiment, the methods and compositions are useful in a method for the treatment of cystic fibrosis, where, for example, one can deliver a synthetic modified RNA encoding a non-mutated (wild-type) CFTR protein to the diaphragm of the subject. In some embodiments, a synthetic modified RNA encoding CFTR can be delivered by direct parenchymal injection and/or intrabronchial introduction of a synthetic modified RNA that encodes for a non-mutated CFTR protein. Accordingly, any means to deliver a synthetic modified RNA encoding a desired polypeptide for the treatment of a disease or disorder is encompassed herein, and for example encompassed herein are direct bowel and pancreas injections, via laparoscopic and endoscopic approaches respectively, for the treatment of subjects with disorders associated with these organ and systems.

In some embodiments, the methods as disclosed herein are directed to delivering a synthetic modified RNA encoding a polypeptide of interest to a tissue in a subject for the treatment of one or more diseases, where a synthetic modified RNA is delivered by an implantable device, e.g., a drug-delivery device such as a drug-delivery pump, or alternatively, using a flexible injection catheter, e.g., to facilitate multiple injections from a single entry point, and/or repeated injections to a single site.

In some embodiments, a synthetic modified RNA encoding a polypeptide of interest is delivered to a tissue in a subject on the exterior of an implantable device, e.g., the synthetic modified RNA encoding a polypeptide of interest is coated on the outside of an implantable device. In some embodiments, where the disease to be treated is a cardiac disease or disorder as disclosed herein, a synthetic modified RNA encoding a polypeptide of interest is coated on an stent.

Additionally, the inventors have also demonstrated that cardiomyocytes can be transfected with a plurality of MOD-RNAs in vitro and in vivo, e.g., at least two MOD-RNA's to express at least two-different proteins at one time, and double transfection of human fetal cardiomyocytes with MOD-RNA reveals that cells are unable to discriminate between different MOD-RNA and both RNAs been translated in the cells.

In some embodiments, the methods and compositions and kits as disclosed herein for in vivo protein expression using synthetic modified RNAs provide a platform by which investigators can explore whole-organ and systemic effects of the protein expression of a single gene product or group of gene products. The ability to perform specific, directed protein expression in a facile manner (as compared with transgenic mouse technology and other genetic modification techniques in whole animals) opens new frontiers in the study of organ and system physiology. Such a powerful platform would have broad interest among biological and clinical scientists. In some embodiments, the present invention provides to methods to delivery synthetic modified RNA in vivo to an animal model to turn on and/or turn off gene expression, for example, for an inducible protein expression system. In some embodiments, the methods provide for delivering a synthetic modified RNA encoding Cre recombinase protein to an animal model to see effects of knock out of genes in particular tissues and/or cell types. In some embodiments the animal models are large animal models, e.g., porcine models.

For example, demonstrated herein is the in vivo transfection of a ROSA-Cre stop-LacZ mouse with a Cre MOD-RNA to selectively induce gene expression from the Cre locus, enabling a method for directed, reversible and specific transient gene expression methods useful as a tool for research purposes.

One aspect of the present invention relates to a method for expressing a protein in a tissue in vivo, the method comprising contacting the tissue with a composition comprising a synthetic, modified RNA molecule encoding a polypeptide, wherein the synthetic, modified RNA molecule comprises one or more modifications, such that introducing said synthetic, modified RNA molecule to a cell in the tissue results in a reduced innate immune response relative to cell in the tissue contacted with a synthetic RNA molecule encoding the polypeptide not comprising said one or more modifications.

In some embodiments, the tissue is heart tissue or cardiac tissue, or muscle tissue, e.g., skeletal muscle, cardiac muscle, or smooth muscle. In some embodiments, a tissue is a mammalian tissue, e.g., a human tissue.

Synthetic modified RNA's for use in the compositions, methods and kits as disclosed herein are described in U.S. Provisional Application 61/387,220, filed Sep. 28, 2010, and U.S. Provisional Application 61/325,003, filed on Apr. 16, 2010, both of which are incorporated herein in their entirety by reference. In some embodiments, the synthetic, modified RNA molecule is not expressed in a vector, and the synthetic, modified RNA molecule can be a naked synthetic, modified RNA molecule. In some embodiments, a composition can comprises at least one synthetic, modified RNA molecule present in a lipid complex.

In some embodiments, the synthetic, modified RNA molecule comprises at least two modified nucleosides, for example, at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I). In some embodiments, the synthetic, modified RNA molecule further comprises a 5' cap, such as a 5' cap analog, e.g., a 5' diguanosine cap. In some embodiments, a synthetic, modified RNA molecule for use in the methods and compositions as disclosed herein does not comprise a 5' triphosphate. In some embodiments, a synthetic, modified RNA molecule for use in the methods and compositions as disclosed herein further comprises a poly(A) tail, a Kozak sequence, a 3' untranslated region, a 5' untranslated region, or any combination thereof, and in some embodiments, the a synthetic, modified RNA molecule can optionally treated with an alkaline phosphatase.

In some embodiments, a synthetic, modified RNA molecule for use in the methods, kits and compositions as disclosed herein encodes a protein of interest, selected from any or a combination from those listed in Table 1. In some embodiments, a synthetic, modified RNA molecule encodes a VEGF polypeptide, e.g., human VEGF (hVEGF). In some embodiments, a synthetic, modified RNA molecule encodes a dystrophin polypeptide, or alpha 1 anti-trypsin polypeptide. In some embodiments, a synthetic, modified RNA molecule encodes a polypeptide for a loss of function disease, for example, for cystic fibrosis, where the protein expressed from the MOD-RNA is cystic fibrosis transmembrane conductance regulator (CFTR) polypeptide.

In some embodiments, a synthetic, modified RNA molecule is directly injection into the muscle. In some embodiments, a synthetic, modified RNA molecule is present in, or on (e.g., coated on) an implantable device, for example where the implantable device is a stent, or an implantable drug-delivery pump. In some embodiments, a synthetic, modified RNA molecule is delivered to a target tissue via a catheter, or via an endoscope.

In some embodiments, a composition comprising a synthetic, modified RNA molecule encoding a protein of interests for protein expression in a target tissue in vivo comprises a concentration of synthetic, modified RNA molecule of greater than 100 ng/μl, for example, a concentration of about 1-25 μg/μl, or a between 25 μg/μl and 50 μg/μl.

Another aspect of the present invention relates to a method for enhancing cardiac function in a subject, the method comprising administering to the subject a composition comprising a synthetic, modified RNA molecule encoding a polypeptide which enhances the cardiac function in the subject, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein expression of the polypeptide from the synthetic, modified RNA molecule enhancing cardiac function in the subject.

In some embodiments, a subject suffers from a disease or disorder characterized by insufficient cardiac function, or a subject suffers from a structural heart disease. In some embodiments, the methods as disclosed herein are useful for treatment of a disease or disorder which is congestive heart failure, cardiomyopathy, myocardial infarction, tissue ischemia, cardiac ischemia, vascular disease, acquired heart disease, congenital heart disease, atherosclerosis, cardiomyopathy, dysfunctional conduction systems, dysfunctional coronary arteries, pulmonary heard hypertension. In some embodiments, the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis and congenital heart disease. In some embodiments, a synthetic, modified RNA molecule for use in the methods, kits and compositions for methods to enhance cardiac function encodes a protein of interest, selected from any or a combination from those listed in Table 1, Table 2, Table 3, Table 4, Table 5, or Table 6. In some embodiments, a synthetic, modified RNA molecule for use in the methods, kits and compositions for methods to treat liposomal storage diseases, where the MOD-RNA encodes a protein selected from any or a combination of polypeptides, but is not limited to, the polypeptides those listed in Table 7.

In some embodiments, a cardiac enhancing protein expressed by a synthetic, modified RNA molecule is a VEGF polypeptide, e.g., human VEGF (hVEGF). In some embodiments, the synthetic, modified RNA molecule encodes an alpha 1 anti-trypsin polypeptide, or a encodes a polypeptide for a loss of function disease, for example, the synthetic modified RNA molecule expresses a polypeptide which is not expressed in the heart, or is expressed at low levels as compared to normal expression in the heart, or is expressed as a gain of function or mutant protein as compared to the native wild-type form of the polypeptide in the subject.

In some embodiments, the methods as disclosed herein relate to the treatment of a mammalian subject, e.g., a human. In some embodiments, a subject has suffered myocardial infarction, or has or is at risk of heart failure, e.g., where the subject has acquired heart failure. In further embodiments, the heart failure is associated with atherosclerosis, cardiomyopathy, congestive heart failure, myocardial infarction, ischemic diseases of the heart, atrial and ventricular arrhythmias, hypertensive vascular diseases, peripheral vascular diseases. In some embodiments, methods as disclosed herein relate to the treatment of subject with a congenital heart disease, e.g., where the subject has a condition selected from a group consisting of: hypertension; blood flow disorders; symptomatic arrhythmia; pulmonary hypertension; arthrosclerosis; dysfunction in conduction system; dysfunction in coronary arteries; dysfunction in coronary arterial tree and coronary artery colaterization. In some embodiments, the methods as disclosed herein relate to the treatment or prevention of heart failure.

In some embodiments, a synthetic, modified RNA molecule can be administered to a subject via endomyocardial, epimyocardial, intraventricular, intracoronary, retrosinus, intra-arterial, intra-pericardial, or intravenous administration route. In some embodiments, a synthetic, modified RNA molecule can be administered to a subject via intramuscular injection, for example, where the muscle serves as a biological pump (e.g., biopump) for protein expression in vivo, for example, where the MOD-RNA encodes a secreted protein.

Another aspect of the present invention relates to the use of a synthetic, modified RNA molecule encoding a Cre recombinase polypeptide to knock out a gene in an in vivo Cre animal model.

In one aspect, the invention described herein relates to a method for treating a tumor in a subject, the method comprising; administering a compositions comprising a synthetic, modified RNA molecule encoding a polypeptide which enhances neovascularization in the subject, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein expression of the polypeptide from the synthetic, modified RNA molecule enhances neovascularization in the tumor; and administering a chemotherapeutic agent to the subject; wherein the neovascularization increases the effectiveness of a chemotherapeutic agent administered to the subject; whereby the tumor is treated. In an additional aspect, the invention described herein relates to a method for treating a tumor in a subject, the method comprising; administering a compositions comprising a synthetic, modified RNA molecule which inhibits the expression of a polypeptide which enhances Hedgehog signaling in the tumor, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein inhibition of the polypeptide which enhances Hedgehog signaling by the synthetic, modified RNA molecule reduces the amount or proliferation of desmoplastic tissue associated with the tumor; and administering a chemotherapeutic agent to the subject; wherein the reduced amount or proliferation of the desmoplastic tissue increases the effectiveness of a chemotherapeutic agent administered to the subject; whereby the tumor is treated.

In some embodiments, the synthetic, modified RNA molecule is not expressed in a vector. In some embodiments, the composition comprising the synthetic, modified RNA molecule comprises a naked synthetic, modified RNA molecule. In some embodiments, the composition comprising the synthetic, modified RNA molecule comprises at least one synthetic, modified RNA molecule present in a lipid complex.

In some embodiments, the synthetic, modified RNA molecule comprises at least two modified nucleosides. In some embodiments, the at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I). In some embodiments, the synthetic, modified RNA molecule, wherein the at least two modified nucleosides are 5-methylcytidine (5mC) and pseudouridine.

In some embodiments, the synthetic, modified RNA molecule further comprises a 5' cap. In some embodiments, the synthetic, modified RNA molecule, wherein the 5' cap is a 5' cap analog. In some embodiments, the 5' cap analog is a 5' diguanosine cap. In some embodiments, the synthetic, modified RNA molecule does not comprise a 5' triphosphate.

In some embodiments, the synthetic, modified RNA molecule further comprises a poly(A) tail, a Kozak sequence, a 3' untranslated region, a 5' untranslated region, or any combination thereof. In some embodiments, the poly(A) tail, the Kozak sequence, the 3' untranslated region, the 5' untranslated region, or the any combination thereof comprises one or more modified nucleosides. In some embodiments, the one or more modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I). In some embodiments, the synthetic, modified RNA molecule is treated with an alkaline phosphatase.

In some embodiments, the subject suffers from an adenocarcinoma. In some embodiments, the subject suffers from a cancer comprising a tumor having a layer of desmoplastic tissue. In some embodiments, the cancer is pancreatic ductal adenocarcinoma (PDAC).

In some embodiments wherein neovascularization is increased, the synthetic, modified RNA molecule encodes a VEGF polypeptide. In some embodiments, the VEGF polypeptide is human VEGF (hVEGF). In some embodiments, the synthetic, modified RNA molecule encodes a polypeptide disclosed in Table 3.

In some embodiments wherein the expression of a polypeptide which enhances Hedgehog signaling is inhibited, the synthetic, modified RNA molecule is an antisense inhibitor of a mRNA selected from the group consisting of mRNAs encoding Hedehog (Hh); Smoothened (Smo); Patched 1 (Ptc1); and Gli. In some embodiments, the polypeptide which enhances Hedgehog signaling is a human polypeptide.

In some embodiments, the subject is a mammal. In some embodiments, the mammal is a human.

In some embodiments, the composition is administered via intravenous or trans-tumoral administration route. In some embodiments, the composition is administered to the subject's vasculature. In some embodiments, the composition is administered to the subject by direct injection into the tumor. In some embodiments, the composition is administered to the subject using an implantable device, wherein the implantable device comprises or is coated with the synthetic, modified RNA molecule. In some embodiments, the composition is administered to the subject by a catheter. In some embodiments, the composition is administered to the subject via an endoscope.

In some embodiments, the composition comprises a concentration of synthetic, modified RNA molecule of greater than 100 ng/µl. In some embodiments, the composition comprises a concentration of synthetic, modified RNA molecule of between 1-25 µg/µl. In some embodiments, the composition comprises a concentration of synthetic, modified RNA molecule of between 25 µg/µl and 50 µg/µl.

In some embodiments, the chemotherapeutic agent is selected from the group consisting of: gemcitabine; fluorouracil, capecitabine; ciplastin; irinotecan; oxaliplatin; 5-fluorouracil; folinic acid; and erlotinib.

BRIEF DESCRIPTION OF FIGURES

FIGS. 1A-1B show FACS analysis of mouse neonatal cardiac cells transfected with eGFP Modified mRNA (MOD-RNA). Neonatal cardiac cells were transfected at 2 ng/1000 cells. FIG. 1A shows FL-4 and FL-1 fluorescence and FIG. 1B shows Thy-1 and eGFP MOD-RNA florescence. A total of 58.5% cardiac cells transfected, with 62.2% of cardiac-fibroblasts being transfected, and 52.2% of cardiac non-fibroblast being transfected.

FIG. 2A shows a histogram of the results for the number of cells counted for viability and the number of Troponin T positive cells in which eGFP was present or absent. Shown is the % cells transfected which are double positive for troponin T and eGFP, demonstrating that at 3 ng/1000 cells, 81.4% of cells are TnT+/eGFP+, and at 15 ng/1000 cells, 89.1% of cells are TnT+/eGFP+, and at 30 ng/1000 cells, 90.5% of cells are TnT+/eGFP+. FIG. 2B shows the % of intact living cells with increasing dose of eGFP MOD-RNA, demonstrating concentrations of MOD-RNA between 0-30 ng per 1000 cells does not induce cell death.

FIG. 3A shows a histogram of the results for the number of human fetal cardiomyocytes counted for viability and the number of Troponin T positive cells in which eGFP was present or absent. Shown is the % cells transfected which are double positive for troponin T and eGFP, demonstrating that at 1 ng/1000 cells, 21.6% of the cells are TnT+/eGFP+, and at 2 ng/1000 cells, 34.4% of cells are TnT+/eGFP+, and at 5 ng/1000 cells, 43.3% of cells are TnT+/eGFP+, at 10 ng/1000 cells, 63.3% of cells are TnT+/eGFP+, and at 30 ng/1000 cells, 71.9% of cells are TnT+/eGFP+. FIG. 3B shows the % of intact living cells with increasing dose of eGFP MOD-RNA, demonstrating concentrations of MOD-RNA between 1-30 ng per 1000 cells does not induce cell death in human fetal cardiomyocytes.

FIG. 4 shows results from bioluminescent analysis to quantitate the luciferase (luc) protein expression in cardiomyocytes (CM) or cardiac-fibroblasts (CF) after transfection in vitro with luciferase MOD-RNA at a concentration of 10 μg per 1000 cells. High levels of luciferase expression is detected in both CM and CF for at least about 24 hours from transfection, with MOD-RNA luciferase expression occurring for at least about 50 hrs after transfection.

FIG. 5A shows results from bioluminescent analysis to quantitate the luciferase (luc) protein expression in heart muscle or quadriceps muscle after in vivo transfection with luciferase MOD-RNA at a concentration of 100 μg per tissue. High levels of luciferase expression is detected in both heart tissue and quadriceps tissue at least about 24 hours after in vivo transfection, with luciferase expression occurring for at least about 50 hours and 25 hours after transfection for the heart and leg muscle respectively. FIG. 5B shows a time course of expression of the Luc (Y axis) measured after injection of the Luc MOD RNA (100 μg/heart).

FIG. 8 shows a histogram of gene expression at 1 day (left panel) and 4 days (right panel) post in vivo delivery of hVEGF MOD-RNA.

FIG. 9A shows the results of an experiment where distinct compartments of human fetal hearts (13 gestation weeks) were digested and examined using real-time qPCR for their gene expression of various isoforms of VEGF. Outgrowth endothelial cells used as control (dash line). Five bars are shown for each compartment; the first bar depicts the expression of VEGF-A; the second bar depicts the expression of VEGF-B; the third bar depicts the expression of VEGF-C; the fourth bar depicts the expression of VEGF-D; and the fifth bar depicts the expression of PLGF. FIG. 9B shows the percentage of MOD RNA transfected cardiomyocytes (cTropT and eGFP double positive cells) after transfection with vehicle only or different doses of eGFP MOD RNA. FIG. 9C shows the percentage of viable cells after transfection with vehicle only or different doses of eGFP MOD RNA. FIG. 9D shows a time course for Luc protein translation and expression. FIG. 9E shows a time course for VEGF-A protein translation and secretion after transfection with the hVEGF-A MOD RNA.

FIG. 10A is a schematic depicting the experimental design. FIG. 10B shows the capillary density quantification for control (C.) versus experimental hearts (E.). FIG. 10C shows the percent of fibrotic cells in control (left bar) and experimental hearts (right bar). FIG. 10D shows the percentage of Ki67+ cells among different cell types. The bars on the left for each group of cells represents the control group, while the bars on the right represent experimental group. FIG. 10E shows the percentage of TUNEL positive cells in the control (left bar) vs. experimental group (right bar). FIG. 10F shows Cine-MRI images of diastolic and systolic volume for sham (uppermost bar), vehicle treated (middle bar) or hVEGF-A MOD RNA-treated hearts (lowermost bar).

FIGS. 11A and 11B are schematics depicting the experimental protocols used herein. FIG. 11C shows FACS sorting for genetic labeled WT1 eGFP+ cells after different treatments. FIG. 11D shows FACS sorting for WT1-derived cells (eGFP+ and tomato) after different treatments. FIG. 11E shows quantification of WT-1 derived cells after different treatments (MI+vehicle treatment (left bar) and MI+hVEGF-A MOD RNA (right bar). FIG. 11F shows lineage tracing for cell fate of WT1-derived cells after different treatments. Time course of expression of the Luc (Y axis) measured after injection of the Luc MOD RNA (100 µg/heart). FIG. 11G shows a model of cell fate switch from the fibroblastic to the cardiovascular lineage.

FIG. 12A shows a time course by which VEGF-A protein was translated and secreted from cells transfected with the hVEGF-A nonMOD RNA. FIG. 12B shows total hVEGF-A protein collected from supernatant over 10 days after transfection adult cardiac cells with 1 µg hVEGF-A MOD or nonMOD RNA. FIG. 12C shows the total cell number of viable cells without treatment (no transfection) or with treatment of vehicle, hVEGF-A MOD RNA or nonMOD RNA. FIG. 12D shows Annexin V staining for the different treatment groups. FIG. 12E shows gene expression of murine (left bars in each group) or human (Right bars) VEGF-A as compared after transfecting adult cardiac cells in vitro or in vivo with hVEGF-A MOD or nonMOD RNA on day 4. FIG. 12F shows gene expression of different innate immune genes as compared in different treatment groups. The first bar in each group depicts gene expression of INF-α; the second bar depicts the expression of INF-β; and the third bar depicts the expression of RIG-1.

FIG. 13A shows a schematic depicting the experimental design. FIG. 13B shows data 7 days post-MI where infarcted areas were dissected and examined for gene expression of various cardiac genes. Hearts treated with vehicle only after MI were used for normalization (dashed line). FIGS. 13C-13D show quantification for capillary density (FIG. 13C) or fibrotic area after different treatments (FIG. 13D) (left bars represent MI+vehicle treatment; right bars represent MI+hVEGF-A MOD RNA treatment)

FIGS. 14A and 14B are schematics depicting the experimental design. FIG. 14C shows data 7 days post MI wherein FACS sorted, genetic labeled WT1 eGFP+ cells were examined for gene expression of various cardiac genes. WT1 eGFP+ cells isolated from hearts treated with vehicle only after MI were used for normalization (the dashed line). FIG. 14D shows data 7 days post-MI wherein FACS sorted WT1-derived cells (eGFP+ and Tomato+ cells) were examined for gene expression of various cardiac genes. WT1-derived cells (eGFP+ and Tomato+ cells) isolated form hearts treated with vehicle only after MI were used for normalization (dashed line). FIG. 14E shows WT1 eGFP+ cells stained for FLK-1 after different treatments. The first peak depicts treatment with secondary antibody only; the second peak depicts no MI treatment; the third peak depicts 7 days post MI+vehicle treated; and the fourth peak depicts 7 days post MI+VEGF-A MOD RNA. FIG. 14F shows a schematic experiment designed to determine the leakiness of the WT1/CreERT2/+::R26 mTmG mouse model in the absence or presence of hVEGF-A MOD RNA.

DETAILED DESCRIPTION

Figure 2A:
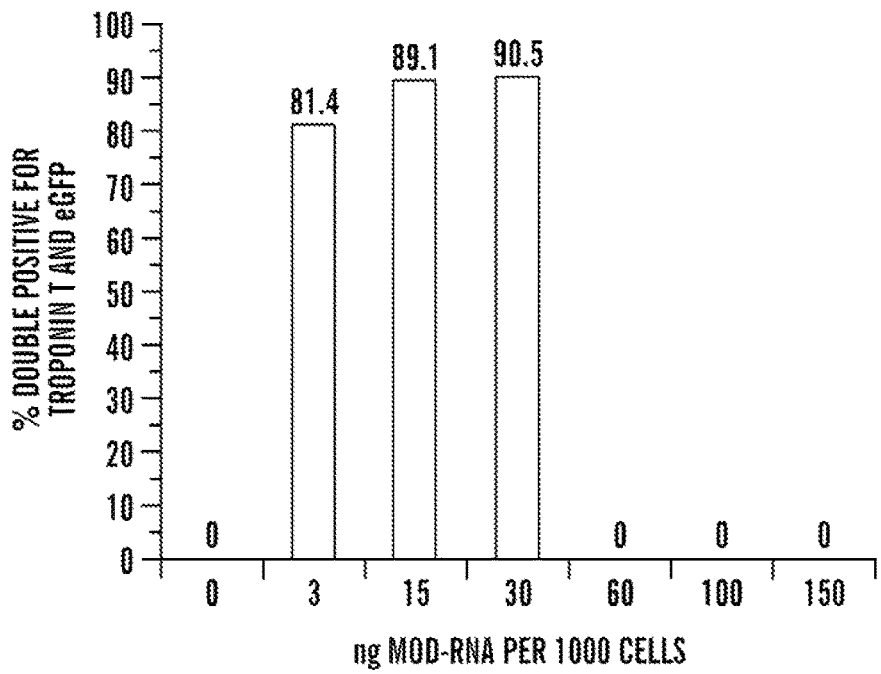
FIGS. 2A-2B show an embodiment of the optimal dose for transfecting mouse neonatal cardiomyocytes with eGEP MOD-RNA in vitro. Isolated mouse neonatal cardiomyocytes were transfected with different doses of eGFPMOD-RNA (green, 0-50 ng per 1000 cells).
Figure 2B:
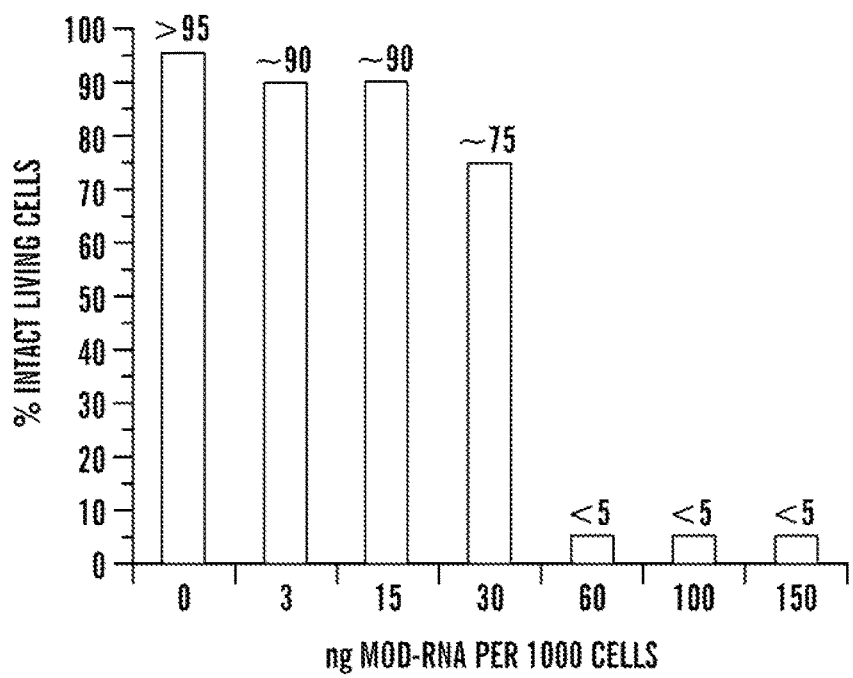
Figure 3A:
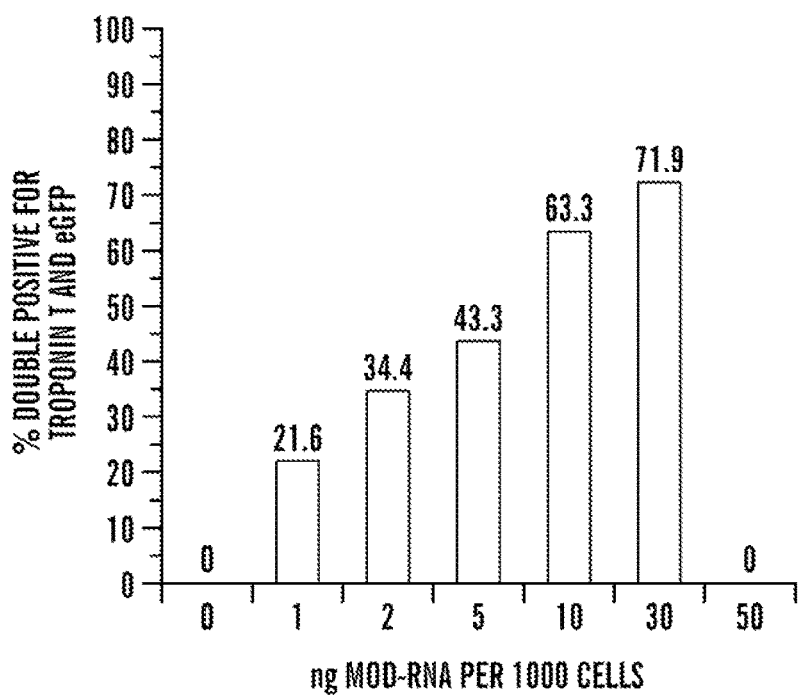
FIGS. 3A-3B show an embodiment of the optimal dose for transfecting human fetal cardiomyocytes with eGEP MOD-RNA in vitro. Isolated human fetal cardiomyocytes were transfected with different doses of eGFPMOD-RNA (green, 0-50 ng per 1000 cells).
Figure 3B:
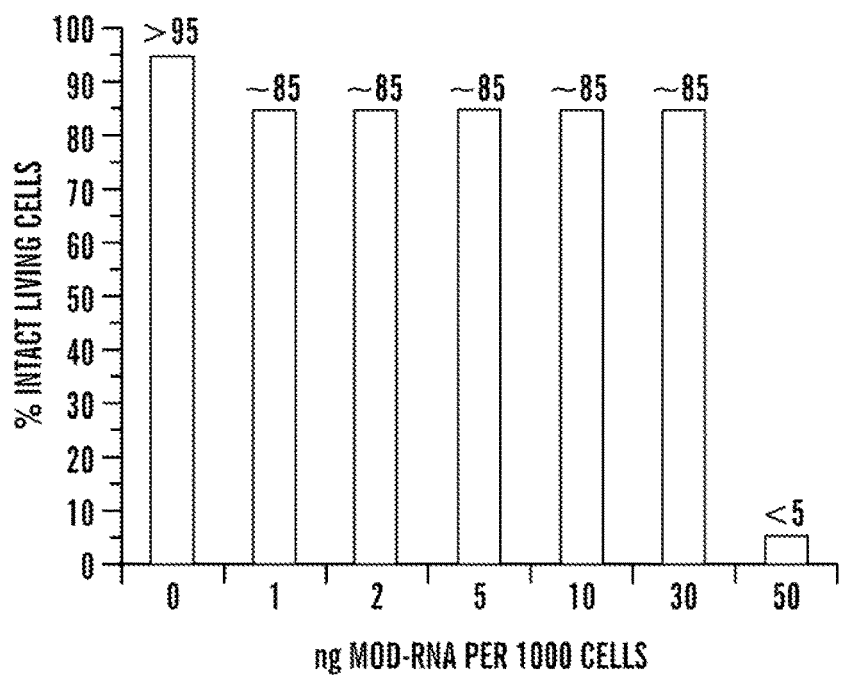

Described herein are compositions and methods and kits for in vivo expression of a protein in a tissue, by delivering a synthetic modified RNA (MOD-RNA) encoding a polypeptide of interest. The tissue be any tissue in a subject, for example, in some embodiments, the tissue is a muscle tissue or heart tissue. In some embodiments, the methods, compositions and kits as disclosed herein for in vivo expression of a protein in a tissue using a synthetic modified RNA (MOD-RNA) encoding a polypeptide of interest is useful in methods for the treatment of a disease or disorder. In some embodiments, the disease or disorder is a cardiovascular disease or disorder as disclosed herein.

In some embodiments, the methods, compositions and kits as described herein are useful for change a property of a cell, e.g., a myocyte, e.g., a cardiomyocyte in vitro, ex vivo or in vivo, using synthetic modified RNA (MOD-RNA). In some embodiments, a myocyte e.g., a cardiomyocyte is mammalian, for example, it can be a human myocyte or human cardiomyocyte.

Other aspects relate to the use of synthetic, modified RNAs as disclosed herein in a method for the treatment of a cardiovascular disease or disorder in a subject. Other aspect of the present invention relate to a pharmaceutical comprising a synthetic, modified RNAs, for use in the treatment of a cardiac disease or disorder. In alternative embodiments, a population of cardiac cells, e.g., a population of cardiomyocytes, or cardiomyocyte precursor cells (e.g., cardiac stem cells) can be contacted with a synthetic modified RNA (MOD-RNA) in vitro, in vivo or ex vivo, and in some embodiments, where the contact occurs in vitro or ex vivo, the population of cardiac cells, e.g., cardiomyocytes can be transplanted into a subject for the treatment and/or prevention of cardiac diseases, or for the treatment of existing cardiac muscle which is damaged by disease or injury. In alternative embodiments, the present invention provides for methods to treat a cardiovascular disease or disorder in a subject comprising administering to the subject a composition comprising a population of cardiac cells, e.g., population of cardiac stem cells or ventricular cardiac stem cells and at least one synthetic modified RNA encoding a protein of interest as disclosed herein. In some embodiment, a cardiac cell is a population of cardiac cells differentiated from an induced pluripotent stem cell (iPS), and in some embodiments, the iPS cell is an autologous iPS cell e.g., an iPS cell which was reprogrammed from a somatic cell obtained from a subject to which the pharmaceutical composition is being administered to. In some embodiments, a cardiac cell is a population of primordial or cardiac cell precursor, or their progeny, as disclosed in International Patent Applications, WO/2008/054819, WO2010/144678, WO2010/042856, and U.S. Patent Applications 2010/0166714, US2011/0033430, US2010/021713 and US2011/0003327, which are incorporated herein in their entirety by reference. In some embodiments, a cell population is a Isl1+ primordial cell, or a progeny thereof as disclosed in WO2010/144678.

Accordingly, one aspect of the present invention relates to use of MOD-RNAs for the production of a pharmaceutical composition, for example, for the transplantation into a subject in need of cardiac regenerative therapy, for example subjects with congenital heart diseases as well as subjects with acquired congenital defects or diseases, such as, for example cardiac muscle which is damaged by disease or injury. In some embodiments, a composition comprises MOD-RNAs encoding a cardiac enhancing protein as described herein, and can optionally also comprise cardiac cells. In some embodiments, a composition comprises cardiac cells which have been contacted in vitro or ex vivo with a MOD-RNA encoding a cardiac enhancing protein. In some embodiments, subject amenable to treatment with the pharmaceutical composition as disclosed herein include, for example congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis and congenital heart disease.

Other aspects of the invention described herein relate to methods of treating tumors in a patient by increasing the efficacy of a chemotherapeutic agent via delivering a MOD-RNA. The efficacy of the chemotherapeutic agent is increased by increasing the ability of the agent to penetrate the tumor by (i) increasing neovascularization and/or (ii) decreasing the amount of or the rate of proliferation of the desmoplastic tissue of the tumor, which is typically refractory to chemotherapeutic agents. In some embodiments, the synthetic, modified RNA molecule encodes a polypeptide which enhances neovascularization in the subject. In some embodiments, the synthetic, modified RNA molecule is an antisense inhibitor which inhibits the expression of a polypeptide which enhances Hedgehog signaling in the tumor.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "cardiomyocyte" as used herein broadly refers to a muscle cell of the heart. The term cardiomyocyte includes smooth muscle cells of the heart, as well as cardiac muscle cells, which include also include striated muscle cells, as well as spontaneous beating muscle cells of the heart.

The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a more specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at one time in their development.

The term "enriching" is used synonymously with "isolating" cells, and means that the yield (fraction) of cells of one type is increased over the fraction of cells of that type in the starting culture or preparation.

The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers.

A "marker" as used herein describes the characteristics and/or phenotype of a cell. Markers can be used for selection of cells comprising characteristics of interest. Markers vary with specific cells. Markers are characteristics, whether morphological, functional or biochemical (enzymatic) characteristics particular to a cell type, or molecules expressed by the cell type. Preferably, such markers are proteins, and more preferably, possess an epitope for antibodies or other binding molecules available in the art. A marker may consist of any molecule found in, or on the surface of a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method commonly available to one of skill in the art.

A "reporter gene" as used herein encompasses any gene that is genetically introduced into a cell that adds to the phenotype of the stem cell. Reporter genes as disclosed in this invention are intended to encompass fluorescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny.

The term "lineages" as used herein refers to a term to describe cells with a common ancestry, for example cells that are derived from the same cardiovascular stem cell or other stem cell.

As used herein, the term "clonal cell line" refers to a cell lineage that can be maintained in culture and has the potential to propagate indefinitely. A clonal cell line can be a stem cell line or be derived from a stem cell, and where the clonal cell line is used in the context of a clonal cell line comprising stem cells, the term refers to stem cells which have been cultured under in vitro conditions that allow proliferation without differentiation for months to years. Such clonal stem cell lines can have the potential to differentiate along several lineages of the cells from the original stem cell.

The term "phenotype" refers to one or a number of total biological characteristics that define the cell or organism under a particular set of environmental conditions and factors, regardless of the actual genotype.

The term "tissue" refers to a group or layer of similarly specialized cells which together perform certain special functions. The term "tissue-specific" refers to a source or defining characteristic of cells from a specific tissue.

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "enriching" or "enriched" are used interchangeably herein and mean that the yield (fraction) of cells of one type is increased by at least 10% over the fraction of cells of that type in the starting culture or preparation.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not stem cells or stem cell progeny.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" or "recombinant gene" refers to a nucleic acid comprising an open reading frame encoding a polypeptide, including both exon and (optionally) intron sequences.

The term "recombinant," as used herein, means that a protein is derived from a prokaryotic or eukaryotic expression system.

As used herein, the term "vector" refers to a nucleic acid molecule capable of transporting another nucleic acid to which it has been linked Preferred vectors are those capable of autonomous replication and/or expression of nucleic acids to which they are linked Vectors capable of directing the expression of genes to which they are operatively linked are referred to herein as "expression vectors".

The terms "subject" and "individual" are used interchangeably herein, and refer to an animal, for example a human, to whom treatment, including prophylactic treatment, with methods and compositions described herein, is or are provided. For treatment of those infections, conditions or disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates.

The term "regeneration" means regrowth of a cell population, organ or tissue after disease or trauma.

The terms "disease" or "disorder" are used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affection.

As used herein, the phrase "cardiovascular condition, disease or disorder" is intended to include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The term "pathology" as used herein, refers to symptoms, for example, structural and functional changes in a cell, tissue or organs, which contribute to a disease or disorder.

For example, the pathology may be associated with a particular nucleic acid sequence, or "pathological nucleic acid" which refers to a nucleic acid sequence that contributes, wholly or in part to the pathology, as an example, the pathological nucleic acid may be a nucleic acid sequence encoding a gene with a particular pathology causing or pathology-associated mutation or polymorphism. The pathology may be associated with the expression of a pathological protein or pathological polypeptide that contributes, wholly or in part to the pathology associated with a particular disease or disorder. In another embodiment, the pathology is for example, is associated with other factors, for example ischemia and the like.

As used herein, the terms "treat" or "treatment" or "treating" refers to therapeutic treatment, wherein the object is to prevent or slow the development of the disease, such as slow down the development of a cardiac disorder, or reducing at least one adverse effect or symptom of a cardiovascular condition, disease or disorder, i.e., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health. In some embodiments, the term to treat also encompasses preventative measures and/or prophylactic treatment, which includes administering a pharmaceutical composition as disclosed herein to prevent the onset of a disease or disorder.

The term "effective amount" as used herein refers to the amount of therapeutic agent of pharmaceutical composition, e.g., an amount of the synthetic modified RNA to express sufficient amount of the protein to reduce at least one or more symptom(s) of the disease or disorder, and relates to a sufficient amount of pharmacological composition to provide the desired effect. The phrase "therapeutically effective amount" as used herein, e.g., of a synthetic modified RNA as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to, for example, effect a therapeutically or prophylatically significant reduction in a symptom or clinical marker associated with a cardiac dysfunction or disorder when administered to a typical subject who has a cardiovascular condition, disease or disorder.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

With reference to the treatment of, for example, a cardiovascular condition or disease in a subject, the term "therapeutically effective amount" refers to the amount that is safe and sufficient to prevent or delay the development or a cardiovascular disease or disorder. The amount can thus cure or cause the cardiovascular disease or disorder to go into remission, slow the course of cardiovascular disease progression, slow or inhibit a symptom of a cardiovascular disease or disorder, slow or inhibit the establishment of secondary symptoms of a cardiovascular disease or disorder or inhibit the development of a secondary symptom of a cardiovascular disease or disorder. The effective amount for the treatment of the cardiovascular disease or disorder depends on the type of cardiovascular disease to be treated, the severity of the symptoms, the subject being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of a cardiovascular disease or disorder as discussed herein, for example treatment of a rodent with acute myocardial infarction or ischemia-reperfusion injury, and any treatment or administration of the compositions or formulations that leads to a decrease of at least one symptom of the cardiovascular disease or disorder as disclosed herein, for example, increased heart ejection fraction, decreased rate of heart failure, decreased infarct size, decreased associated morbidity (pulmonary edema, renal failure, arrhythmias) improved exercise tolerance or other quality of life measures, and decreased mortality indicates effective treatment. In embodiments where the compositions are used for the treatment of a cardiovascular disease or disorder, the efficacy of the composition can be judged using an experimental animal model of cardiovascular disease, e.g., animal models of ischemia-reperfusion injury (Headrick J P, Am J Physiol Heart circ Physiol 285;H1797; 2003) and animal models acute myocardial infarction. (Yang Z, Am J Physiol Heart Circ. Physiol 282:H949: 2002; Guo Y, J Mol Cell Cardiol 33;825-830, 2001). When using an experimental animal model, efficacy of treatment is evidenced when a reduction in a symptom of the cardiovascular disease or disorder, for example, a reduction in one or more symptom of dyspnea, chest pain, palpitations, dizziness, syncope, edema, cyanosis, pallor, fatigue and high blood pressure which occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a treatment of a cardiovascular disease or disorder is used to refer to the reduction of a symptom and/or a biochemical marker of a cardiovascular disease or disorder, for example a reduction in at least one biochemical marker of a cardiovascular disease by at least about 10% would be considered an effective treatment. Examples of such biochemical markers of cardiovascular disease include a reduction of, for example, creatine phosphokinase (CPK), aspartate aminotransferase (AST), lactate dehydrogenase (LDH) in the blood, and/or a decrease in a symptom of cardiovascular disease and/or an improvement in blood flow and cardiac function as determined by someone of ordinary skill in the art as measured by electrocardiogram (ECG or EKG), or echocardiogram (heart ultrasound), Doppler ultrasound and nuclear medicine imaging. A reduction in a symptom of a cardiovascular disease by at least about 10% would also be considered effective treatment by the methods as disclosed herein. As alternative examples, a reduction in a symptom of cardiovascular disease, for example a reduction of at least one of the following; dyspnea, chest pain, palpitations, dizziness, syncope, edema, cyanosis etc. by at least about 10% or a cessation of such systems, or a reduction in the size one such symptom of a cardiovascular disease by at least about 10% would also be considered as affective treatments by the methods as disclosed herein. In some embodiments, it is preferred, but not required that the therapeutic agent actually eliminate the cardiovascular disease or disorder, rather just reduce a symptom to a manageable extent.

Subjects amenable to treatment by the methods as disclosed herein can be identified by any method to diagnose myocardial infarction (commonly referred to as a heart attack) or a cancer. Methods of diagnosing these conditions are well known by persons of ordinary skill in the art. By way of non-limiting example, myocardial infarction can be diagnosed by (i) blood tests to detect levels of creatine phosphokinase (CPK), aspartate aminotransferase (AST), lactate dehydrogenase (LDH) and other enzymes released during myocardial infarction; (ii) electrocardiogram (ECG or EKG) which is a graphic recordation of cardiac activity, either on paper or a computer monitor. An ECG can be beneficial in detecting disease and/or damage; (iii) echocardiogram (heart ultrasound) used to investigate congenital heart disease and assessing abnormalities of the heart wall, including functional abnormalities of the heart wall, valves and blood vessels; (iv) Doppler ultrasound can be used to measure blood flow across a heart valve; (v) nuclear medicine imaging (also referred to as radionuclide scanning in the art) allows visualization of the anatomy and function of an organ, and can be used to detect coronary artery disease, myocardial infarction, valve disease, heart transplant rejection, check the effectiveness of bypass surgery, or to select patients for angioplasty or coronary bypass graft.

The terms "coronary artery disease" and "acute coronary syndrome" as used interchangeably herein, and refer to myocardial infarction refer to a cardiovascular condition, disease or disorder, include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death.

As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. In some embodiments, pharmaceutical compositions can be specifically formulated for direct delivery to a target tissue or organ, for example, by direct injection or via catheter injection to a target tissue. In other embodiments, compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

As used herein, the terms "administering," "introducing" and "transplanting" are used interchangeably and refer to the placement of a pharmaceutical composition comprising at least one MOD-RNA, or a composition comprising a population of cells and at least one MOD-RNA, or a composition comprising a population of MOD-RNA transfected cardiomyocytes as described herein, into a subject by a method or route which results in at least partial localization of the pharmaceutical composition, at a desired site or tissue location. As used herein, the terms "administering," "introducing" and "transplanting" are used interchangeably and refer to the placement of a pharmaceutical composition comprising at least one MOD-RNA, or a composition comprising a population of cardiac cells and at least one MOD-RNA, or a composition comprising a population of MOD-RNA transfected cardiomyocytes as described herein, into a subject by a method or route which results in at least partial localization of the pharmaceutical composition, at a desired site or tissue location. In some embodiments, the pharmaceutical composition comprising MOD-RNA can be administered by any appropriate route which results in effective treatment in the subject, i.e. administration results in delivery to a desired location or tissue in the subject where at least a portion of the protein expressed by the MOD-RNA is located at a desired target tissue or target cell location.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration of pharmaceutical compositions comprising MOD-RNA other than directly into a target tissue or organ, such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations. In some embodiments, a pharmaceutical composition comprising a MOD-RNA can be in combination with one or more pharmaceutically acceptable ingredients. The carrier can be in the form of a solid, semi-solid or liquid diluent, cream or a capsule.

The term "drug" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally not present or not present at the levels being administered to a cell, tissue or subject. An agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The articles "a" and an are used herein to refer to one or to more than one (i.e., to at least one) of the grammatical object of the article. By way of example, "an element" means one element or more than one element.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Methods for In Vivo Protein Replacement Therapy

Synthetic, modified-RNAs as described herein can also be used to express a protein of interest therapeutically in a target tissue or organ by administration of a synthetic, modified-RNA composition to an individual or in alternative embodiments, by contacting cells with a synthetic, modified-RNA ex vivo, and then administering such cells to a subject. In one aspect, cells can be transfected with a modified RNA to express a therapeutic protein using an ex vivo approach in which cells are removed from a patient, transfected by e.g., electroporation or lipofection, and re-introduced to the patient. Continuous or prolonged administration in this manner can be achieved by electroporation of blood cells that are re-infused to the patient.

As disclosed herein, the inventors demonstrate a highly efficient and rapid protein expression in vivo after transfection of heart and muscle tissue with MOD-RNA. The inventors demonstrate that protein expression occurs by 3 hours or earlier after transfection, and that in vivo protein expression occurs for at least a 4-5 days after direct injection of the MOD-RNA into the muscle or heart. Importantly, the inventors demonstrate that the level of protein expression in vivo is dose-dependent on the amount of MOD-RNA injected into the heart or muscle in vivo, enabling one to titrate the amount of MOD-RNA administered to the tissue for the desired amount of protein to be expressed. Accordingly, the ability to titrate the amount of protein expressed is very useful where the synthetic modified RNAs are being used for in vivo protein expression in protein replacement therapy or other therapeutic methods.

As disclosed herein in the Examples, the transfection of heart tissue and muscle with MOD-RNA in vivo results in a low immunological response.

Accordingly, one aspect of the present invention relates to a method for expressing a protein in a tissue in vivo (e.g., a tissue in a subject), the method comprising contacting the tissue with a composition comprising a MOD-RNA encoding a protein of interest. In some embodiments, a tissue is any organ where it is desirable to have increased protein expression of a protein of interest.

The term "tissue" as used herein is a broad term that is applied to any group of cells that perform specific functions, and includes in some instances whole organs (e.g., parathyroid) and/or part of organs, such as pancreatic islets. A tissue need not form a layer, and thus encompasses a wide range of tissues including, muscle, heart, bone marrow, skin, connective tissue (e.g., cells that make up fibers in the framework supporting other body tissues); and hematopoietic and lymphoid tissue (e.g., cells which function as part of the body's immune system that helps protect it from bacteria and other foreign entities), pancreas, stomach, intestine, lung and the like.

In some embodiments, the target tissue which is contacted with MOD-RNA is muscle tissue, for example, cardiac muscle, or skeletal muscle or smooth muscle. In some embodiments, the tissue is heart tissue. In some embodiments, the tissues is vascularized tissue of the heart.

In some embodiments, the tissue is contacted with a composition comprising MOD-RNA encoding a protein of interest. The term "contacting" or "contact" as used herein as in connection with contacting a tissue with MOD-RNA as disclosed herein, includes touching or extremely close proximity of MOD-RNA with the tissue, organ or target cell population in vivo. Accordingly, in some embodiments, the phrase "contacting a tissue" or "contacting a cell population" refers to a method of exposure, which can be direct or indirect. In one method such contact comprises direct injection of the composition into the tissue through any means well known in the art, such as direct cardiac injection. In another embodiment, contacting also encompasses indirect contacting, such as via topical medium that surrounds the tissue, or administration to a subject, or via any route known in the art. In another embodiment, the term "contacting" means that the MOD-RNA molecule as disclosed herein is introduced into a subject receiving treatment, and the molecule is allowed to come in contact with the target tissue in vivo. Each possibility represents a separate embodiment of the present invention.

In some embodiments, the MOD-RNA is delivered to the tissue by direct injection of the tissue. As disclosed herein, direct injection of a composition comprising MOD-RNA into the heart resulted in robust protein expression from the MOD-RNA within about 3 days or less, and expression lasted for about 4-5 days.

In some embodiments, the MOD-RNA can be delivered to the tissue by any means known to persons of ordinary skill in the art, and include, for example, delivery by a catheter, which can be a permanent or temporary catheter to deliver the MOD-RNA composition to the target tissue. In some embodiments, the MOD-DNA is delivered using an endoscope. In some embodiments, for catheter and/or endoscope delivery, the catheter and/or endoscope can have a camera attachment, allowing imaging to assist the clinician in the accurate delivery of the composition comprising MOD-RNA to a desired tissue location.

In some embodiments, the composition comprising MOD-RNA as disclosed herein can be delivered to a target tissue using an implantable device. In some embodiments, the implantable device is a drug-delivery device, where the drug delivery device comprises a delivery catheter to deliver the MOD-RNA composition to the target tissue.

In some embodiments, a "drug delivery device," as used herein refers to delivery elements, e.g., delivery catheter to transport the pharmaceutical compositions comprising MOD-RNAs to the desired target tissue or target anatomy in the subject, e.g., the heart. In some embodiments, the drug delivery devices can comprise a "drug release module" or "controlled drug pump device," which refer to any implantable device suitable for the storage and controlled release of compositions comprising MOD-RNAs to the target area or target tissue according to the methods described herein. Use of such a "drug delivery device," allows the release of the composition comprising the MOD-RNA from the pump in a controlled manner (e.g., rate, timing of release), which is controlled by or determined by the device itself. The term "drug release module" also encompasses any implantable device with any mechanism of action including diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems. In some embodiments, the release of the composition comprising MOD-RNAs from the drug delivery device can be programmed, and in some embodiment the delivery device can be programmed using a remote control, which can be programmed by physician and/or the subject whom the implantable device is implanted in.

In alternative embodiments, a composition comprising MOD-RNA as disclosed herein can be delivered to a target tissue using an implantable device which is for the treatment of a particular disease or disorder. In some embodiments, the implantable device is a stent. For example, in some embodiments where the compositions comprising MOD-RNAs are used for the treatment of a cardiovascular disease or disorder, the MOD-RNA's can be used to coat a stent.

Cardiomyocytes and Myocyte Cells

In one embodiment of the invention relates to a method of treating a cardiovascular disease or disorder in a subject comprising administering an effective amount of a composition comprising at least one synthetic modified RNA (MOD-RNA) as disclosed herein to a subject with a cardiovascular disease or disorder.

The inventors demonstrate herein highly efficient protein expression in vivo in heart tissue as rapidly as 3 hours or less after direct injection of MOD-RNA expressing hVEGF into the heart or muscle tissue. The inventors demonstrate that protein expression lasts for at least a 4-5 days and results in a low immunological response as compared to non-modified RNA. As discussed previously, the inventors also demonstrate that the level of protein expression in vivo is dose-dependent on the amount of MOD-RNA injected into the heart or muscle in vivo, enabling one to titrate the amount of MOD-RNA administered to the tissue for the desired amount of protein expression required.

Accordingly, one aspect of the present invention relates to methods and compositions comprising a synthetic modified RNA to express a polypeptide in vivo in a tissue of a subject for the treatment of a disease or disorder. Another aspect of the present invention relate to methods to treat a disease or disorder in a subject comprising administering a composition comprising a synthetic modified RNA encoding a polypeptide of interest.

In some embodiments, the composition can be delivered to a specific tissue in the subject, and in some embodiments, the tissue is muscle tissue. In some embodiments, the muscle tissue can be skeletal muscle, cardiac muscle or smooth muscle.

In some embodiments, the methods as disclosed herein comprise delivering a synthetic modified RNA encoding a cardiac enhancing polypeptide to a muscle tissue in a subject for the treatment of one or more diseases, such as a cardiovascular disease. In some embodiments, a cardiovascular disease is, but is not limited to the following muscle diseases: cardiomyopathy (ischemic and non-ischemic), skeletal myopathy, cystic fibrosis, muscular dystrophy.

The inventors have demonstrated herein that the in vivo delivery a synthetic modified RNA encoding a hVEGF polypeptide to the heart of a mouse model of myocardial infarction prevented myocardial infarct from occurring and significantly prevented damage to the heart, as well as promoted recovery of the heart. Accordingly, in one embodiment, the methods as disclosed herein relate to a method of delivering a synthetic modified RNA encoding a cardiac enhancing polypeptide, e.g., VEGF to muscle tissue in a subject for the treatment heart attack and myocardial infarction. In some embodiments, the synthetic modified RNA encoding a cardiac enhancing peptide can be delivered to the myocardium via direct intramyocardial injection.

In some embodiments, for the treatment of a cardiovascular disease, the cardiac enhancing peptide expressed by the MOD-RNA is a polypeptide for enhancing vascularization of the heart and/or for revascularizing a heart after ischemia or cardiac infarction. In some embodiments, a cardiac enhancing peptide expressed by the MOD-RNA is VEGF, e.g., hVEGF.

The terms "enhance vascularization" as used herein refers to an increase or acceleration in the rate of formation of a vascularized network. In some embodiments, an enhanced vascularization refers to the formation of a more dense capillary or vascularized network as compared to in the absence of the method (e.g., the vascularization which would occur in the absence of administering a MOD-RNA encoding a cardiac enhancing polypeptide). Stated another way, an enhancement in vascularization refers to a statistically significant increase in the rate of formation of a vascularized network, or alternatively a statistically significant increase in the amount of capillary which form the vascularized network.

The terms "revascularize", "revascularizing", "neovascularization", or "revascularization" as used herein refer to improving or revising an existing vascular network or establishing a new functional or substantially functional vascular network in a tissue or organ that has an avascular or hypovascular zone, of an ischemic zone typically due to disease, congenital defect, or injury. Such an avascular or hypovascular tissue or organ is often totally or partially dysfunctional or has limited function and may be in need of revascularization. Revascularizing such a tissue or organ may result in restored or augmented function of the organ or tissue.

In some embodiments, the MOD-RNA can encode a fusion protein, for example, where VEGF is fused to a targeting protein to target VEGF to particular cells. In some embodiments, where it is desirable to have VEGF targeted to endothelial cells, the MOD-RNA can encode a VEGF-vWF fusion protein, where vWF serves as a homing peptide to target the VEGF to endothelial cells. Other targeting peptides and homing peptides are encompassed in the present invention.

In some instances, it is desirable to have a MOD-RNA encode a protein which is secreted. In such cases, the MOD-RNA encodes a protein comprising a secretory signal sequence that facilitates secretion of the protein. For example, if a MOD-RNA encodes a angiogenic protein as the protein of interest, a skilled artisan could either select an angiogenic protein with a native signal sequence, e.g. VEGF, or can modify the gene product to contain such a sequence using routine genetic manipulation (See Nabel et al., 1993).

Alternatively, in some embodiments, the MOD-RNA can be modified to have specific targeting moieties attached as disclosed herein, to target the MOD-RNA to particular cell types in the target tissue. In some embodiments, the moiety can be a targeting moiety directly attached to the MOD-RNA, or alternatively, an indirectly attached targeting moiety, for example, where the MOD-RNA is formulated in a liposome or nanoparticle, the surface of the liposome or nanoparticle can comprise targeting moieties for directing the MOD-RNA uptake by particular cells within the tissue.

In some embodiments, a cardiac enhancing peptide expressed by a MOD-RNA can be any cardiotrophic factors or growth factor to promote survival and/or growth of cardiac cells. Recently, it was reported that cardiac stem cells exist in a myocardial infarct after a heart attack, accordingly, one can administer a MOD-RNA encoding a cardiac enhancing peptide the heart for the treatment of myocardial infarction. Cardiotrophic factors are well known in the art and include but are not limited to cardiotrophic agents, creatine, carnitine, taurine, cardiotropic factors as disclosed in U.S. Patent Application Serial No. 2003/0022367 which is incorporated herein by reference, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway. Other cardiac enhancing peptides which can be expressed from MOD-RNA include cellular differentiation agents, such as cytokines and growth factors, as disclosed herein. Examples of various cell differentiation agents are disclosed in U.S. Patent Application Serial No. 2003/0022367 which is incorporated herein by reference, or Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001.

In an alternative embodiment, a synthetic modified RNAs as disclosed herein can be used to express a protein in order to enhance their ability to be involved in tissue regeneration, or to deliver a therapeutic protein to a site of administration. Of particular interest are synthetic modified RNAs as disclosed herein which encode a polypeptide which is a growth factor, for example, where the cell is a myogenic cell, e.g., a cardiomyocyte, a synthetic modified RNAs useful in the methods as disclosed herein can express one or more growth factors of various types, cardiotropic factors such as atrial natriuretic factor, cripto, and cardiac transcription regulation factors, such as GATA-4, Nkx2.5, and Mef2-C. Other examples of cytokines and growth factors which can be expressed by a MOD-RNA in the methods and compositions as disclosed herein include, but are not limited to, cardiotrophic agents, creatine, carnitine, taurine, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway.

Accordingly, in one embodiment, the invention provides a method for treating myocardial infarction, comprising administering a composition comprising at least one synthetic modified RNA (MOD-RNA) encoding a cardiac enhancing polypeptide to a subject having a myocardial infarction to the heart of a subject with, or having had a heart attack.

Additionally, while postnatal atrial myocytes are unable to proliferate, they can be reprogrammed to reexpress Isl1 and re-enter the cell cycle and proliferate. Such a method is disclosed in U.S. Application US2011/0003327 which is incorporated herein in its entirety by reference. Accordingly, in some embodiments, a composition comprising a MOD-RNA expressing Isl1 protein can be used to re-express Isl1 in atrial myocytes, which can then be induced to differentiate into vascular smooth muscle cells as well as ventricular myocytes by contacting with MOD-RNA expressing cardiotrophic growth factors. Accordingly, it is envisioned in the present invention to transduce atrial myocytes with Isl1 MOD RNA's and induce their proliferation and subsequent differentiation into ventricular myocytes. In addition, in some embodiments, the MOD-RNAs can express a protein which is used to promote cardiomyocyte proliferation, for example, any gene disclosed in Table 4.

As used herein, the term "Isl1" refers to the nucleic acid encoding Islet 1 gene and homologues thereof, including conservative substitutions, additions, deletions therein not adversely affecting the structure of function. Isl1 is referred in the art as Islet 1, ISL LIM homeobox 1 or Isl-1. Human Isl1 is encoded by nucleic acid corresponding to GenBank Accession No: BC031213 or NM_002202 and the human Isl1 corresponds to protein sequence corresponding to RefSeq ID No: AAH31213.

In some embodiments, the methods and compositions relate to use of MOD-RNA encoding a muscle protein the treatment of muscle diseases and disorders, for example for the treatment of muscular dystrophy. Muscular dystrophy represents a family of inherited diseases of the muscles. Some forms affect children (e.g., Duchenne dystrophy) and are lethal within two to three decades. Other forms present in adult life and are more slowly progressive. The genes for several dystrophies have been identified, including Duchenne dystrophy (caused by mutations in the dystrophin gene) and the teenage and adult onset Miyoshi dystrophy or its variant, limb girdle dystrophy 2B or LGMD-2B (caused by mutations in the dysferlin gene). These are "loss of function" mutations that prevent expression of the relevant protein in muscle and thereby cause muscle dysfunction. Mouse models for these mutations exist, either arising spontaneously in nature or generated by inactivation or deletion of the relevant genes. These models are useful for testing therapies that might replace the missing protein in muscle and restore normal muscle function.

In some embodiments, a composition comprising a synthetic modified RNA encoding one or more genes can be delivered to one or more muscle tissue targets. For example, in embodiments where the method is for the treatment of Duchenne/Becker Muscular Dystrophy, one can deliver a synthetic modified RNA encoding a non-mutated version of the Dystrophin protein can be delivered to one or more muscle tissue targets. For example, in embodiments where the method is for the treatment of Emery-Dreyfuss muscular dystrophy, one can deliver a synthetic modified RNA encoding Emerin and/or Lamin protein can be delivered to one or more muscle tissue targets.

In some embodiments, the methods and compositions relate to use of MOD-RNA encoding a muscle protein the treatment of muscle diseases and disorders, for example for the treatment of skeletal myopathy. In some embodiments, a composition comprising a synthetic modified RNA encoding the alpha-1 anti-trypsin protein can be delivered to one or more muscle tissue targets.

In some embodiments, the synthetic modified RNA encoding dystrophin and/or Emerin and/or Lamin protein can be delivered to the muscle tissue with the most marked disability associated with the condition, notably insufficient respiration due to a weakened thoracic diaphragm and inability to ambulate due to weak postural muscles. For diaphragmatic injection, one can use a thoracoscopic approach for the direct injection of a synthetic modified RNA encoding dystrophin and/or Emerin and/or Lamin protein into the muscle diaphragm. In some embodiments, one can deliver a synthetic modified RNA encoding dystrophin directly by injection into skeletal muscles, for example, direct injection into a pelvic girdle and shoulder girdle muscles associated with maintenance of posture and gross arm movements, respectively.

Another embodiments of the invention further provides for a method of treating an injured tissue in a subject comprising: (a) determining a site of tissue injury in the subject; and (b) administering a composition comprising at least one synthetic modified RNA (MOD-RNA) into and around the site of tissue injury, wherein the composition comprising at least one synthetic modified RNA (MOD-RNA) expresses a protein beneficial to the treatment of the injured tissue. In one embodiment, the tissue is heart tissue or cardiac muscle. In a further embodiment, the tissue injury is a myocardial infarction, cardiomyopathy or congenital heart disease. In some embodiments, the tissue is skin and the injured tissue is wound healing. In such an embodiment where the tissue is skin, a composition comprising a MOD-RNA can be administered topically to the skin.

In some embodiments, a composition comprising a synthetic modified RNA encoding one or more genes listed in Table 1, 2, 3, 4, 5, and 6 can be delivered to one or more target tissues in a subject for protein expression in vivo. In some embodiments, the target tissue is muscle tissue, and in some embodiments, the muscle tissue is cardiac muscle tissue, skeletal tissue or smooth muscle tissue.

TABLE 1

Examples of genes encoded by a synthetic modified RNA for protein expression in a target tissue in vivo in a subject.

| Protein encoded by MOD-RNA for expression in vivo | mRNA sequence ID | SEQ ID NO | Transcript Variants SEQ ID NO |
|---|---|---|---|
| VEGF | NM_001025366 | 001 | 95-99 and 140-151 |
| activin A | NM_001105 | 002 | 152 |
| activin B | NM_002193.2 | 351 | N/A |
| insulin-like growth factor (IGF1) | NM_000618 | 003 | 153-155 |
| bone morphogenic protein | NM_006132 | 004 | 156-157 |
| fibroblast growth factor | NM_000800 | 005 | 158-162 |
| platelet-derived growth factor | NM_002607 | 006 | 163 |
| insulin, leukemia inhibitory factor (LIF) | NM_002309 | 007 | N/A |
| epidermal growth factor (EGF) | NM_001178130 | 008 | 164-165 |
| TGFalpha | NM_001099691 | 009 | 166 |
| TDGF1 | NM_003212 | 010 | 167 |
| vWF | NM_000552 | 011 | N/A |
| GATA-4 | NM_002052 | 012 | N/A |
| Nkx2.5 | NM_001166175 | 013 | 168-169 |
| Mef2-C | NM_002397 | 014 | 170-174 |
| LGMD-2B; limb girdle dystrophy 2B (Dysferlin) | NM_003494 | 015 | 175-187 |
| Dystrophin (DMD) | NM_004006 | 016 | 188-204 |
| Emerin (EMD) | NM_000117 | 017 | N/A |
| Lamin A/C | NM_170707 | 018 | 205-206 |
| alpha-1 anti-trypsin (A1AT) | NM_001002235 | 019 | 207-216 |
| CFTR | NM_000492 | 020 | N/A |
| ANG | NM_001097577 | 021 | 217 |
| Presenilin (PSEN2) | NM_000447 | 022 | 218 |
| Isl1 | NM_002202 | 023 | N/A |

In some embodiments, the methods and compositions comprising at least one synthetic modified RNA (MOD-RNA) can be use to treat circulatory disorder is selected from the group consisting of cardiomyopathy, myocardial infarction, and congenital heart disease. In some embodiments, the cardiovascular disease or disorder is a myocardial infarction. In some embodiments, the compositions comprising at least one synthetic modified RNA (MOD-RNA) are contacted with tissue, e.g., heart tissue which has a myocardial infarct, where the expression of the protein in vivo treats myocardial infarction by reducing the size of the myocardial infarct. It is also contemplated that a composition comprising at least one synthetic modified RNA (MOD-RNA) expressing a cardiac enhancing protein in vivo can be used to treat myocardial infarction by reducing the size of the scar resulting from the myocardial infarct. In some embodiments, the invention contemplates that a composition comprising at least one synthetic modified RNA (MOD-RNA) is administered directly to heart tissue of a subject, or is administered systemically.

In some embodiments, the methods and compositions comprising at least one synthetic modified RNA (MOD-RNA) can be used to treat a circulatory disorder is selected from the group consisting of cardiomyopathy, myocardial infarction, and congenital heart disease, for example, the MOD-RNA can express any or a combination of MOD-RNA to treat heart failure, as disclosed in Table 2, or to promote vascularogenesis, for example, the genes disclosed in Table 3.

TABLE 2

Additional exemplary examples of genes encoded by a synthetic modified RNA for in vivo protein expression in a target tissue in a subject for the treatment of heart failure.
MOD-RNA genes for treatment of HEART FAILURE:

| Protein encoded by MOD-RNA for expression in vivo | mRNA sequence ID | SEQ ID NO | Transcript Variants SEQ ID NO |
|---|---|---|---|
| SERCA 1a (ATP2A1) | NM_004320 | 001 | 219 |
| SERCA2a (ATP2A2) | NM_001681 | 002 | 220 |
| Phospholamban (PLN) | NM_002667 | 003 | N/A |
| βARK (ADRBK1, GRK2, BARK1) | NM_001619 | 004 | N/A |
| beta-adrenergic receptor (ADRB1) | NM_000684 | 005 | N/A |
| Akt (AKT1) | NM_005163 | 006 | 221-222 |
| adenylyl cyclase VI (ADCY6) | NM_020983 | 007 | 223 |

TABLE 3

Additional exemplary examples of genes encoded by a synthetic modified RNA for in vivo protein expression in a target tissue in a subject for the treatment of heart failure.
Genes encoded by MOD-RNA to promote VASCULOGENESIS:

| Protein encoded by MOD-RNA for expression in vivo | mRNA sequence ID NO | SEQ ID NO | Transcript Variants SEQ ID NO |
|---|---|---|---|
| VEGF (VEGFA) | NM_001025366 | 001 | 224-240 |
| FGF 1 | NM_000800 | 002 | 241-245 |
| FGF 2 (FGFB) | NM_002006 | 003 | N/A |
| FGF 4 | NM_002007 | 004 | N/A |
| FGF 5 | NM_004464 | 005 | 246 |
| HGF | NM_000601 | 006 | 247-250 |
| Ang1 (ANGPT1; angiopoietin1) | NM_001146, NM_139290 | 007 352 | 251 353-354 |
| MGP1 (Matrix Gla Protein) | NM_000900 | 008 | 252 |
| OMG (oligodendrocyte myelin glycoprotein) | NM_002544 | 009 | N/A |
| G-CSF (CSF3; Colony Stimulating Factor 3) | NM_172220 | 010 | 253-255 |
| PDGF (PDGFA) | NM_002607 | 011 | 256 |
| IGF1 | NM_000618 | 012 | 257-259 |
| IGF2 | NM_000612 | 013 | 260-261 |
| EGR1 | NM_001964 | 014 | N/A |
| Prax1 (benzodiazapine receptor associated protein 1; BZRAP1; PRAX-1, KIAA0612) | NM_004758 | 015 | 262 |

In some embodiments, the present invention is also directed to a method of treating a cardiovascular disease or disorder in a subject where there is damage in the heart or peripheral vasculature which occurs as a consequence of genetic defect, physical injury, environmental insult or damage from a stroke, heart attack or cardiovascular disease (most often due to ischemia) in a subject, the method comprising administering to the subject a composition comprising at least one synthetic modified RNA (MOD-RNA) for expression of an effective amount of a cardiac enhancing polypeptide in vivo in the heart of the subject. Medical indications for such treatment include treatment of acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

In some embodiments, the effects of administrating a composition comprising at least one synthetic modified RNA (MOD-RNA) encoding a cardiac enhancing polypeptide can be demonstrated by, but not limited to, one of the following clinical measures: increased heart ejection fraction, decreased rate of heart failure, decreased infarct size, decreased associated morbidity (pulmonary edema, renal failure, arrhythmias) improved exercise tolerance or other quality of life measures, and decreased mortality. The effects of protein expression of a cardiac enhancing polypeptide can be evident over the course of days to weeks after beginning administration of regimen of dosages of the composition, however, as protein expression in vivo can be detected as early as 3 hours after administration in vivo, beneficial effects of expression of the expressed cardiac enhancing protein may be observed as early as several hours after the first administration, and may persist for at least several days, months to several years.

In some embodiments, a composition comprising at least one synthetic modified RNA (MOD-RNA) expressing a cardiac enhancing protein in vivo can be delivered to the heart using a special device, which are available and adapted for administering compositions directly to the chambers of the heart, the pericardium, or the interior of the cardiac muscle at the desired location. The compositions as disclosed herein can be administered to a recipient's heart by intracoronary injection, e.g. into the coronary circulation. In alternative embodiments, a composition comprising at least one synthetic modified RNA (MOD-RNA) expressing a cardiac enhancing protein in vivo can also be administered by intramuscular injection into the wall of the heart.

In some embodiments, a composition comprising MOD-RNAs for in vivo protein expression of a protein of interest, e.g., a cardiac enhancing protein in the heart can be administered by injection into the heart, e.g., direct injection into the ventricular wall of the heart.

In some embodiments, a composition comprising MOD-RNAs for in vivo protein expression of a protein of interest, e.g., a cardiac enhancing protein in the heart can be used to treat circulatory damage in the heart or peripheral vasculature which occurs as a consequence of genetic defect, physical injury, environmental insult or damage from a stroke, heart attack or cardiovascular disease (most often due to ischemia) in a subject, the method comprising administering (including transplanting), a composition comprising MOD-RNAs for in vivo protein expression of a protein of interest, e.g., a cardiac enhancing protein in the heart to a subject. Medical indications for such treatment include treatment of acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

In some embodiments, the effects of a composition comprising MOD-RNAs for in vivo protein expression of a protein of interest, e.g., a cardiac enhancing protein in the heart could be demonstrated by, but not limited to, one of the following clinical measures: increased heart ejection fraction, decreased rate of heart failure, decreased infarct size, decreased associated morbidity (pulmonary edema, renal failure, arrhythmias) improved exercise tolerance or other quality of life measures, and decreased mortality. The effects of a composition comprising MOD-RNAs for in vivo protein expression of a protein of interest, e.g., a cardiac enhancing protein in the heart can be evident over the course of days to weeks after the procedure. However, beneficial effects may be observed as early as several hours after the procedure, and may persist for several years.

In some embodiments, the compositions comprising a MOD-RNA encoding a cardiac enhancing protein can be used to modify a myogenic cell ex vivo, which can be transplanted into a subject, and in some embodiments, can be transplanted into a subject in the presence of at least one other MOD-RNA encoding a cardiac enhancing protein. In some embodiments, the synthetic modified RNAs as disclosed herein can be used to modify a cell, e.g., a myogenic cell, e.g., a cardiomyocyte, e.g., to replace a gene product, or to facilitate regeneration of cardiac tissue, to treat disease, or to improve survival of the myogenic cell after injury or following implantation of the myogenic cell into a subject (i.e. prevent rejection).

In another embodiment, the methods and compositions and kits as disclosed herein for in vivo protein expression using synthetic modified RNAs can be used in regenerative medicine strategies as well. For example, in some embodiments, a composition comprising at least one synthetic modified RNA encoding a protein of interest can also comprise a population of cells of interest. Stated another way, in some embodiments, the present invention provides methods for regenerative cell therapy comprising administering to the subject a combination of at least one synthetic modified RNAs with a population of cells of interest. Accordingly, composition comprising at least one synthetic modified RNA encoding a protein of interest and a population of cells of interest cells may be used for tissue reconstitution or regeneration in a human patient or other subject in need of such treatment. The compositions comprising MOD-RNA and cells can be administered in a manner that permits them to graft or migrate to the intended tissue site and reconstitute or regenerate the functionally deficient area.

In some embodiments, the methods and compositions and kits as disclosed herein for in vivo protein expression using synthetic modified RNAs which are administered in combination with a cell for tissue regeneration can be any MOD-RNA encoding a protein which promotes cardiomyocyte proliferation and/or survival, for example, such genes include but are not listed to those genes listed in Table 4 as disclosed herein.

TABLE 4

Exemplary examples of genes encoded by a synthetic modified RNA for in vivo protein expression in a target tissue in a subject for the treatment of heart failure or to promote cardiomyocyte proliferation. Genes encoded by MOD-RNAs to promote CARDIOMYOCYTE PROLIFERATION:

| Protein encoded by MOD-RNA for expression in vivo | mRNA sequence ID | SEQ ID NO | Transcript Variants SEQ ID NO |
| --- | --- | --- | --- |
| Neuregulin 1 (NRG1, GGF) | NM_001159995 | 001 | 263-278 |
| ErbB4 (ERBB4) | NM_001042599 | 002 | 279 |
| Periostin (POSTN) | NM_006475 | 003 | 280-282 |
| HAND1 | NM_004821 | 004 | N/A |
| E2F4 | NM_001950 | 005 | N/A |
| Skp2 | NM_005983 | 006 | 283-284 |
| Akt1 | NM_005163 | 007 | 285-286 |

Treatment of Other Loss of Function Diseases.

In some embodiments, the methods, compositions and kits as disclosed herein for in vivo protein expression using synthetic modified RNAs can be used in method for the treatment of loss-of-function diseases. A loss-of-function disease is a disease associated with a mutation in a gene which causes a reduced or abolished protein function.

In some embodiments, the loss of function genes are tumor suppressor genes, or mutations in genes responsible for DNA repair, cell division cycle checkpoints, cell motility, transcriptional regulation, and apoptosis. Loss-of-function" as used herein refers to a reduction or elimination of the normal activity of a gene or gene product. Loss of activity can be due to a decrease in transcription and/or processing of the RNA, a decrease in translation, stability, transport, or activity of the gene product, or any combination thereof. Tumor-suppressor genes and genes suspected of being tumor-suppressor genes include, but are not limited to, BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB1, MEN, NF2/SCH, PTCH, TGFBR1, TGFBR2, ACVR1B, AVCR2, MRE11, MAP2K4, and LKB1/STK11.

In some embodiments, the methods, compositions and kits as disclosed herein can be used for in vivo protein expression in a tissue in a subject using synthetic modified RNAs encoding any of the genes listed in Tables 5-7, as disclosed herein. In some embodiments, the methods, compositions and kits as disclosed herein can be used for in vivo protein expression in a tissue in a subject using synthetic modified RNAs encoding any of the genes listed in Tables 5 for the treatment of arrhythmia.

In some embodiments, the methods, compositions and kits as disclosed herein can be used for in vivo protein expression in a tissue in a subject using synthetic modified RNAs encoding any of the genes listed in Tables 6 for the treatment of myopathy.

In some embodiments, the methods, compositions and kits as disclosed herein can be used for in vivo protein expression in a tissue in a subject using synthetic modified RNAs encoding any of the genes listed in Tables 7 for the treatment of liposomal storage diseases in a subject.

TABLE 5

Exemplary examples of genes encoded by a synthetic modified RNA for in vivo protein expression in a target tissue in a subject for the treatment of arrhythmia.
Genes encoded by MOD-RNAs to treat ARRHYTHMIA:

| Protein encoded by MOD-RNA for expression in vivo | mRNA sequence ID | SEQ ID NO | Transcript Variants SEQ ID NO |
|---|---|---|---|
| HERG (LQT2, short QT - Ikr, Kv11.1; KCNH2) | NM_000238 | 001 | 287-289 |
| KCNQ1 (LQT - Iks; KCNA9) | NM_000218 | 002 | N/A |
| SCN5A (LQT3, Brugada) | NM_198056 | 003 | 290-294 |
| ANK2 (Ankyrin B; LQT4) | NM_001148 | 004 | 295-296 |
| KCNE1 (LQT5; MinK, ISK, JLNS2) | NM_000219 | 005 | 297-299 |
| KCNE2 (LQT6; MiRP1) | NM_172201 | 006 | N/A |
| KCNJ2 (LQT7, short QT; Kir2.1, IRK1) | NM_000891 | 007 | N/A |
| CACNA1c (LQT8, Brugada; Cav1.2, CACH2, CACN2, TS) | NM_000719 | 008 | 300-321 |
| SCN4B (LQT10) | NM_001142348 | 009 | 322-323 |
| SERCA (CPVT; APT2A1) | NM_004320 | 010 | 324 |
| KCNQ2 (short QT; Kv7.2, ENB1, BFNC, KCNA11, HNSPC) | NM_172109 | 011 | 325-328 |
| SCN1B (Brugada) | NM_001037 | 012 | 329 |
| KCNE3 (Brugada; MiRP2, HOKPP) | NM_005472 | 013 | N/A |

TABLE 6

Exemplary examples of genes encoded by a synthetic modified RNA for in vivo protein expression in a target tissue in a subject for the treatment of myopathy.
Genes encoded by MOD-RNAs to treat MYOPATHY:

| Protein encoded by MOD-RNA for expression in vivo | mRNA sequence ID | SEQ ID NO | Transcript Variants SEQ ID NO |
|---|---|---|---|
| Nebulin (NEB) (Nemaline myopathy) | NM_004543 | 001 | 330-331 |
| MTM1 (myotubularin 1) (X-linked myotubular myopathy) | NM_000252 | 002 | N/A |
| Lamin A/C (LMNA; LMN1; PRO1; LMNL1) | NM_170707 | 003 | 332-333 |
| Emerin (EMD) | NM_000117 | 004 | N/A |
| Desmin (DES; CMD1I, CSM1, CSM2) | NM_001927 | 005 | N/A |
| Delta-sarcoglycan (SGCD; DAGD, LGMD2F, CMD1L) | NM_000337 | 006 | 334-335 |

TABLE 7

Exemplary examples of genes encoded by a synthetic modified RNA for in vivo protein expression in a target tissue in a subject for the treatment of liposomal storage diseases and disorders.
Genes encoded by MOD-RNAs to treat LIPOSOMAL STORAGE DISEASES.

| Protein encoded by MOD-RNA for expression in vivo | mRNA sequence ID | SEQ ID NO | Transcript Variants SEQ ID NO |
|---|---|---|---|
| GAA (acid alpha-glucosidase) (Pompe disease) | NM_000152 | 001 | 336-337 |
| HEXA (hexaminidase A) (Tay Sachs disease) | NM_000520 | 002 | N/A |
| HEXB (hexaminidase B)(Sandhoff disease) | NM_000521 | 003 | N/A |
| Beta-glucosidase (Lysomal glucocerebrosidase; GBA1) (Gaucher's Disease) | NM_000157 | 004 | 338-341 |
| SMPD1 (Niemann-Pick's disease Type A and B) | NM_000543 | 005 | 342 |
| NPC2 (Niemann-Pick disease, type C2) | NM_006432 | 006 | N/A |
| NPC1 (Niemann-Pick disease, type C1) | NM_000271 | 007 | N/A |
| GNPTG (Mucolipidosis disease or ML) | NM_032520 | 008 | N/A |
| Cathepsin A (CTSA) (Galactosialidosis disease) | NM_000308 | 009 | 343-344 |
| iduronate 2-sulfatase (IDS; I2S; MPS2; SIDS) (Hunters Syndrome) | NM_000202 | 010 | 345-346 |
| IDUA (Hurlers Disease) | NM_000203 | 011 | N/A |
| SLC17A5 (Salla disease or SD), | NM_012434 | 012 | N/A |
| GLA (Fabry's disease) | NM_000169 | 013 | N/A |
| GALC (Krabbe's disease) | NM_001201401 | 014 | 347-348 |
| ECM1 (Urbach-Wiethe disease) | NM_004425 | 015 | 349-350 |

In another embodiment, the methods, compositions and kits as disclosed herein for in vivo protein expression using synthetic modified RNAs can be used in a method the treatment of cystic fibrosis. In some embodiments, one can deliver a synthetic modified RNA encoding the non-mutated (wild-type) CFTR protein to the diaphragm of the subject. In some embodiments, a synthetic modified RNA encoding CFTR can be delivered by direct parenchymal injection and/or intrabronchial introduction of modified RNA that directs expression of non-mutated CFTR. Any means to deliver a synthetic modified RNA encoding a desired polypeptide for the treatment of a disease or disorder is encompassed herein, and for example, direct bowel and pancreas injections, via laparoscopic and endoscopic approaches, respectively, can be used for the treatment of subjects with disorders associated with these organ systems.

ANG, encoding a 14 kDa angiogenic ribonuclease, is a loss-of-function gene identified in ALS. Accordingly, in another embodiment, a composition comprising at least one MOD-RNA expressing the ANG polypeptide can be used to express ANG protein in the muscle for the treatment of ALS. In some embodiments, one can deliver a synthetic modified RNA encoding the ANG protein to muscles of a subject diagnosed with ALS.

Treatment of other loss of function diseases are encompassed in the methods of the present invention, and include partial loss of function diseases. For example, one may administer a composition comprising a MOD-RNA encoding a presenilin protein for the treatment of Alzheimer's disease in a subject.

Loss of function diseases include, α-thalassemia, β-thalassemia, Turner Syndrome, Retinoblastoma In some embodiments, the methods as disclosed herein comprise delivering a synthetic modified RNA encoding a polypeptide of interest to a tissue in a subject for the treatment of one or more diseases, where the synthetic modified RNA is delivered by an implantable device, e.g., a drug-delivery device such as a drug-delivery pump, or alternatively, using a flexible injection catheter that would facilitate multiple muscle injections from a single entry point. In some embodiments, a synthetic modified RNA encoding a polypeptide of interest is delivered to a tissue in a subject on the exterior of an implantable device, e.g., the synthetic modified RNA encoding a polypeptide of interest is coated on the outside of an implantable device. In some embodiments, where the disease to be treated is a cardiac disease or disorder as disclosed herein, a synthetic modified RNA encoding a polypeptide of interest is coated on an stent.

In some embodiments, the methods, compositions and kits as disclosed herein for in vivo protein expression using synthetic modified RNAs can be used in method for the treatment of skin disorders, e.g., skin pigment disorders. In such an embodiment, topical administration of a composition comprising a synthetic modified RNA encoding a protein of interest can be used in the treatment of a skin disorder and/or skin pigment disorder. In some embodiments, the methods relate to in vivo protein expression using synthetic modified RNAs encode a protein for the treatment of vitiligo. In some embodiments, a skin disorder is eczema (often associated with loss of function of filaggrin gene), or albinism, e.g., Hermansky-Pudlak syndrome (associated with mutations in HPS1 and HPS3 genes, among others), Incontinentia pigmenti (associated with mutations in the IKBKG gene), Oculocutaneous albinism (associated with mutations in one or more of MC1R, OCA2, SLC45A2, TYR, SLC45A2 and TYRP1 genes), Waardenburg syndrome (associated with mutations in EDN3, EDNRB, MITF, PAX3, SNAI2, and SOX10 genes), and Xeroderma pigmentosum (associated with mutations in ERCC2, ERCC3, POLH, XPA, and XPC genes). Accordingly, the present invention relates to treatment of such disorders by in vivo expression of a protein associated with the skin disorder, where the protein expression occurs by topical application of a MOD-RNA encoding one or more proteins associated with the skin disorder.

Treatment of Cancers

Many tumors, particularly adenocarcinomas, are characterized by an outer layer of stromal cells (desmoplastic tissue) which is resistant to the delivery of chemotherapeutic agents. By reducing the amount of desmoplastic tissue, reducing the rate of growth of a desmoplastic tissue, and/or decreasing the degree to which desmoplastic tissue is refractory to a chemotherapeutic agent can allow a chemotherapeutic agents to penetrate the tumor more effectively, enhancing efficacy and potentially lowering the necessary dosage. Described herein are methods of altering desmoplastic tissue in two ways to increase the efficacy of a chemotherapeutic agent. In some embodiments, the degree of vascularization of the desmoplastic tissue is increased, providing more opportunities for a chemotherapeutic agent to reach the entire volume of a tumor. In some embodiments, the amount of desmoplastic tissue or the rate of growth of desmoplastic tissue is decreased by inhibiting Hedgehog signaling, which has been implicated in the proliferation of desmoplastic tissue. Synthetic, modified-RNAs as described herein can be used (i) to express a polypeptide which enhances neovascularization in the desmoplastic tissue of a tumor in a subject and/or (ii) as inhibitors of the expression of a polypeptide which enhances Hedgehog signaling in a target tumor; by administration of a synthetic, modified-RNA composition to an individual or in alternative embodiments, by contacting the tumor with the synthetic, modified-RNA. In some embodiments cells are contacted with a synthetic, modified-RNA ex vivo, and then administered to a subject. In one aspect, cells can be transfected with a modified RNA to express a therapeutic protein using an ex vivo approach in which cells are removed from a patient, transfected by e.g., electroporation or lipofection, and re-introduced to the patient. Continuous or prolonged administration in this manner can be achieved by electroporation of blood cells that are re-infused to the patient.

As disclosed herein, the inventors demonstrate a highly efficient and rapid protein expression in vivo after transfection of various tissues with MOD-RNA. The inventors demonstrate that protein expression occurs by 3 hours or earlier after transfection, and that in vivo protein expression occurs for at least a 4-5 days after direct injection of the MOD-RNA into the tissues. Importantly, the inventors demonstrate that the level of protein expression in vivo is dose-dependent on the amount of MOD-RNA injected into tissue in vivo, enabling one to titrate the amount of MOD-RNA administered to the tissue for the desired amount of protein to be expressed. Accordingly, the ability to titrate the amount of protein expressed is very useful where the synthetic modified RNAs are being used for in vivo protein expression in therapeutic methods.

As disclosed herein in the Examples, the transfection of tissues with MOD-RNA in vivo results in a low immunological response.

Accordingly, one aspect of the invention described herein relates to a method for expressing a polypeptide in a tumor in vivo (e.g. a tumor in a subject), the method comprising administering a composition comprising a synthetic, modified RNA molecule encoding a polypeptide which enhances neovascularization in the subject, wherein the resulting neovascularization increases the effectiveness of a chemotherapeutic agent administered to the subject. In some embodiments, the tumor is contacted with MOD-RNA or a composition comprising MOD-RNA. In some embodiments, the chemotherapeutic agent is administered concurrently with the MOD-RNA. In some embodiments, a composition comprising both a chemotherapeutic agent and a MOD-RNA encoding a polypeptide which enhances neovascularization.

The polypeptide which enhances neovascularization can be any polypeptide, variant, or functional fragment thereof which causes an increase in vascularization in a tissue contacted with the polypeptide. Exemplary polypeptides which enhance neovascularization are listed in Table 3 herein. In some embodiments, the polypeptide which enhances neovascularization is a VEGF polypeptide. In some embodiments, the VEGF polypeptide is a human VEGF polypeptide.

One aspect of the invention described herein relates to a method for treating a tumor by inhibiting the expression of a polypeptide which enhances Hedgehog signaling in the tumor of a subject, the method comprising administering a composition comprising a synthetic, modified RNA molecule anti-sense inhibitor of the expression of a polypeptide which enhances Hedgehog signaling to a subject, wherein the inhibition of Hedgehog signaling results in a decrease of desmoplastic tissue or a decrease in the growth of desmoplastic tissue, thereby increasing the effectiveness of a chemotherapeutic agent administered to the subject. In some embodiments, the tumor is contacted with MOD-RNA or a composition comprising MOD-RNA. In some embodiments, the chemotherapeutic agent is administered concurrently with the MOD-RNA. In some embodiments, a composition comprising both a chemotherapeutic agent and a MOD-RNA encoding a polypeptide which enhances neovascularization.

The term "Hedgehog signaling pathway", "Hedgehog pathway" and "Hedgehog signal transduction pathway" are all used to refer to the chain of events normally mediated by Hedgehog, smoothened, Ptch1, and Gli, among others, and resulting in a changes in gene expression and other phenotypic changes typical of Hedgehog activity. Activating a downstream component can activate the Hedgehog pathway even in the absence of a Hedgehog protein. For example, overexpression of smoothened will activate the pathway in the absence of Hedgehog, Gli and Ptch1 gene expression are indicators of an active Hedgehog-signaling pathway. Accordingly, compounds described herein can be used to reduce the level of Hedgehog signaling.

The polypeptide which enhances Hedgehog signaling can be any polypeptide which, when active, increases the signaling propagated by the Hedgehog signaling pathway; or which is a downstream target of Hedgehog signaling; or which increases the expression or activity of a member of the Hedgehog signaling pathway. In some embodiments, the polypeptide which enhances Hedgehog signaling can be Hedgehog (SHH; NCBI Ref Seq; NP_000184; SEQ ID NO:087); Smoothened (Smo; NCBI Ref Seq; NP_005622; SEQ ID NO:088); Patched (PTCH1; NCBI Ref Seq; NP_000255; SEQ ID NO:089) or Gli (NCBI Ref Seq; NP_001153517; SEQ ID NO:090). In some embodiments, the polypeptide which enhances Hedgehog signaling can be a human polypeptide.

While not wishing to be bound by any particular theory, it is noted that Ptch1 may not signal directly into the cell, but rather modulates the activity of smoothened, another membrane bound protein located downstream of Ptch1 in Hedgehog signaling (Marigo et al., (1996) Nature 384: 177-179; Taipale et al. (2002) Nature 418, 892-896). The gene smo is a segment polarity gene required for the correct patterning of every segment in *Drosophila* (Alcedo et al., (1996) Cell 86:221232). Human homologs of smo have been identified. See, for example, Stone et al. (1996) Nature 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. Ptc is a Hh receptor. Cells that express Smo fail to bind Hh, indicating that smo does not interact directly with Hh (Nusse, (1996) Nature 384: 119120). Rather, the binding of Sonic Hedgehog (SHH) to its receptor, PTCH. is thought to prevent normal inhibition by PTCH of smoothened. Activating smoothened mutations are known to occur in sporadic basal cell carcinoma (Xie, et al., Nature, 1998, 391: 90-92), and in primitive neuroectodermal tumors of the central nervous system (Reifenberger, et al., Cancer Res., 1998, 58:1798-1803).

The vertebrate family of Hedgehog genes includes three members that exist in mammals, known as Desert (Dhh), Sonic (Shh) and Indian (Ihh) Hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is processed to a repressor form and nuclear accumulation of activator forms prevented prevented through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself. Increased levels of Hedgehog signaling can contribute to the growth of desmoplastic tissue associated with a tumor.

In some embodiments, a MOD-RNA which inhibits the expression of a polypeptide which enhances Hedgehog signaling is a "gene silencing" agent (e.g. an RNAi molecule). A gene silencing agent comprises a nucleic acid sequence, modified nucleic acid sequence, or arrangement of nucleic acid analogs which is complementary to and binds to a target mRNA and thereby inhibits the expression of mRNA of a target gene. As used herein, "gene silencing" or "gene silenced" in reference to an activity of a nucleic acid agent (e.g. a gene silencing agent), refers to a decrease in the mRNA level in a cell for a target gene by at least about 5%, about 10%, about 20%, about 30%, about 40%, about 50%, about 60%, about 70%, about 80%, about 90%, about 95%, about 99% or more of the mRNA level found in the cell without the presence of the gene silencing agent. In one preferred embodiment, the mRNA levels are decreased by at least about 70%, about 80%, about 90%, about 95%, about 99% or more. In some embodiments, a gene silencing agent can be an antisense oligonucleotide. It is possible to synthesize a strand of nucleic acid (DNA, RNA or a chemical analogue) that will bind to the messenger RNA (mRNA) produced by a target gene and inactivate it, effectively turning that gene "off". This is because mRNA has to be single stranded for it to be translated. This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

In some embodiments, a gene silencing agent can be an RNA interference-inducing molecule (RNAi), including an anti-sense oligonucleotide and modified versions thereof, where the RNAi agent silences the gene expression of the target gene. Examples of RNAi molecules include, but are not limited to, dsRNA, shRNAi, siRNA, micro RNAi (mRNAi), antisense oligonucleotides etc. Additional sequences can also be present. As used herein, the term "RNAi" refers to a phenomenon where an agent for causing RNAi, such as double-stranded RNA (dsRNA) causes the specific degradation of homolgous mRNA, thus suppressing the expression of gene products (see Coburn, G. and Cullen, B. (2002) J. of Virology 76:9225). This process has been described in plants, invertebrates, and mammalian cells. RNAi can be caused by any type of interfering RNA, including but are not limited to, siRNA, shRNA, endogenous microRNA and artificial microRNA.

An RNAi agent can be substantially homologous to the target gene (e.g. Hedgehog) or genomic sequence, or a fragment thereof. As used in this context, the term "homologous" is defined as being substantially identical, sufficiently complementary, or similar to the target mRNA, or a fragment thereof, to effect RNA interference of the target gene. In addition to native RNA molecules, RNAs suitable for inhibiting or interfering with the expression of target gene include RNA derivatives and analogs.

In some embodiments, the RNAi agent can be substantially homologous to the target mRNA or a fragment thereof. By way of non-limiting example, the RNAi can be substantially homologous to mRNAs expressed from the following genes, or fragments thereof: Hedgehog (e.g. NCBI Ref Seq; NP_000193; SEQ ID NO:091); Smoothened (e.g. NCBI Ref Seq; NP_005631; SEQ ID NO:092); Patched (e.g. NCBI Ref Seq; NP_000264; SEQ ID NO:093) or Gli (e.g. NCBI Ref Seq; NP_001160045; SEQ ID NO:094). In some embodiments, the polypeptide which enhances Hedgehog signaling can be a human polypeptide.

In some embodiments, single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs.

In some embodiments, the RNAi molecule is a dsRNA. Double-stranded RNA (dsRNA) has been shown to trigger degradation of single-stranded RNA (ssRNA) targets complementary to the dsRNA trigger (Fire A, 1999, Trends Genet 15:358-363). RNA interference (RNAi) effects triggered by dsRNA have been demonstrated in a number of organisms including plants, protozoa, nematodes, and insects (Cogoni C. and Macino G, 2000, Curr Opin Genet Dev 10:638-643).

In some embodiments, the RNAi molecule is a small interfereing RNA (siRNA). siRNAs mediate post-transcriptional gene-silencing, and can be used to induce RNAi in mammalian cells. siRNA-dependent post-transcriptional silencing of gene expression involves cutting the target messenger RNA molecule at a site guided by the siRNA. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. The siRNA molecules can also comprise a 3' hydroxyl group. The siRNA molecules can be single-stranded or double stranded; such molecules can be blunt ended or comprise overhanging ends (e.g., 5', 3'). In some embodiments, siRNA sequences are chosen to by scanning for sequences that have the lowest free energy of binding at the 5'-terminus of the antisense strand. Preferably the siRNA is capable of promoting RNA interference through degradation or specific post-transcriptional gene silencing (PTGS) of the target messenger RNA (mRNA).

In one embodiment, the 3' overhangs can be stabilized against degradation. By way of non-limiting example, RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April;9(4):493-501, incorporated by reference herein in its entirety).

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Where the gene silencing agent is an antisense oligonucleotide or RNAi agent, the region of the agent with homology to the target sequence can be selected from a given target gene sequence, e.g., the coding sequence of Hedgehog, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. Methods of predicting and selecting antisense oligonucleotides and RNAi agents are known in the art and are also found at the GENSCRIPT, AMBION, DHARMACON, OLIGOENGINE websites and described in U.S. Pat. No. 6,060,248.

By way of non-limiting example, one method of designing a siRNA molecule of the present invention involves identifying the 23 nucleotide sequence motif AA(N19)TT (SEQ ID NO: 355) (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif.

The gene silencing agent preferably targets only one sequence. Each of the gene silencing agents, such as siR-NAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, as few as 11 contiguous nucleotides of sequence identity are sufficient to direct silencing of non-targeted transcripts. Therefore, one can initially screen the proposed gene silencing agents to avoid potential off-target silencing using the sequence identity analysis by any known sequence comparison methods, such as BLAST.

In some embodiments, assessment of the expression and/or knock down of the target gene using gene specific gene silencing agents can be determined by methods that are well known in the art, such as western blot analysis or enzyme activity assays. Other methods can be readily prepared by those of skill in the art based on the known sequence of the target mRNA.

The methods and compositions described herein are useful in the treatment of solid tumors, soft tissue tumors, and metastases thereof. In some embodiments, the chemotherapeutic agent is administered after the MOD-RNA. As used herein, a "tumor" refers to a tissue mass that is undergoing uncontrolled proliferation. A tumor can be a cancerous tumor. In some embodiments, the tumor is a malignancy (e.g., sarcoma, adenocarcinoma, or carcinoma) of one of the various organ systems, such as those of lung, breast, lymphoid, gastrointestinal (e.g., colon), and genitourinary (e.g., renal, urothelial, or testicular tumors) tracts, pancrease, pharynx, prostate, and ovary. In some embodiments, the tumor can be a tumor having a stromal layer. In some embodiments, the cancer is non-small cell lung cancer. In some embodiments, the cancer is an adenocarcinoma. In some embodiments, the cancer is pancreatic ductal adenocarcinoma (PDAC). Examples of adenocarcinomas include, but are not limited to colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

As used herein a "chemotherapeutic agent" refers to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

In some embodiments, the chemotherapeutic agent is a cytotoxic chemotherapeutic. The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

In some embodiments, the chemotherapeutic is gemcitabine. "Gemcitabine" or "2'-deoxy-2',2'-difluorocytidine monohydrochloride (b-isomer)" is a nucleoside analogue that exhibits antitumor activity. Gemcitabine HCl is sold by Eli Lilly under the trademark GEMZAR™. In some embodiments, the chemotherapeutic agent can be gemcitabine; fluorouracil, capecitabine; ciplastin; irinotecan; oxaliplatin; 5-fluorouracil; folinic acid; or erlotinib. In some embodiments, two or more chemotherapeutic agents can be administered, e.g. two agents, three agents or more agents. Multiple chemotherapeutic agents can be administered separately or concurrently. Non-limiting examples of chemotherapeutics which can be used in the methods described herein include cisplatin, doxorubicin, irinotecan (CPT11), paclitaxel, 5-fluorouracil (5-FU), capecitabine (XELODA™), 6-mercaptopurine, bevacizumab, methotrexate. 6-thioguanine, pemetrexed, raltitrexed, arabinosylcytosine ARA-C cytarabine (CYTOSAR-U®), dacarbazine (DTIC-DOME@), azocytosine, deoxycytosine, pyridmidene, fludarabine (FLUDARA®), cladrabine, and 2-deoxy-D-glucose. Further non-limiting examples of chemotherapeutic agents include of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CBI-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g. calicheamicin, especially calicheamicin gammall and calicheamicin omegall (see, e.g., Agnew. *Chem. Intl. Ed. Engl.,* 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, detorubicin, 6-diazo-5-oxoL-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX®), TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSKS polysaccharide complex (JHS Natural Products, Eugene, Oreg.); razoxane; rhizoxin; sizofiran; spirogermanium; tenuazonic acid; triaziquone; 2,2',2"trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophorfree, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluoromethylomifhine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

In some embodiments, the MOD-RNA is delivered to the tissue by direct injection of the tumor. As disclosed herein, direct injection of a composition comprising MOD-RNA into a tissue can result in robust protein expression from the MOD-RNA within about 3 days or less, and expression can last for about 4-5 days.

In some embodiments, the MOD-RNA can be delivered to the tissue (e.g. the tumor) by any means known to persons of ordinary skill in the art, and include, for example, delivery by a catheter, which can be a permanent or temporary catheter to deliver the MOD-RNA composition to the target tissue. In some embodiments, the MOD-DNA is delivered using an endoscope. In some embodiments, for catheter and/or endoscope delivery, the catheter and/or endoscope can have a camera attachment, allowing imaging to assist the clinician in the accurate delivery of the composition comprising MOD-RNA to a desired tissue location.

In some embodiments, the composition comprising MOD-RNA as disclosed herein can be delivered to a target tissue using an implantable device. In some embodiments, the implantable device is a drug-delivery device, where the drug delivery device comprises a delivery catheter to deliver the MOD-RNA composition to the target tissue.

In some embodiments, the MOD-RNA can encode a fusion protein, for example, where VEGF is fused to a targeting protein to target VEGF to particular cells. In some embodiments, where it is desirable to have VEGF targeted to endothelial cells, the MOD-RNA can encode a VEGF-vWF fusion protein, where vWF serves as a homing peptide to target the VEGF to endothelial cells. Other targeting peptides and homing peptides are encompassed in the present invention.

In some instances, it is desirable to have a MOD-RNA encode a protein which is secreted. In such cases, the MOD-RNA encodes a protein comprising a secretory signal sequence that facilitates secretion of the protein. For example, if a MOD-RNA encodes an angiogenic protein as the protein of interest, a skilled artisan could either select an angiogenic protein with a native signal sequence, e.g. VEGF, or can modify the gene product to contain such a sequence using routine genetic manipulation (See Nabel et al., 1993).

Alternatively, in some embodiments, the MOD-RNA can be modified to have specific targeting moieties attached as disclosed herein, to target the MOD-RNA to particular cell types in the target tissue. In some embodiments, the moiety can be a targeting moiety directly attached to the MOD-RNA, or alternatively, an indirectly attached targeting moiety, for example, where the MOD-RNA is formulated in a liposome or nanoparticle, the surface of the liposome or nanoparticle can comprise targeting moieties for directing the MOD-RNA uptake by particular cells within the tissue.

In some embodiments, the methods and compositions described herein relate to the treatment of a tumor. Medical indications for such treatment include a diagnosis of cancer. Methods of diagnosing cancers are well known to medical practitioners of ordinary skill in the art. By way of non-limiting example, PDAC is characterized by symptoms which can include painless jaundice, epigastric pain which radiates to the back, weight loss, nausea, and pruritus; A diagnosis can be made based upon examinations which include, for example, abdominal palpitations, ultrasound, detection of increased levels of serological markers for PDAC (e.g. CA19-9), and/or histological examination of biopsies or resections from the subject as described, e.g. in Bortesi et al. Surgical Pathology 2011 4; which is incorporated by reference herein in its entirety. Efficacy of treatment can be monitored by clinically accepted criteria, such as reduction in volume of the tumor, reduction in the growth of the tumor, or a reduction of metastasis or tumor growth as compared to a subject not receiving treatment according to the methods described herein.

In some embodiments, the effects of administrating a composition comprising at least one synthetic modified RNA (MOD-RNA) for the treatment of a tumor can be demonstrated by, but not limited to, one of the following measures: increased neovascularization or a reduction in desmoplastic tissue or the rate of growth of desmoplastic tissue of a tumor. Neovascularization can be determined by gross inspection and H&E staining, e.g. in a mouse model of cancer. The effect on desmoplastic tissue or the rate of growth of desmoplastic tissue of a tumor can be determined histologically.

In some embodiments, the methods of administering a MOD-RNA to treat cancer in a subject as described herein can used to treat a subject who is also being treated using a palliative debulking or surgical therapy. In some embodiments, the MOD-RNA is administered during the debulking or surgical therapy. In some embodiments, the MOD-RNA is administered after the debulking or surgical therapy.

Doses of MOD-RNAs Administered to a Subject

In some embodiments, one can deliver an effective amount of a composition comprising a MOD-RNA encoding a protein or agent of interest to the desired tissue in vivo. In some embodiments, various dosage ranges of the MOD-RNAs if the present invention are encompassed. In some embodiments, the MOD-RNA is delivered at a concentration of more than (e.g., greater than) 100 ng/µl. In some embodiments, the concentration of a MOD-RNA in a composition delivered to a tissue in vivo is about at least 0.5 µg/µl, or at least about 1 µg/µl, or at least about 2 µg/µl, or at least about 3 µg/µl, or at least about 4 µg/µl, or at least about 5 µg/µl, or at least about 6 µg/µl, or at least about 7 µg/µl, or at least about 8 µg/µl, or at least about 9 µg/µl, or at least about 10 µg/µl, or at least about 12 µg/µl, or at least about 14 µg/µl, or at least about 16 µg/µl, or at least about 18 µg/µl, or at least about 20 µg/µl, or at least about 25 µg/µl, or at least about 30 µg/µl, or at least about 40 µg/µl, or at least about 50 µg/µl, or any concentration integer between about 0.5 µg/µl and 25 µg/µl. In some embodiments, the concentration of a MOD-RNA in a composition delivered to a tissue in vivo is greater than 50 µg/µl, and can be at least about 60 µg/µl, or at least about 70 µg/µl, or at least about 80 µg/µl, or at least about 90 µg/µl, or at least about 100 µg/µl (0.1 mg/ml) or more than 100 µg/µl.

In some embodiments, a dosage of MOD-RNA in a composition administered to a tissue in vivo is about 50 µg, or about 100 µg, or about 200 µg, or about 300 µg, or about 400 µg, or about 500 µg, or about 600 µg, or about 700 µg, or about 800 µg, or about 900 µg, or about 1 mg, or any amount between about 50 µg and 1 mg or MOD-RNA. In some embodiments, a dosage of MOD-RNA in a composition administered to a tissue in vivo is about 100 µg/kg body weight, or about 100 µg/kg body weight, or about 200 µg/kg body weight, or about 300 µg/kg body weight, or about 400 µg/kg body weight, or about 500 µg/kg body weight, or about 600 µg/kg body weight or about 0.7 mg/kg body weight or about 0.8 mg/kg body weight or about 0.9 mg/kg body weight or about 1 mg/kg body weight.

In some embodiments, a dosage of MOD-RNA in a composition administered to a tissue in vivo is about 100 µg/kg tissue weight (e.g., the tissue to which the MOD-RNA is being delivered to), or about 100 µg/kg, or about 200 µg/kg, or about 300 µg/kg, or about 400 µg/kg, or about 500 µg/kg, or about 600 µg/kg, or about 0.7 mg/kg or about 0.8 mg/kg, or about 0.9 mg/kg, or about 1 mg/kg tissue weight.

In some embodiments, the frequency of the dosages delivered to a tissue is determined by the in vivo half-life of the MOD-RNA. In some embodiments, the half-life is about 48 hours in vivo, so the frequency of administration of a composition comprising a MOD-RNA can be every day, or in some embodiment every other day. In some embodiments, as the protein expression from the MOD-RNA in vivo can last for about 4-5 days, in some embodiments, the frequency of administration of a composition comprising a MOD-RNA can be every 4 days, or every 5 days, or weekly or every 10 days or every 2 weeks. In some embodiments, the frequency of administration is every month.

In one embodiment, the dose of a MOD-RNA in a composition administered to a tissue in vivo in the range of 10-100 µg/day. In another embodiment, the dosage is about 50-200 µg/day. In another embodiment, the dosage is 50-200 µg/day. In some embodiments, the dosage is about 100 µg/day.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose. As described below, in another embodiment, an advantage of MOD-RNA as disclosed herein is their greater potency in vivo than non-modified RNA, enabling the use of smaller doses.

Additionally, in some embodiments, a doses of a composition comprising MOD-RNAs comprise a plurality of MOD-RNA, e.g., at least two, or at least about 3, or at least about 4, or at least about 5, or at least about 5, or at least about 6, or at least about 7, or at least about 8, or at least about 9, or at least about 10, different MOD-RNA's to express a plurality of different proteins and/or agents in vivo in a tissue at the same. In some embodiments, where a composition comprises at more than one MOD-RNA and a tissue expresses at least one of the encoded proteins in vivo, the tissue can also express at least one, all or any combination, of other proteins from the different MOD-RNAs.

Synthetic Modified RNAs Expressing Polypeptides

Described herein are methods for protein expression in vivo in a tissue, e.g., in a heart tissue, or a cardiomyocyte by contacting a population of heart cells, e.g., cardiomyocytes with a composition comprising at least one synthetic modified RNA (MOD-RNA) encoding a polypeptide.

Synthetic modified RNA's for use in the compositions, methods and kits as disclosed herein are described in U.S. Provisional Application 61/387,220, filed Sep. 28, 2010, and U.S. Provisional Application 61/325,003, filed: Apr. 16, 2010, both of which are incorporated herein in their entirety by reference.

As used herein, the term "synthetic, modified RNA" (also referred herein as MOD-RNA) refers to a nucleic acid molecule encoding a factor, such as a polypeptide, to be expressed in a host cell, which comprises at least one modified nucleoside and has at least the following characteristics as the term is used herein: (i) it can be generated by in vitro transcription and is not isolated from a cell; (ii) it is translatable in vivo in a mammalian (and preferably human) cell; and (iii) it does not provoke or provokes a significantly reduced innate immune response or interferon response in a cell to which it is introduced or contacted relative to a synthetic, non-modified RNA of the same sequence. A synthetic, modified-RNA as described herein permits repeated transfections in a target cell or tissue in vivo; that is, a cell or cell population transfected in vivo with a synthetic, modified-RNA molecule as described herein tolerates repeated transfection with such synthetic, modified-RNA without significant induction of an innate immune response or interferon response. These three primary criteria for a synthetic, modified RNA molecule described above are described in greater detail below.

First, the synthetic, modified-RNA must be able to be generated by in vitro transcription of a DNA template. Methods for generating templates are well known to those of skill in the art using standard molecular cloning techniques. An additional approach to the assembly of DNA templates that does not rely upon the presence of restriction endonuclease cleavage sites is also described herein (termed "splint-mediated ligation"). The transcribed, synthetic, modified-RNA polymer can be modified further post-transcription, e.g., by adding a cap or other functional group.

To be suitable for in vitro transcription, the modified nucleoside(s) must be recognized as substrates by at least one RNA polymerase enzyme expressed by the tissue or cell which is transfected with the MOD-RNA. Generally, RNA polymerase enzymes can tolerate a range of nucleoside base modifications, at least in part because the naturally occurring G, A, U, and C nucleoside bases differ from each other quite significantly. Thus, the structure of a modified nucleoside base for use in generating the synthetic, modified-RNAs described herein can generally vary more than the sugar-phosphate moieties of the modified nucleoside. That said, ribose and phosphate-modified nucleosides or nucleoside analogs are known in the art that permit transcription by RNA polymerases. In some embodiments of the aspects described herein, the RNA polymerase is a phage RNA polymerase. The modified nucleotides pseudouridine, m5U, s2U, m6A, and m5C are known to be compatible with transcription using phage RNA polymerases, while N1-methylguanosine, N1-methyladenosine, N7-methylguanosine, 2'-)-methyluridine, and 2'-O-methylcytidine are not. Polymerases that accept modified nucleosides are known to those of skill in the art.

It is also contemplated that modified polymerases can be used to generate synthetic, modified-RNAs, as described herein. Thus, for example, a polymerase that tolerates or accepts a particular modified nucleoside as a substrate can be used to generate a synthetic, modified-RNA including that modified nucleoside.

Second, the synthetic, modified-RNA must be translatable in vivo by the translation machinery of a eukaryotic, preferably mammalian, and more preferably, human cell in vivo. Translation in vivo generally requires at least a ribosome binding site, a methionine start codon, and an open reading frame encoding a polypeptide. Preferably, the synthetic, modified-RNA also comprises a 5' cap, a stop codon, a Kozak sequence, and a polyA tail. In addition, mRNAs in a eukaryotic cell are regulated by degradation, thus a synthetic, modified-RNA as described herein can be further modified to extend its half-life in the cell by incorporating modifications to reduce the rate of RNA degradation (e.g., by increasing serum stability of a synthetic, modified-RNA).

Nucleoside modifications can interfere with translation. To the extent that a given modification interferes with translation, those modifications are not encompassed by the synthetic, modified-RNA as described herein. One can test a synthetic, modified-RNA for its ability to undergo translation and translation efficiency using an in vivo translation assay (e.g., using a MOD-RNA encoding a cre recombinase gene in an in vivo mouse cre model assay, or MOD-RNA encoding luciferase and detecting expression in vivo using a bioluminescence assay of the translated protein) and detecting the amount of the polypeptide produced using SDS-PAGE, Western blot, or immunochemistry, bioluminescence assays etc. The translation of a synthetic, modified-RNA comprising a candidate modification is compared to the translation of an RNA lacking the candidate modification, such that if the translation of the synthetic, modified-RNA having the candidate modification remains the same or is increased then the candidate modification is contemplated for use with the compositions and methods described herein. It is noted that fluoro-modified nucleosides are generally not translatable and can be used herein as a negative control for an in vitro translation assay.

Third, the synthetic, modified-RNA provokes a reduced (or absent) innate immune response in vivo or reduced interferon response in vivo by the transfected tissue or cell population. mRNA produced in eukaryotic cells, e.g., mammalian or human cells, is heavily modified, the modifications permitting the cell to detect RNA not produced by that cell. The cell responds by shutting down translation or otherwise initiating an innate immune or interferon response. Thus, to the extent that an exogenously added RNA can be modified to mimic the modifications occurring in the endogenous RNAs produced by a target cell, the exogenous RNA can avoid at least part of the target cell's defense against foreign nucleic acids. Thus, in some embodiments, synthetic, modified-RNAs as described herein include in vitro transcribed RNAs including modifications as found in eukaryotic/mammalian/human RNA in vivo. Other modifications that mimic such naturally occurring modifications can also be helpful in producing a synthetic, modified-RNA molecule that will be tolerated by a cell. With this as a background or threshold understanding for the requirements of a synthetic, modified-RNA, the various modifications contemplated or useful in the synthetic, modified-RNAs described herein are discussed further herein below.

RNA Modifications

In some aspects, provided herein are synthetic, modified RNA molecules (MOD-RNAs) encoding polypeptides or which are themselves anti-sense inhibitory agents, wherein the synthetic, modified RNA molecules comprise one or more modifications, such that introducing the synthetic, modified RNA molecules to a cell or tissue in vivo results in a reduced innate immune response of the tissue in vivo relative to a cell contacted with synthetic RNA molecules encoding the polypeptides not comprising said one or more modifications.

The synthetic, modified-RNAs as described herein include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50% or more in translation relative to the lack of the modification—e.g., in a rabbit reticulocyte in vitro translation assay), the modification is not suitable for the methods and compositions described herein. Specific examples of synthetic, modified-RNA compositions useful with the methods described herein include, but are not limited to, RNA molecules containing modified or non-natural internucleoside linkages. Synthetic, modified-RNAs having modified internucleoside linkages include, among others, those that do not have a phosphorus atom in the internucleoside linkage. In other embodiments, the synthetic, modified-RNA has a phosphorus atom in its internucleoside linkage(s).

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39,464, each of which is herein incorporated by reference in its entirety.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of modified oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, each of which is herein incorporated by reference in its entirety.

Some embodiments of the synthetic, modified-RNAs described herein include nucleic acids with phosphorothioate internucleoside linkages and oligonucleosides with heteroatom internucleoside linkage, and in particular —CH2-NH—CH2-, —CH2-N(CH3)-O—CH2-[known as a methylene (methylimino) or MMI], —CH2-O—N(CH3)-CH2-, —CH2-N(CH3)-N(CH3)-CH2- and —N(CH3)-CH2-CH2-[wherein the native phosphodiester internucleoside linkage is represented as —O—P—O—CH2-] of the above-referenced U.S. Pat. No. 5,489,677, and the amide backbones of the above-referenced U.S. Pat. No. 5,602,240, both of which are herein incorporated by reference in their entirety. In some embodiments, the nucleic acid sequences featured herein have morpholino backbone structures of the above-referenced U.S. Pat. No. 5,034,506, herein incorporated by reference in its entirety.

Synthetic, modified-RNAs described herein can also contain one or more substituted sugar moieties. The nucleic acids featured herein can include one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C1 to C10 alkyl or C2 to C10 alkenyl and alkynyl. Exemplary modifications include O[(CH2)nO]mCH3, O(CH2).nOCH3, O(CH2)nNH2, O(CH2)nCH3, O(CH2)nONH2, and O(CH2)nON[(CH2)

nCH3)]2, where n and m are from 1 to about 10. In some embodiments, synthetic, modified-RNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, a reporter group, an intercalator, a group for improving the pharmacokinetic properties of an RNA, or a group for improving the pharmacodynamic properties of a synthetic, modified-RNA, and other substituents having similar properties. In some embodiments, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid sequence, particularly the 3' position of the sugar on the 3' terminal nucleotide or in 2'-5' linked nucleotides and the 5' position of 5' terminal nucleotide. A synthetic, modified-RNA can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

As non-limiting examples, synthetic, modified-RNAs described herein can include at least one modified nucleoside including a 2'-O-methyl modified nucleoside, a nucleoside comprising a 5' phosphorothioate group, a 2'-amino-modified nucleoside, 2'-alkyl-modified nucleoside, morpholino nucleoside, a phosphoramidate or a non-natural base comprising nucleoside, or any combination thereof.

In some embodiments of this aspect and all other such aspects described herein, the at least one modified nucleoside is selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxyuridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

Alternatively, a synthetic, modified-RNA can comprise at least two modified nucleosides, at least 3, at least 4, at least 5, at least 6, at least 7, at least 8, at least 9, at least 10, at least 15, at least 20 or more, up to the entire length of the oligonucleotide. At a minimum, a synthetic, modified-RNA molecule comprising at least one modified nucleoside comprises a single nucleoside with a modification as described herein. It is not necessary for all positions in a given synthetic, modified-RNA to be uniformly modified, and in fact more than one of the aforementioned modifications can be incorporated in a single synthetic, modified-RNA or even at a single nucleoside within a synthetic, modified-RNA. However, it is preferred, but not absolutely necessary, that each occurrence of a given nucleoside in a molecule is modified (e.g., each cytosine is a modified cytosine e.g., 5mC). However, it is also contemplated that different occurrences of the same nucleoside can be modified in a different way in a given synthetic, modified-RNA molecule (e.g., some cytosines modified as 5mC, others modified as 2'-O-methylcytidine or other cytosine analog). The modifications need not be the same for each of a plurality of modified nucleosides in a synthetic, modified-RNA. Furthermore, in some embodiments of the aspects described herein, a synthetic, modified-RNA comprises at least two different modified nucleosides. In some such preferred embodiments of the aspects described herein, the at least two different modified nucleosides are 5-methylcytidine and pseudouridine. A synthetic, modified-RNA can also contain a mixture of both modified and unmodified nucleosides.

As used herein, "unmodified" or "natural" nucleosides or nucleobases include the purine bases adenine (A) and guanine (G), and the pyrimidine bases thymine (T), cytosine (C) and uracil (U). In some embodiments, a synthetic, modified-RNA comprises at least one nucleoside ("base") modification or substitution. Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl)adenine, 2 (amino)adenine, 2-(aminoalkyll)adenine, 2 (aminopropyl) adenine, 2 (methylthio) N6 (isopentenyl)adenine, 6 (alkyl) adenine, 6 (methyl)adenine, 7 (deaza)adenine, 8 (alkenyl) adenine, 8-(alkyl)adenine, 8 (alkynyl)adenine, 8 (amino) adenine, 8-(halo)adenine, 8-(hydroxyl)adenine, 8 (thioalkyl) adenine, 8-(thiol)adenine, N6-(isopentyl)adenine, N6 (methyl)adenine, N6, N6 (dimethyl)adenine, 2-(alkyl)guanine, 2 (propyl)guanine, 6-(alkyl)guanine, 6 (methyl)guanine, 7 (alkyl)guanine, 7 (methyl)guanine, 7 (deaza)guanine, 8 (alkyl)guanine, 8-(alkenyl)guanine, 8 (alkynyl)guanine, 8-(amino)guanine, 8 (halo)guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl) cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl)uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio)pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio)pseudouracil, 1 (aminocarbonylethylenyl)-pseudouracil, 1 (aminocarbonylethylenyl)-2(thio)- pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylamino-carbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, N2-substituted purines, N6-substituted purines, O6-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Modified nucleosides also include natural bases that comprise conjugated moieties, e.g. a ligand. As discussed herein above, the RNA containing the modified nucleosides must be translatable in a host cell (i.e., does not prevent translation of the polypeptide encoded by the modified RNA). For example, transcripts containing s2U and m6A are translated poorly in rabbit reticulocyte lysates, while pseudouridine, m5U, and m5C are compatible with efficient translation. In addition, it is known in the art that 2'-fluoro-modified bases useful for increasing nuclease resistance of a transcript, leads to very inefficient translation. Translation can be assayed by one of ordinary skill in the art using e.g., a rabbit reticulocyte lysate translation assay.

Further modified nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in Int. Appl. No. PCT/US09/038,425, filed Mar. 26, 2009; those disclosed in The Concise Encyclopedia Of Polymer Science And Engineering, pages 858-859, Kroschwitz, J. L., ed. John Wiley & Sons, 1990, and those disclosed by Englisch et al., Angewandte Chemie, International Edition, 1991, 30, 613.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety, and U.S. Pat. No. 5,750,692, also herein incorporated by reference in its entirety.

Another modification for use with the synthetic, modified-RNAs described herein involves chemically linking to the RNA one or more ligands, moieties or conjugates that enhance the activity, cellular distribution or cellular uptake of the RNA. Ligands can be particularly useful where, for example, a synthetic, modified-RNA is administered in vivo. Such moieties include but are not limited to lipid moieties such as a cholesterol moiety (Letsinger et al., Proc. Natl. Acid. Sci. USA, 1989, 86: 6553-6556, herein incorporated by reference in its entirety), cholic acid (Manoharan et al., Biorg. Med. Chem. Let., 1994, 4:1053-1060, herein incorporated by reference in its entirety), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770, each of which is herein incorporated by reference in its entirety), a thiocholesterol (Oberhauser et al., Nucl. Acids Res., 1992, 20:533-538, herein incorporated by reference in its entirety), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54, each of which is herein incorporated by reference in its entirety), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783, each of which is herein incorporated by reference in its entirety), a polyamine or a polyethylene glycol chain (Manoharan et al., Nucleosides & Nucleotides, 1995, 14:969-973, herein incorporated by reference in its entirety), or adamantane acetic acid (Manoharan et al., Tetrahedron Lett., 1995, 36:3651-3654, herein incorporated by reference in its entirety), a palmityl moiety (Mishra et al., Biochim. Biophys. Acta, 1995, 1264:229-237, herein incorporated by reference in its entirety), or an octadecylamine or hexylamino-carbonyloxycholesterol moiety (Crooke et al., J. Pharmacol. Exp. Ther., 1996, 277:923-937, herein incorporated by reference in its entirety).

The synthetic, modified-RNAs described herein can further comprise a 5' cap. In some embodiments of the aspects described herein, the synthetic, modified-RNAs comprise a 5' cap comprising a modified guanine nucleotide that is linked to the 5' end of an RNA molecule using a 5'-5' triphosphate linkage. As used herein, the term "5' cap" is also intended to encompass other 5' cap analogs including, e.g., 5' diguanosine cap, tetraphosphate cap analogs having a methylene-bis(phosphonate) moiety (see e.g., Rydzik, A M et al., (2009) *Org Biomol Chem* 7(22):4763-76), dinucleotide cap analogs having a phosphorothioate modification (see e.g., Kowalska, J. et al., (2008) *RNA* 14(6):1119-1131), cap analogs having a sulfur substitution for a non-bridging oxygen (see e.g., Grudzien-Nogalska, E. et al., (2007) *RNA* 13(10): 1745-1755), N7-benzylated dinucleoside tetraphosphate analogs (see e.g., Grudzien, E. et al., (2004) *RNA* 10(9):1479-1487), or anti-reverse cap analogs (see e.g., Jemielity, J. et al., (2003) *RNA* 9(9): 1108-1122 and Stepinski, J. et al., (2001) *RNA* 7(10):1486-1495). In one such embodiment, the 5' cap analog is a 5' diguanosine cap. In some embodiments, the synthetic, modified RNA does not comprise a 5' triphosphate.

The 5' cap is important for recognition and attachment of an mRNA to a ribosome to initiate translation. The 5' cap also protects the synthetic, modified-RNA from 5' exonuclease mediated degradation. It is not an absolute requirement that a synthetic, modified-RNA comprise a 5' cap, and thus in other embodiments the synthetic, modified-RNAs lack a 5' cap. However, due to the longer half-life of synthetic, modified-RNAs comprising a 5' cap and the increased efficiency of translation, synthetic, modified-RNAs comprising a 5' cap are preferred herein.

The synthetic, modified-RNAs described herein can further comprise a 5' and/or 3' untranslated region (UTR). Untranslated regions are regions of the RNA before the start codon (5') and after the stop codon (3'), and are therefore not translated by the translation machinery. Modification of an RNA molecule with one or more untranslated regions can improve the stability of an mRNA, since the untranslated regions can interfere with ribonucleases and other proteins involved in RNA degradation. In addition, modification of an RNA with a 5' and/or 3' untranslated region can enhance translational efficiency by binding proteins that alter ribosome binding to an mRNA. Modification of an RNA with a 3' UTR can be used to maintain a cytoplasmic localization of the RNA, permitting translation to occur in the cytoplasm of the cell. In one embodiment, the synthetic, modified-RNAs described herein do not comprise a 5' or 3' UTR. In another embodiment, the synthetic, modified-RNAs comprise either a 5' or 3' UTR. In another embodiment, the synthetic, modified-RNAs described herein comprise both a 5' and a 3'UTR. In one embodiment, the 5' and/or 3' UTR is selected from an mRNA known to have high stability in the cell (e.g., a murine alpha-globin 3' UTR). In some embodiments, the 5' UTR, the 3' UTR, or both comprise one or more modified nucleosides.

In some embodiments, the synthetic, modified-RNAs described herein further comprise a Kozak sequence. The "Kozak sequence" refers to a sequence on eukaryotic mRNA having the consensus (gcc)gccRccAUGG, where R is a purine (adenine or guanine) three bases upstream of the start codon (AUG), which is followed by another 'G'. The Kozak consensus sequence is recognized by the ribosome to initiate translation of a polypeptide. Typically, initiation occurs at the first AUG codon encountered by the translation machinery that is proximal to the 5' end of the transcript. However, in some cases, this AUG codon can be bypassed in a process called leaky scanning The presence of a Kozak sequence near the AUG codon will strengthen that codon as the initiating site of translation, such that translation of the correct polypeptide occurs. Furthermore, addition of a Kozak sequence to a synthetic, modified-RNA will promote more efficient translation, even if there is no ambiguity regarding the start codon. Thus, in some embodiments, the synthetic, modified-RNAs described herein further comprise a Kozak consensus sequence at the desired site for initiation of translation to produce the correct length polypeptide. In some such embodiments, the Kozak sequence comprises one or more modified nucleosides.

In some embodiments, the synthetic, modified-RNAs described herein further comprise a "poly (A) tail", which refers to a 3' homopolymeric tail of adenine nucleotides, which can vary in length (e.g., at least 5 adenine nucleotides) and can be up to several hundred adenine nucleotides). The inclusion of a 3' poly(A) tail can protect the synthetic, modified-RNA from degradation in the cell, and also facilitates extra-nuclear localization to enhance translation efficiency. In some embodiments, the poly(A) tail comprises between 1 and 500 adenine nucleotides; in other embodiments the poly(A) tail comprises at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 325, at least 350, at least 375, at least 400, at least 425, at least 450, at least 475, at least 500 adenine nucleotides or more. In one embodiment, the poly(A) tail comprises between 1 and 150 adenine nucleotides. In another embodiment, the poly(A) tail comprises between 90 and 120 adenine nucleotides. In some such embodiments, the poly(A) tail comprises one or more modified nucleosides.

It is contemplated that one or more modifications to the synthetic, modified-RNAs described herein permit greater stability of the synthetic, modified-RNA in a cell or tissue in vivo. To the extent that such modifications permit translation and either reduce or do not exacerbate a cell's innate immune or interferon response to the synthetic, modified-RNA with the modification, such modifications are specifically contemplated for use herein. Generally, the greater the stability of a synthetic, modified-RNA, the more protein can be produced from that synthetic, modified-RNA. Typically, the presence of AU-rich regions in mammalian mRNAs tend to destabilize transcripts, as cellular proteins are recruited to AU-rich regions to stimulate removal of the poly(A) tail of the transcript. Loss of a poly(A) tail of a synthetic, modified-RNA can result in increased RNA degradation. Thus, in one embodiment, a synthetic, modified-RNA as described herein does not comprise an AU-rich region. In particular, it is preferred that the 3' UTR substantially lacks AUUUA sequence elements.

In one embodiment, a ligand alters the cellular uptake, intracellular targeting or half-life of a synthetic, modified-RNA into which it is incorporated. In some embodiments a ligand provides an enhanced affinity for a selected target tissue, e.g., tissue or cell type, or intracellular compartment, e.g., mitochondria, cytoplasm, peroxisome, lysosome, as, e.g., compared to a composition absent such a ligand. Preferred ligands do not interfere with expression of a polypeptide from the synthetic, modified-RNA.

Ligands can include, for example, a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, (e.g., a lectin, glycoprotein, lipid or protein), or an antibody, that binds to a specified cell type such as a fibroblast cell. In some embodiments, where the target cell is an endothelial cell, a endothelial cell targeting agents is a vWF protein or fragment thereof. In some embodiments, other targeting group useful in the methods as disclosed herein can be, for example, a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B 12, biotin, or an RGD peptide or RGD peptide mimetic, among others.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, amino, mercapto, PEG (e.g., PEG-40K), MPEG, [MPEG]2, polyamino, alkyl, substituted alkyl, radiolabeled markers, enzymes, haptens (e.g. biotin), and transport/absorption facilitators (e.g., aspirin, vitamin E, folic acid).

Ligands can be proteins, e.g., glycoproteins, or peptides, e.g., molecules having a specific affinity for a co-ligand, or antibodies e.g., an antibody, that binds to a specified cell type such as a fibroblast cell, or other cell useful in the production of polypeptides. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose.

The ligand can be a substance, e.g., a drug, which can increase the uptake of the synthetic, modified-RNA or a composition thereof into the cell, for example, by disrupting the cell's cytoskeleton, e.g., by disrupting the cell's microtubules, microfilaments, and/or intermediate filaments. The drug can be, for example, taxol, vincristine, vinblastine, cytochalasin, nocodazole, japlakinolide, latrunculin A, phalloidin, swinholide A, indanocine, or myoservin.

One exemplary ligand is a lipid or lipid-based molecule. A lipid or lipid-based ligand can (a) increase resistance to degradation, and/or (b) increase targeting or transport into a target cell or cell membrane. A lipid based ligand can be used to modulate, e.g., binding of the modified RNA composition to a target cell.

In another aspect, the ligand is a moiety, e.g., a vitamin, which is taken up by a host cell. Exemplary vitamins include vitamin A, E, and K. Other exemplary vitamins include B vitamin, e.g., folic acid, B 12, riboflavin, biotin, pyridoxal or other vitamins or nutrients taken up, for example, by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In some embodiments the term a "cell permeation peptide" is capable of permeating a cell, e.g., a mammalian cell, such as a human cell, as well, as a peptide which permeates the blood-brain barrier. Cell permeation peptides are well known in the art, and include, but are not limited to, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin), and bipartite amphipathic peptides, such as MPG, which is derived from the fusion peptide domain of HIV-1 gp41 and the NLS of SV40 large T antigen (Simeoni et al., Nucl. Acids Res. 31:2717-2724, 2003).

Synthesis of Synthetic, Modified RNAs

The synthetic, modified-RNAs described herein can be synthesized and/or modified by methods well established in the art, such as those described in "Current Protocols in Nucleic Acid Chemistry," Beaucage, S. L. et al. (Edrs.), John Wiley & Sons, Inc., New York, N.Y., USA, which is hereby incorporated herein by reference in its entirety. Transcription methods are described further herein in the Examples.

In one embodiment of the aspects described herein, a template for a synthetic, modified-RNA is synthesized using "splint-mediated ligation," which allows for the rapid synthesis of DNA constructs by controlled concatenation of long oligos and/or dsDNA PCR products and without the need to introduce restriction sites at the joining regions. It can be used to add generic untranslated regions (UTRs) to the coding sequences of genes during T7 template generation. Splint mediated ligation can also be used to add nuclear localization sequences to an open reading frame, and to make dominant-negative constructs with point mutations starting from a wild-type open reading frame. Briefly, single-stranded and/or denatured dsDNA components are annealed to splint oligos which bring the desired ends into conjunction, the ends are ligated by a thermostable DNA ligase and the desired constructs amplified by PCR. A synthetic, modified-RNA is then synthesized from the template using an RNA polymerase in vitro. After synthesis of a synthetic, modified-RNA is complete, the DNA template is removed from the transcription reaction prior to use with the methods described herein.

In some embodiments of these aspects, the synthetic, modified RNAs are further treated with an alkaline phosphatase.

Plurality of Synthetic, Modified RNAs

In some embodiments of the aspects described herein, a plurality of different synthetic, modified-RNAs are contacted with, or introduced to, a target tissue in vivo, e.g., a muscle tissue or heart tissue and permit expression of at least two polypeptide products in the desired target tissue. In some embodiments, synthetic, modified-RNA compositions as disclosed herein can comprise two or more synthetic, modified-RNAs, e.g., 2, 3, 4, 5, 6, 7, 8, 9, 10 or more synthetic, modified-RNAs. In some embodiments, the two or more synthetic, modified-RNAs are capable of increasing expression of a desired polypeptide product (e.g., a transcription factor, a cell surface marker, a death receptor, etc.). In some embodiments, where the composition is used for the treatment of a cardiovascular disease or disorder, the composition comprises a MOD-RNA encoding VEGF and at least one other MOD-RNA encoding a different cardiac enhancing protein.

In some embodiments, when a plurality of different synthetic, modified-RNAs, synthetic, modified-RNA compositions, or media comprising a plurality of different synthetic, modified-RNAs are used to modulate expression of a desired set of polypeptides, the plurality of synthetic, modified-RNAs can be contacted with, or introduced to, a target tissue in vivo, either simultaneously or subsequently. In other embodiments, the plurality of synthetic, modified-RNAs can be contacted with, or introduced to, a target tissue in vivo separately. In addition, each synthetic, modified-RNA can be administered to the target tissue in vivo according to its own dosage regime. For example, in one embodiment, a composition can be prepared comprising a plurality of synthetic, modified-RNAs, in differing relative amounts or in equal amounts, that is contacted with a target tissue in vivo, such that the plurality of synthetic, modified-RNAs are administered simultaneously. Alternatively, one synthetic, modified-RNA at a time can be administered to a target tissue in vivo (e.g., sequentially). In this manner, the expression desired for each target polypeptide in vivo can be easily tailored by altering the frequency of administration and/or the amount of a particular synthetic, modified-RNA administered. Contacting a target tissue in vivo with each synthetic, modified-RNA separately can also prevent interactions between the synthetic, modified-RNAs that can reduce efficiency of in vivo protein expression. For ease of use and to prevent potential contamination, it is preferred to administer to or contact a target tissue in vivo with a cocktail of different synthetic, modified-RNAs, thereby reducing the number of doses required and minimizing the chance of introducing a contaminant to a target tissue in vivo.

The methods and compositions described herein permit the in vivo protein expression of one or more polypeptides to be tuned to a desired level by varying the amount of each synthetic, modified-RNA transfected. One of skill in the art can easily monitor level of in vivo protein expression encoded by a synthetic, modified-RNA using e.g., Western blotting techniques or immunocytochemistry techniques. A synthetic, modified-RNA can be administered at a frequency and dose to a target tissue in vivo that permits a desired level of in vivo protein expression. As disclosed herein in the Examples, the amount of MOD-RNA administered in vivo determines the amount of in vivo protein expression, and therefore the amount of protein expressed can be controlled based on the amount of MOD-RNA administered to the target tissue in vivo. Accordingly, each different synthetic, modified-RNA can be administered at its own dose and frequency to permit appropriate expression in the target tissue in vivo. In addition, since the synthetic, modified-RNAs administered to a target tissue in vivo is transient in nature (i.e., are degraded over time) one of skill in the art can easily remove or stop the in vivo protein expression from a synthetic, modified-RNA by halting further transfections and permitting the tissue to degrade the synthetic, modified-RNA over time. The synthetic, modified-RNAs will degrade in a manner similar to cellular mRNAs.

Introducing a Synthetic, Modified RNA into a Cell

A synthetic, modified-RNA can be introduced into a target tissue in vivo, e.g., a muscle tissue or heart tissue, e.g., for delivery to a myogenic cell, or cardiomyocyte, in any manner that achieves intracellular delivery of the synthetic, modified-RNA, such that in vivo expression of the polypeptide encoded by the synthetic, modified RNA can occur. As used herein, the term "transfecting a cell" refers to the process of introducing nucleic acids into a cell of a tissue using means for facilitating or effecting uptake or absorption into the tissue, as is understood by those skilled in the art. As the term is used herein, "transfection" does not encompass vector-mediated gene delivery, e.g., viral- or viral particle based delivery methods. Absorption or uptake of a synthetic, modified RNA into a tissue in vivo can occur through unaided diffusive or active cellular processes, or by auxiliary agents or devices. Further approaches are described herein below or known in the art.

In some embodiments, a synthetic, modified RNA can be introduced into a target tissue, e.g., muscle or heart, e.g., a myogenic cell, for example, by transfection, nucleofection, lipofection, electroporation (see, e.g., Wong and Neumann, Biochem. Biophys. Res. Commun. 107:584-87 (1982)), microinjection (e.g., by direct injection of a synthetic, modified RNA), biolistics, cell fusion, and the like.

Herein, a MOD-RNA was introduced into a tissue in vivo, e.g., heart and muscle tissue using a Mega Tran 1.0 transfection reagent (OriGene Technologies Inc.). Alternatively, herein MOD-RNA was introduced into a tissue in vivo, e.g., heart and muscle tissue using lipofectamine (RNAi MAX). While one can optimize the concentration of MOD-RNA delivered, in one embodiment, the inventors used 25 µg/µl concentration for delivery of about 100 µg MOD-RNA to a tissue in vivo.

In an alternative embodiment, a synthetic, modified RNA can be delivered using a drug delivery system such as a nanoparticle, a dendrimer, a hydrogel, a biopolymer, a polymer, a liposome, or a cationic delivery system. Positively charged cationic delivery systems facilitate binding of a synthetic, modified RNA (negatively charged polynucleotides) and also enhances interactions at the negatively charged cell membrane to permit efficient cellular uptake. Cationic lipids, dendrimers, or polymers can either be bound to modified RNAs, or induced to form a vesicle or micelle (see e.g., Kim S H., et al (2008) Journal of Controlled Release 129(2):107-116) that encases the modified RNA. Methods for making and using cationic-modified RNA complexes are well within the abilities of those skilled in the art (see e.g., Sorensen, DR., et al (2003) J. Mol. Biol. 327:761-766; Verma, UN., et al (2003) Clin. Cancer Res. 9:1291-1300; Arnold, A S et al (2007) J. Hypertens. 25:197-205, which are incorporated herein by reference in their entirety).

In some embodiments the MOD-RNA described herein can be included in biodegradable polymeric hydrogels, such as those disclosed in U.S. Pat. No. 5,410,016 to Hubbell et al. These polymeric hydrogels can be delivered to a subject and the active compounds released over time as the polymer degrades. Commercially available hydrogels can be supplied either as a dry powder or a partially hydrated paste intended for administration after dispersion in an appropriate amount of aqueous vehicle. These powders are formed by mechanical disruption of cross-linked matrices, such as absorbable gelatin sponges, U.S.P. (e.g., Gelfoam®, Pfizer, Inc. or Surgifoam™, Ethicon, Inc.), or the cakes that are formed during typical chemical or dehydrothermal cross-linking treatment (see, e.g., U.S. Pat. No. 6,063,061; U.S. Patent application pub. No. 2003/0064109). These hydrogels can be based on gelatin, collagen, dextran, chitosan. Other compositions are also used, for example, alginate (U.S. Pat. No. 5,294,446) and synthetic polymers such as polyphosphazines, polyacrylates, polyanhydrides, and polyorthoesters, as well as "block copolymers" such as mixtures of polyethylene oxide and polypropylene glycol (U.S. Pat. Nos. 5,041,138; 5,709,854; 5,736,372). In addition, U.S. Pat. Nos. 5,749,874 and 5,769,899 (both Schwartz et al, 1998) disclose two-component implants, where one component is an anchoring device, made of a relatively hard yet biodegradable material (such as polyglycolic acid, polylactic acid, or combinations thereof), which helps secure and anchor the hydrogel implants and a second component that comprises a more porous and flexible matrix.

Hydrogels can be administered dry, partially hydrated, or fully hydrated. In the fully hydrated state, the hydrogel cannot absorb further fluid, and is fully swollen in size. In contrast, a dry or partially hydrated hydrogel composition has excess adsorptive capacity. Upon administration, dry or partially hydrated hydrogel will absorb fluid leading to a swelling of the gelatin matrix in vivo. Swelling of dry or partially hydrated hydrogel should be considered in the context of administration. If desirable, the polymeric hydrogels can have microparticles or liposomes which include the active compound dispersed therein, providing another mechanism for the controlled release of MOD-RNA described herein, or a nucleic acid encoding the peptide.

In some embodiments of the aspects described herein, the composition further comprises a reagent that facilitates uptake of a synthetic, modified RNA into a cell (transfection reagent), such as an emulsion, a liposome, a cationic lipid, a non-cationic lipid, an anionic lipid, a charged lipid, a penetration enhancer or alternatively, a modification to the synthetic, modified RNA to attach e.g., a ligand, peptide, lipophilic group, or targeting moiety.

The process for delivery of a synthetic, modified RNA to a cell will necessarily depend upon the specific approach for transfection chosen. One preferred approach is to add the RNA, complexed with a cationic transfection reagent (see below) directly to the cell culture media for the cells.

It is also contemplated herein that a first and second synthetic, modified RNA are administered in a separate and temporally distinct manner. Thus, each of a plurality of synthetic, modified RNAs can be administered at a separate time or at a different frequency interval to achieve the desired expression of a polypeptide. Typically, 100 fg to 100 pg of a synthetic, modified RNA is administered per cell using cationic lipid-mediated transfection. Since cationic lipid-mediated transfection is highly inefficient at delivering synthetic, modified RNAs to the cytosol, other techniques can require less RNA. The entire transcriptome of a mammalian cell constitutes about 1 pg of mRNA, and a polypeptide (e.g., a transcription factor) can have a physiological effect at an abundance of less than 1 fg per cell.

Transfection Reagents

In certain embodiments of the aspects described herein, a synthetic, modified RNA can be introduced into a target tissue in vivo by transfection or lipofection. Suitable agents for transfection or lipofection include, for example but are not limited to, calcium phosphate, DEAE dextran, lipofectin, lipofectamine, DIMRIE C™, Superfect™, and Effectin™ (Qiagen™), Unifectin™, Maxifectin™, DOTMA, DOGS™ (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999)). In the Examples disclosed herein, the inventors introduced MOD-RNA into a tissue in vivo, e.g., heart and muscle tissue using a Mega Tran 1.0 transfection reagent (OriGene Technologies Inc.). Alternatively in some embodiments, MOD-RNA was introduced into a tissue in vivo, e.g., heart and muscle tissue, using lipofectamine (RNAi MAX). While one can optimize the concentration of MOD-RNA delivered, in one embodiment, the inventors used 25 µg/µl concentration for delivery of about 100 µg MOD-RNA to a tissue in vivo.

A synthetic, modified RNA can be transfected into a target tissue in vivo as disclosed herein as a complex with cationic lipid carriers (e.g., Oligofectamine™) or non-cationic lipid-based carriers (e.g., Transit-TKO™, Mirus Bio LLC, Madison, Wis.). Successful introduction of a modified RNA into a target tissue in vivo can be monitored using various known methods. For example, transient transfection of a target tissue in vivo herein can be signaled with a reporter, such as a fluorescent marker, such as Green Fluorescent Protein (GFP), as shown herein, or using luciferase reporter using bioluminescence detection, or using beta-gal reporter from a Cre-recombinase mouse model transfected with MOD-RNA encoding cre recombinase. Successful transfection of a target tissue in vivo with modified RNA can also be determined by measuring the protein expression level of the target polypeptide by e.g., Western Blotting or immunocytochemistry.

In some embodiments of the aspects described herein, the synthetic, modified RNA is introduced into a target tissue in vivo using a transfection reagent. Some exemplary transfection reagents include, for example, cationic lipids, such as lipofectin (Junichi et al, U.S. Pat. No. 5,705,188), cationic glycerol derivatives, and polycationic molecules, such as polylysine (Lollo et al., PCT Application WO 97/30731). Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

In other embodiments, highly branched organic compounds, termed "dendrimers," can be used to bind the exogenous nucleic acid, such as the synthetic, modified RNAs described herein, and introduce it into a target tissue in vivo.

In other embodiments of the aspects described herein, non-chemical methods of transfection are contemplated. Such methods include, but are not limited to, electroporation (methods whereby an instrument is used to create microsized holes transiently in the plasma membrane of cells under an electric discharge), sono-poration (transfection via the application of sonic forces to cells), and optical transfection (methods whereby a tiny (~1 µm diameter) hole is transiently generated in the plasma membrane of a cell using a highly focused laser). In other embodiments, particle-based methods of transfections are contemplated, such as the use of a gene gun, whereby the nucleic acid is coupled to a nanoparticle of an inert solid (commonly gold) which is then "shot" directly into the target cell's nucleus; "magnetofection," which refers to a transfection method, that uses magnetic force to deliver exogenous nucleic acids coupled to magnetic nanoparticles into target cells; "impalefection," which is carried out by impaling cells by elongated nanostructures, such as carbon nanofibers or silicon nanowires which have been coupled to exogenous nucleic acids.

Other agents may be utilized to enhance the penetration of the administered nucleic acids, including glycols, such as ethylene glycol and propylene glycol, pyrrols such as 2-pyrrol, azones, and terpenes, such as limonene and menthone.

Delivery Formulations and Pharmaceutical Compositions

In some embodiments, a synthetic, modified RNA molecule as disclosed herein for delivering to a target tissue in vivo is encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171. 1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707. 2005); and Zimmermann E et al, Electrolyte- and pH-stabilities of aqueous solid lipid nanoparticle (SLN) dispersions in artificial gastrointestinal media. Eur J Pharm Biopharm 52:203. 2001). In some embodiments, where the composition comprises more than one MOD-RNA molecule, each MOD-RNA formulated as its own nanoparticle formulation and the pharmaceutical composition comprises a plurality of MOD-RNA-nanoparticle formulations. In alternative embodiments, a nanoparticle can comprise a plurality of different synthetic modified-RNAs encoding different proteins. Each method represents a separate embodiment of the present invention.

In some embodiment, one or MOD-RNA is delivered to a target tissue in vivo in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). In some embodiments, where the composition comprises more than one MOD-RNA molecule, each MOD-RNA can be formulated as its own liposome formulation, and a pharmaceutical composition can comprise a plurality of MOD-RNA-liposome formulations. In alternative embodiments, a liposome can comprise a plurality of different synthetic modified-RNAs encoding different proteins.

In some embodiments, compositions comprising at least one MOD-RNA for delivery to a target tissue in vivo as disclosed herein can be, in another embodiment, administered to a subject by any method known to a person skilled in the art, such as parenterally, paracancerally, intramuscularly, intra-dermally, subcutaneously, intra-peritonealy, intra-ventricularly, intra-cranially, intra-vaginally or intratumorally.

In another embodiment of methods and compositions of the present invention, compositions comprising at least one MOD-RNA for delivery to a target tissue in vivo as disclosed herein are formulated in a form suitable for injection, i.e. as a liquid preparation. Suitable liquid formulations include solutions, suspensions, dispersions, emulsions, oils and the like. In another embodiment of the present invention, the active ingredient is formulated in a capsule, e.g., a slow release capsule.

In other embodiments, the pharmaceutical compositions comprising at least one MOD-RNA for delivery to a target tissue in vivo as disclosed herein can be administered by intra-arterial, or intramuscular injection of a liquid preparation. Suitable liquid formulations include solutions, suspensions, dispersions, emulsions, oils and the like. In another embodiment, the pharmaceutical compositions comprising at least one MOD-RNA as disclosed herein can be administered intra-arterially and are thus formulated in a form suitable for intra-arterial administration.

In another embodiment, the pharmaceutical compositions for delivery to a target tissue in vivo can administered intramuscularly and are thus formulated in a form suitable for intramuscular administration. Intramuscular injection can be into cardiac muscle, diagram and limb muscles, as disclosed herein.

In another embodiment, a pharmaceutical compositions comprising at least one MOD-RNA for delivery to a target tissue in vivo as disclosed herein can be administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier. In some embodiments, where protein expression in vivo in the eye is beneficial, a pharmaceutical composition comprising at least one MOD-RNA as disclosed herein is formulated in the form of an eye drop.

As used herein "pharmaceutically acceptable carriers or diluents" are well known to those skilled in the art. The carrier or diluent may be may be, in various embodiments, a solid carrier or diluent for solid formulations, a liquid carrier or diluent for liquid formulations, or mixtures thereof. In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof. In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, a compositions for delivery of a MOD-RNA to a target tissue in vivo further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, a pharmaceutical composition for delivery of a MOD-RNA to a target tissue in vivo can comprise a MOD-RNA in a controlled-release composition, i.e. a composition in which the compound is released over a period of time after administration. Controlled- or sustained-release compositions include formulation in lipophilic depots (e.g. fatty acids, waxes, oils). In another embodiment, a composition for delivery of a MOD-RNA to a target tissue in vivo is an immediate-release composition, i.e. a composition in which the entire compound is released immediately after administration.

In another embodiment, for delivery of a MOD-RNA to a target tissue in vivo, one can modify a MOD-RNA of the present invention by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In another embodiment, a composition for delivery of a MOD-RNA to a target tissue in vivo is formulated to include a neutralized pharmaceutically acceptable salt form. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Each of the above additives, excipients, formulations and methods of administration represents a separate embodiment of the present invention.

In some embodiments of the aspects described herein, involving in vivo administration of synthetic, modified-RNAs or compositions thereof to a target tissue in vivo, are formulated in conjunction with one or more penetration enhancers, surfactants and/or chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether.

A compositions comprising at least one MOD-RNA as disclosed herein can be formulated into any of many possible administration forms, including a sustained release form. The compositions can be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

A composition comprising at least one MOD-RNA as disclosed herein can be prepared and formulated as emulsions for the delivery of synthetic, modified-RNAs. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain further components in addition to the dispersed phases, and the active drug (i.e., synthetic, modified-RNA) which can be present as a solution in either the aqueous phase, oily phase or itself as a separate phase. Pharmaceutical excipients such as emulsifiers, stabilizers, dyes, and anti-oxidants can also be present in emulsions as needed. Emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

As noted above, liposomes can optionally be prepared to contain surface groups to facilitate delivery of liposomes and their contents to specific cell populations. For example, a liposome can comprise a surface groups such as antibodies or antibody fragments, small effector molecules for interacting with cell-surface receptors, antigens, and other like compounds.

Surface groups can be incorporated into the liposome by including in the liposomal lipids a lipid derivatized with the targeting molecule, or a lipid having a polar-head chemical group that can be derivatized with the targeting molecule in preformed liposomes. Alternatively, a targeting moiety can be inserted into preformed liposomes by incubating the preformed liposomes with a ligand-polymer-lipid conjugate.

A number of liposomes comprising nucleic acids are known in the art. WO 96/40062 (Thierry et al.) discloses methods for encapsulating high molecular weight nucleic acids in liposomes. U.S. Pat. No. 5,264,221 (Tagawa et al.) discloses protein-bonded liposomes and asserts that the contents of such liposomes can include an RNA molecule. U.S. Pat. No. 5,665,710 (Rahman et al.) describes certain methods of encapsulating oligodeoxynucleotides in liposomes. WO 97/04787 (Love et al.) discloses liposomes comprising RNAi molecules targeted to the raf gene. In addition, methods for preparing a liposome composition comprising a nucleic acid can be found in e.g., U.S. Pat. Nos. 6,011,020; 6,074,667; 6,110,490; 6,147,204; 6, 271, 206; 6,312,956; 6,465,188; 6,506,564; 6,750,016; and 7,112,337. Each of these approaches can provide delivery of a synthetic, modified-RNA as described herein to a cell.

In some embodiments of the aspects described herein, a composition comprising at least one MOD-RNA for in vivo protein expression in a target tissue as disclosed herein can be encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly (d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171.1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707.2005); and Zimmermann E et al, Electrolyte- and pH-stabilities of aqueous solid lipid nanoparticle (SLN) dispersions in artificial gastrointestinal media. Eur J Pharm Biopharm 52:203. 2001), the contents of which are herein incorporated in their entireties by reference.

Methods for Further Avoiding a Cell's Innate Immune or Interferon Response

In some embodiments, a composition comprising at least one MOD-RNA as disclosed herein also comprise an agent to reduce the innate immune mediated response. In one embodiment, the composition further comprises a modified RNA encoding an interferon scavenging agent (e.g., a soluble interferon receptor) to further reduce the innate immune response of tissue.

In some embodiments, small molecules that inhibit the innate immune response in cells, such as chloroquine (a TLR signaling inhibitor) and 2-aminopurine (a PKR inhibitor), can also be administered in combination with the composition comprising at least one MOD-RNA for in vivo protein expression as disclosed herein. Some non-limiting examples of commercially available TLR-signaling inhibitors include BX795, chloroquine, CLI-095, OxPAPC, polymyxin B, and rapamycin (all available for purchase from INVIVOGEN™). In addition, inhibitors of pattern recognition receptors (PRR) (which are involved in innate immunity signaling) such as 2-aminopurine, BX795, chloroquine, and H-89, can also be used in the compositions and methods comprising at least one MOD-RNA for in vivo protein expression as disclosed herein. Additionally, the compositions comprising at least one MOD-RNA for in vivo protein expression as disclosed herein can further comprise cell-penetrating peptides that inhibit proteins in the immunity pathways. Some non-limiting examples of commercially available cell-penetrating peptides include Pepin-MYD (INVIVOGEN™) or Pepinh-TRIF (INVIVOGEN™). An oligodeoxynucleotide antagonist for the Toll-like receptor signaling pathway can also be added to a comprising at least one MOD-RNA for in vivo protein expression as disclosed herein to reduce immunity signaling.

Another method for reducing the immune response of a tissue transfected with the synthetic, modified RNAs described herein is to co-transfect MOD-RNAs that encode negative regulators of innate immunity such as NLRX1. Accordingly, in some embodiments, a composition comprising at least one MOD-RNA for in vivo protein expression as disclosed herein comprises a MOD-RNA encoding one or more, or any combination of NLRX1, NS1, NS3/4A, or A46R. Additionally, in some embodiments, a composition comprising at least one MOD-RNA as disclosed herein can also comprise a synthetic, modified-RNA encoding inhibitors of the innate immune system to avoid the innate immune response generated by the tissue or the subject.

It is also contemplated herein that, in some embodiments, in a research setting one of skill in the art can avoid the innate immune response generated in the cell by using cells genetically deficient in antiviral pathways (e.g., VISA knockout cells).

In another embodiment, a composition comprising at least one MOD-RNA as disclosed herein can further comprise an immunosuppressive agent. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 20020182211. In one embodiment, a immunosuppressive agent is cyclosporine A. Other examples include myophenylate mofetil, rapamicin, and anti-thymocyte globulin. In one embodiment, the immunosuppressive drug is administered in a composition comprising at least one MOD-RNA as disclosed herein, or can be administered in a separate composition but simultaneously with, or before or after administration of a composition comprising at least one MOD-RNA to the subject. An immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the MOD-RNA as disclosed herein.

In Vivo Protein Expression Using MOD-RNAs in Assays for Identifying Therapeutic Agents In some embodiments, the methods and compositions and kits as disclosed herein for in vivo protein expression using synthetic modified RNAs provide a platform by which investigators can explore whole-organ and systemic effects of the protein expression of a single gene product or group of gene products. The ability to perform specific, directed protein expression in a facile manner (as compared with transgenic mouse technology and other genetic modification techniques in whole animals) opens new frontiers in the study of organ and system physiology. Such a powerful platform would have broad interest among biological and clinical scientists. In some embodiments, the present invention provides to methods to delivery synthetic modified RNA in vivo to an animal model to turn on and/or turn off gene expression, for example, for an inducible protein expression system. In some embodiments, the methods provide for delivering a synthetic modified RNA encoding Cre recombinase protein to an animal model to see effects of knock out of genes in particular tissues and/or cell types. In some embodiments, an animal model is a large animal model, e.g., a porcine model.

For example, one can use MOD-RNAs for the in vivo protein expression of a particular protein in a target tissue to investigate the effect of the increased protein expression on the function of the tissue, and/or animal, and/or as a potential therapeutic for a particular disease or disorder. For example, one can use a MOD-RNA encoding a protein of interest which encodes a protein with a pathological characteristic. For example, the desired pathological characteristic includes a protein expressed from a gene with a mutation and/or polymorphism which contributes to a disease pathology, e.g., a cardiovascular disease pathology as disclosed herein. In such an embodiment, the methods as disclosed herein can be in assays which investigate effect of mutations in genes on protein function in tissues in vivo, as well as to screen for MOD-RNAs expressing proteins of interest which alleviate a pathology. Therefore, the methods as disclosed herein can be used for example, to assess an effect of expression of a particular protein in vivo in a target tissue, and therefore serves as an in vivo model for drug development and disease analysis, and is useful for clinical assessment of protein therapeutics expressed from MOD-RNAs.

A plurality of assays may be run in parallel with different MOD-RNA concentrations to obtain a differential response to different levels of protein expression from the various concentrations of MOD-RNAs. As known in the art, determining the effective concentration of a MOD-RNA typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Accordingly, in some embodiments, one can use MOD-RNAs for the in vivo protein expression of a particular protein in a target tissue to investigate the effect of protein expressed from a MOD-RNA which has been manipulated, e.g., where mutations of interest have been introduced into the gene sequence etc.

In another embodiment, one can use MOD-RNAs for in vivo expression of a protein of interest in a target tissue as a model for studying differentiation pathways. In some embodiments, the MOD-RNAs of interest can be expressed in cardiac tissue, for example, to investigate the effect of specific proteins on the differentiation of cardiomyocytes along multiple cardiomyocyte lineages, for example but not limited to, cardiac muscle cells or smooth muscle cells, or to investigate the effect of different proteins to differentiate cardiac progenitors into different subpopulations, for example but not limited to atrial, ventricular, outflow tract and conduction systems.

Accordingly, a compositions as disclosed herein comprising a MOD-RNAs for protein expression of a protein of interest in a target tissue in vivo can have a variety of uses in clinical therapy, research, development, and commercial purposes. For therapeutic purposes, for example, where a MOD-RNA encodes a cardiac enhancing protein in a heart in vivo, such a composition can be administered to enhance tissue maintenance or repair of cardiac muscle for any perceived need, such as an inborn error in metabolic function, the effect of a disease condition, or the result of significant trauma. In some embodiments, administration of a MOD-RNA encoding a cardiac enhancing protein to a heart in a subject in vivo can not only help restore function to damaged or otherwise unhealthy tissues, but also facilitate remodeling of the damaged tissues.

To determine the suitability for therapeutic administration of a particular MOD-RNA encoding a cardiac enhancing protein of interest, one can first test the MOD-RNA in a suitable animal model. In embodiments, the suitability of MOD-RNA encoding a cardiac enhancing protein of interest can also be determined in an animal model by assessing the degree of cardiac recuperation that ensues from treatment with the MOD-RNA. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832). In larger animals, cryoinjury can be inflicted by placing a 30-50 mm copper disk probe cooled in liquid N2 on the anterior wall of the left ventricle for approximately 20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

In some embodiments, a MOD-RNA encoding a cardiac enhancing protein of interest may be administered in any physiologically acceptable excipients. A composition comprising a MOD-RNA encoding a protein of interest can be delivered to a target tissue, e.g., a heart by injection, catheter, or the like.

In some embodiments, a composition comprising a MOD-RNA encoding a protein of interest for in vivo protein expression in target tissue as disclosed herein can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. A composition comprising a MOD-RNA encoding a protein of interest for in vivo protein expression in target tissue as disclosed herein can also comprise or be accompanied with one or more other ingredients that facilitate the therapeutic effect, and include use of scaffolds, as well as addition of other cells. Suitable ingredients include complementary cell types, especially endothelial cells. In another embodiment, the composition may comprise resorbable or biodegradable matrix scaffolds.

Another aspect of the present invention relates to the administration of a composition comprising a MOD-RNA encoding a protein of interest for in vivo protein expression in target tissue as disclosed herein either systemically or to a target anatomical site. The composition comprising a MOD-RNA encoding a protein of interest for in vivo protein expression in target tissue as disclosed herein can be introduced into or nearby a subject's target tissue, e.g., a heart, for example, or may be administered systemically, such as, but not limited to, intra-arterial or intravenous administration. In alternative embodiments, a composition comprising a MOD-RNA encoding a protein of interest for in vivo protein expression in target tissue as disclosed herein can be administered in various ways as would be appropriate to deliver to a subject's cardiovascular system, including but not limited to parenteral, including intravenous and intraarterial administration, intrathecal administration, intraventricular administration, intraparenchymal, intracranial, intracisternal, intrastriatal, and intranigral administration. Optionally, a composition comprising a MOD-RNA encoding a protein of interest for in vivo protein expression in target tissue as disclosed herein are administered in conjunction with an immunosuppressive agent.

A composition comprising a MOD-RNA encoding a protein of interest for in vivo protein expression in target tissue as disclosed herein s disclosed herein can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is defined in the definitions sections and is determined by such considerations as are known in the art. The amount must be effective to halt the disease progression and/or to achieve improvement, including but not limited to improved survival rate or more rapid recovery, or improvement or elimination of symptoms and other indicators as are selected as appropriate measures by those skilled in the art. A composition comprising a MOD-RNA encoding a protein of interest for in vivo protein expression in target tissue as disclosed herein can be administered to a subject can take place but is not limited to the following locations: clinic, clinical office, emergency department, hospital ward, intensive care unit, operating room, catheterization suites, and radiologic suites.

Some embodiments of the present invention can be defined as any of the following numbered paragraphs.

1. A method for expressing a protein in a tissue in vivo, the method comprising contacting the tissue with a composition comprising a synthetic, modified RNA molecule encoding a polypeptide, wherein the synthetic, modified RNA molecule comprises one or more modifications, such that introducing said synthetic, modified RNA molecule to a cell in the tissue results in a reduced innate immune response relative to cell in the tissue contacted with a synthetic RNA molecule encoding the polypeptide not comprising said one or more modifications.
2. The method of paragraph 1, wherein the tissue is heart tissue or cardiac tissue.
3. The method of paragraph 1, wherein the tissue is muscle tissue.
4. The method of paragraph 3, wherein the muscle tissue is skeletal muscle.
5. The method of paragraph 3, wherein the muscle tissue is cardiac muscle.
6. The method of paragraph 3, wherein the muscle tissue is smooth muscle.
7. The method of paragraph 1, wherein the tissue is pancreatic tissue.
8. The method of paragraph 1, wherein the synthetic, modified RNA molecule is not expressed in a vector.
9. The method of paragraph 1, wherein the composition comprising the synthetic, modified RNA molecule comprises a naked synthetic, modified RNA molecule.
10. The method of paragraph 1, wherein the composition comprising the synthetic, modified RNA molecule comprises at least one synthetic, modified RNA molecule present in a lipid complex.
11. The method of paragraph 1, wherein the tissue is a mammalian tissue.
12. The method of paragraph 11, wherein the mammalian tissue is human tissue.
13. The method of paragraph 1, wherein the synthetic, modified RNA molecule comprises at least two modified nucleosides.
14. The method of paragraph 13, wherein the at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).
15. The method of paragraph 13, wherein the synthetic, modified RNA molecule, wherein the at least two modified nucleosides are 5-methylcytidine (5mC) and pseudouridine.
16. The method of paragraph 1, wherein the synthetic, modified RNA molecule further comprises a 5' cap.
17. The method of paragraph 16, wherein the synthetic, modified RNA molecule, wherein the 5' cap is a 5' cap analog.
18. The method of paragraph 17, wherein the 5' cap analog is a 5' diguanosine cap.
19. The method of paragraph 1, wherein the synthetic, modified RNA molecule does not comprise a 5' triphosphate.
20. The method of paragraph 1, wherein the synthetic, modified RNA molecule further comprises a poly(A) tail, a Kozak sequence, a 3' untranslated region, a 5' untranslated region, or any combination thereof.
21. The method of paragraph 20, wherein the poly(A) tail, the Kozak sequence, the 3' untranslated region, the 5' untranslated region, or the any combination thereof comprises one or more modified nucleosides.
22. The method of paragraph 21, wherein the one or more modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).
23. The method of paragraph 1, wherein the synthetic, modified RNA molecule is treated with an alkaline phosphatase.
24. The method of paragraph 1, wherein the synthetic, modified RNA molecule encodes a VEGF polypeptide.
25. The method of paragraph 23, wherein the VEGF polypeptide is human VEGF (hVEGF).
26. The method of paragraph 1, wherein the synthetic, modified RNA molecule encodes a dystrophin polypeptide.
27. The method of paragraph 1, wherein the synthetic, modified RNA molecule encodes an alpha 1 anti-trypsin polypeptide.
28. The method of paragraph 1, wherein the synthetic, modified RNA molecule encodes a polypeptide for a loss of function disease.
29. The method of paragraph 27, wherein the loss of function disease is cystic fibrosis.
30. The method of paragraph 29, wherein the synthetic, modified RNA molecule encodes a cystic fibrosis transmembrane conductance regulator (CFTR) polypeptide.
31. The method of paragraph 1, wherein the synthetic, modified RNA molecule encodes a polypeptide disclosed in any of Tables 1, 2, 3, 4, 5, 6, or 7.
32. The method of paragraph 1, wherein contacting the tissue with the synthetic, modified RNA molecule comprises direct injection into the muscle.
33. The method of paragraph 1, wherein contacting the tissue with the synthetic, modified RNA molecule comprises contacting the tissue with an implantable device comprising, or coated with the synthetic, modified RNA molecule.
34. The method of paragraph 33, wherein the implantable device is a stent.
35. The method of paragraph 33, wherein the implantable device is an implantable delivery pump.
36. The method of paragraph 1, wherein contacting the tissue with the synthetic, modified RNA molecule comprises delivering the synthetic, modified RNA molecule via a catheter.
37. The method of paragraph 1, wherein contacting the tissue with the synthetic, modified RNA molecule comprises delivering the synthetic, modified RNA molecule via an endoscope.

38. The method of paragraph 1, wherein the composition comprises a concentration of synthetic, modified RNA molecule of greater than 100 ng/µl.

39. The method of paragraph 1, wherein the composition comprises a concentration of synthetic, modified RNA molecule of between 1-25 µg/µl.

40. The method of paragraph 1, wherein the composition comprises a concentration of synthetic, modified RNA molecule of between 25 µg/µl and 50 µg/µl.

41. A method for enhancing cardiac function in a subject, the method comprising administering to the subject a composition comprising a synthetic, modified RNA molecule encoding a polypeptide which enhances the cardiac function in the subject, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein expression of the polypeptide from the synthetic, modified RNA molecule enhances cardiac function in the subject.

42. The method of paragraph 41, wherein the synthetic, modified RNA molecule is as according to paragraphs 8-22.

43. The method of paragraph 41, wherein the subject suffers from a disease or disorder characterized by insufficient cardiac function.

44. The method of paragraph 41, wherein the subject suffers from a structural heart disease.

45. The method of paragraph 41, wherein the disease or disorder is congestive heart failure, cardiomyopathy, myocardial infarction, tissue ischemia, cardiac ischemia, vascular disease, acquired heart disease, congenital heart disease, atherosclerosis, cardiomyopathy, dysfunctional conduction systems, dysfunctional coronary arteries, pulmonary heard hypertension.

46. The method of paragraph 41, wherein the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis and congenital heart disease.

47. The method of paragraph 41, wherein the synthetic, modified RNA molecule encodes a VEGF polypeptide.

48. The method of paragraph 41, wherein the VEGF polypeptide is human VEGF (hVEGF).

49. The method of paragraph 41, wherein the synthetic, modified RNA molecule encodes a dystrophin polypeptide.

50. The method of paragraph 41, wherein the synthetic, modified RNA molecule encodes an alpha 1 anti-trypsin polypeptide.

51. The method of paragraph 41, wherein the synthetic, modified RNA molecule encodes a polypeptide for a loss of function disease.

52. The method of paragraph 41, wherein the synthetic modified RNA molecule expresses a polypeptide which is not expressed in the heart, or is expressed at low levels as compared to normal expression in the heart, or is expressed as a gain of function or mutant protein as compared to the native wild-type form of the polypeptide in the subject.

53. The method of paragraph 41, wherein the synthetic, modified RNA molecule encodes a polypeptide disclosed in any of Tables 1, 2, 3, 4, 5, 6, or 7.

54. The method of paragraph 41, wherein the subject is a mammal.

55. The method of paragraph 54, wherein the mammal is a human.

56. The method of paragraph 41, wherein the subject has suffered myocardial infarction.

57. The method of paragraph 41, wherein the subject has or is at risk of heart failure.

58. The method of paragraph 57, wherein the heart failure is acquired heart failure.

59. The method of paragraph 57, wherein the heart failure is associated with atherosclerosis, cardiomyopathy, congestive heart failure, myocardial infarction, ischemic diseases of the heart, atrial and ventricular arrhythmias, hypertensive vascular diseases, peripheral vascular diseases.

60. The method of paragraph 41, wherein the subject has a congenital heart disease.

61. The method of paragraph 41, wherein the subject has a condition selected from a group consisting of: hypertension; blood flow disorders; symptomatic arrhythmia; pulmonary hypertension; arthrosclerosis; dysfunction in conduction system; dysfunction in coronary arteries; dysfunction in coronary arterial tree and coronary artery colaterization.

62. The method of paragraph 41, wherein enhancing cardiac function is a method to treat or prevent heart failure.

63. The method of paragraph 41, wherein the composition is administered via endomyocardial, epimyocardial, intraventricular, intracoronary, retrosinus, intra-arterial, intrapericardial, or intravenous administration route.

64. The method of paragraph 41, wherein the composition is administered to the subject's vasculature.

65. The method of paragraph 41, wherein the composition is administered to the subject by direct injection into the heart.

66. The method of paragraph 41, wherein the composition is administered to the subject using an implantable device, wherein the implantable device comprises or is coated with the synthetic, modified RNA molecule.

67. The method of paragraph 66, wherein the implantable device is a stent.

68. The method of paragraph 66, wherein the implantable device is an implantable delivery pump.

69. The method of paragraph 41, wherein the composition is administered to the subject by a catheter.

70. The method of paragraph 41, wherein the composition is administered to the subject via an endoscope.

71. The method of paragraph 41, wherein the composition comprises a concentration of synthetic, modified RNA molecule of greater than 100 ng/µl.

72. The method of paragraph 41, wherein the composition comprises a concentration of synthetic, modified RNA molecule of between 1-25 µg/µl.

73. The method of paragraph 41, wherein the composition comprises a concentration of synthetic, modified RNA molecule of between 25 µg/µl and 50 µg/µl.

74. The method of paragraph 41, wherein the synthetic modified RNA molecule expresses a polypeptide which is not expressed in the heart, or is expressed at low levels as compared to normal expression in the heart, or is expressed as a gain of function or mutant protein as compared to the native wild-type form of the polypeptide in the subject.

75. Use of a synthetic, modified RNA molecule encoding a Cre recombinase polypeptide to knock out a gene in an in vivo Cre animal model.

76. A method for increasing mobilization, expansion and/or differentiation of heart progenitor cells, the method comprising: administering to the subject a composition comprising a synthetic, modified RNA molecule encoding a polypeptide which increases mobilization, expansion and/or differentiation of heart progenitor cells in the subject, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein expression of the polypeptide from the synthetic, modified RNA molecule increases mobilization, expansion and/or differentiation of heart progenitor cells in the subject.

77. The method of paragraph 76, wherein the polypeptide which increases mobilization, expansion and/or differentiation of heart progenitor cells in the subject comprises a VEGF polypeptide.

78. The method of paragraph 77, wherein the VEGF polypeptide comprises VEGF-A.

79. The method of paragraph 76, wherein the subject has a condition selected from a group consisting of: hypertension; blood flow disorders; symptomatic arrhythmia; pulmonary hypertension; arthrosclerosis; dysfunction in conduction system; dysfunction in coronary arteries; dysfunction in coronary arterial tree and coronary artery colaterization.

80. The method of paragraph 76, wherein the subject is a human.

81. The method of paragraph 79, wherein the subject has suffered myocardial infarction.

82. The method of paragraph 76, wherein the heart progenitors comprise WT-1 progenitors.

83. A method for treating a tumor in a subject, the method comprising;
administering a compositions comprising a synthetic, modified RNA molecule encoding a polypeptide which enhances neovascularization in the subject, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein expression of the polypeptide from the synthetic, modified RNA molecule enhances neovascularization in the tumor;
and administering a chemotherapeutic agent to the subject; wherein the neovascularization increases the effectiveness of a chemotherapeutic agent administered to the subject; whereby the tumor is treated.

84. The method of paragraph 83, wherein the synthetic, modified RNA molecule is not expressed in a vector.

85. The method of paragraph 83, wherein the composition comprising the synthetic, modified RNA molecule comprises a naked synthetic, modified RNA molecule.

86. The method of paragraph 83, wherein the composition comprising the synthetic, modified RNA molecule comprises at least one synthetic, modified RNA molecule present in a lipid complex.

87. The method of paragraph 83, wherein the synthetic, modified RNA molecule comprises at least two modified nucleosides.

88. The method of paragraph 87, wherein the at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

89. The method of paragraph 87, wherein the synthetic, modified RNA molecule, wherein the at least two modified nucleosides are 5-methylcytidine (5mC) and pseudouridine.

90. The method of paragraph 83, wherein the synthetic, modified RNA molecule further comprises a 5' cap.

91. The method of paragraph 90, wherein the synthetic, modified RNA molecule, wherein the 5' cap is a 5' cap analog.

92. The method of paragraph 91, wherein the 5' cap analog is a 5' diguanosine cap.

93. The method of paragraph 83, wherein the synthetic, modified RNA molecule does not comprise a 5' triphosphate.

94. The method of paragraph 83, wherein the synthetic, modified RNA molecule further comprises a poly(A) tail, a Kozak sequence, a 3' untranslated region, a 5' untranslated region, or any combination thereof.

95. The method of paragraph 94, wherein the poly(A) tail, the Kozak sequence, the 3' untranslated region, the 5' untranslated region, or the any combination thereof comprises one or more modified nucleosides.

96. The method of paragraph 95, wherein the one or more modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

97. The method of paragraph 83, wherein the synthetic, modified RNA molecule is treated with an alkaline phosphatase.

98. The method of paragraph 83, wherein the subject suffers from an adenocarcinoma.

99. The method of paragraph 83, wherein the subject suffers from a cancer comprising a tumor having a layer of desmoplastic tissue.

100. The method of paragraph 98, wherein the cancer is pancreatic ductal adenocarcinoma (PDAC).

101. The method of paragraph 83, wherein the synthetic, modified RNA molecule encodes a VEGF polypeptide.

102. The method of paragraph 83, wherein the VEGF polypeptide is human VEGF (hVEGF).

103. The method of paragraph 83, wherein the synthetic, modified RNA molecule encodes a polypeptide disclosed in Table 3.

104. The method of paragraph 83, wherein the subject is a mammal.

105. The method of paragraph 104, wherein the mammal is a human.

106. The method of paragraph 83, wherein the composition is administered via intravenous or trans-tumoral administration route.

107. The method of paragraph 83, wherein the composition is administered to the subject's vasculature.

108. The method of paragraph 83, wherein the composition is administered to the subject by direct injection into the tumor.

109. The method of paragraph 83, wherein the composition is administered to the subject using an implantable device, wherein the implantable device comprises or is coated with the synthetic, modified RNA molecule.

110. The method of paragraph 83, wherein the composition is administered to the subject by a catheter.

111. The method of paragraph 83, wherein the composition is administered to the subject via an endoscope.

112. The method of paragraph 83, wherein the composition comprises a concentration of synthetic, modified RNA molecule of greater than 100 ng/µl.

113. The method of paragraph 83, wherein the composition comprises a concentration of synthetic, modified RNA molecule of between 1-25 µg/µl.

114. The method of paragraph 83, wherein the composition comprises a concentration of synthetic, modified RNA molecule of between 25 µg/µl and 50 µg/µl.

115. The method of paragraph 83, wherein the chemotherapeutic agent is selected from the group consisting of: gemcitabine; fluorouracil, capecitabine; ciplastin; irinotecan; oxaliplatin; 5-fluorouracil; folinic acid; and erlotinib.

116. A method for treating a tumor in a subject, the method comprising;
administering a compositions comprising a synthetic, modified RNA molecule which inhibits the expression of a polypeptide which enhances Hedgehog signaling in the tumor, wherein the synthetic, modified RNA molecule comprises one or more modifications, such that administration of said synthetic, modified RNA molecule to the subject results in a reduced innate immune response relative to administration of a synthetic RNA molecule encoding the polypeptide not comprising said one or more modifications, and wherein inhibition of the polypeptide which enhances Hedgehog signaling by the synthetic, modified RNA molecule reduces the amount or proliferation of desmoplastic tissue associated with the tumor; and administering a chemotherapeutic agent to the subject; wherein the reduced amount or proliferation of the desmoplastic tissue increases the effectiveness of a chemotherapeutic agent administered to the subject; whereby the tumor is treated.

117. The method of paragraph 116, wherein the synthetic, modified RNA molecule is not expressed in a vector.

118. The method of paragraph 116, wherein the composition comprising the synthetic, modified RNA molecule comprises a naked synthetic, modified RNA molecule.

119. The method of paragraph 116, wherein the composition comprising the synthetic, modified RNA molecule comprises at least one synthetic, modified RNA molecule present in a lipid complex.

120. The method of paragraph 116, wherein the synthetic, modified RNA molecule comprises at least two modified nucleosides.

121. The method of paragraph 120, wherein the at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

122. The method of paragraph 120, wherein the synthetic, modified RNA molecule, wherein the at least two modified nucleosides are 5-methylcytidine (5mC) and pseudouridine.

123. The method of paragraph 116, wherein the synthetic, modified RNA molecule further comprises a 5' cap.

124. The method of paragraph 123, wherein the synthetic, modified RNA molecule, wherein the 5' cap is a 5' cap analog.

125. The method of paragraph 123, wherein the 5' cap analog is a 5' diguanosine cap.

126. The method of paragraph 116, wherein the synthetic, modified RNA molecule does not comprise a 5' triphosphate.

127. The method of paragraph 116, wherein the synthetic, modified RNA molecule further comprises a poly(A) tail, a Kozak sequence, a 3' untranslated region, a 5' untranslated region, or any combination thereof.

128. The method of paragraph 127, wherein the poly(A) tail, the Kozak sequence, the 3' untranslated region, the 5' untranslated region, or the any combination thereof comprises one or more modified nucleosides.

129. The method of paragraph 128, wherein the one or more modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

130. The method of paragraph 116, wherein the synthetic, modified RNA molecule is treated with an alkaline phosphatase.

131. The method of paragraph 116, wherein the subject suffers from an adenocarcinoma.

132. The method of paragraph 116, wherein the subject suffers from a cancer comprising a tumor having a layer of desmoplastic tissue.

133. The method of paragraph 131, wherein the cancer is pancreatic ductal adenocarcinoma (PDAC).

134. The method of paragraph 116, wherein the synthetic, modified RNA molecule is an antisense inhibitor of a mRNA encoding a protein selected from the group consisting of:
Hedehog (Hh); Smoothened (Smo); Patched 1 (Ptc1); and Gli.

135. The method of paragraph 116, wherein the polypeptide which enhances Hedgehog signaling is a human polypeptide.

136. The method of paragraph 116, wherein the subject is a mammal.

137. The method of paragraph 136, wherein the mammal is a human.
138. The method of paragraph 116, wherein the composition is administered via intravenous or trans-tumoral administration route.
139. The method of paragraph 116, wherein the composition is administered to the subject's vasculature.
140. The method of paragraph 116, wherein the composition is administered to the subject by direct injection into the tumor.
141. The method of paragraph 116, wherein the composition is administered to the subject using an implantable device, wherein the implantable device comprises or is coated with the synthetic, modified RNA molecule.
142. The method of paragraph 116, wherein the composition is administered to the subject by a catheter.
143. The method of paragraph 116, wherein the composition is administered to the subject via an endoscope.
144. The method of paragraph 116, wherein the composition comprises a concentration of synthetic, modified RNA molecule of greater than 100 ng/µl.
145. The method of paragraph 116, wherein the composition comprises a concentration of synthetic, modified RNA molecule of between 1-25 µg/µl.
146. The method of paragraph 116, wherein the composition comprises a concentration of synthetic, modified RNA molecule of between 25 µg/µl and 50 µg/µl.
147. The method of paragraph 116, wherein the chemotherapeutic agent is selected from the group consisting of: gemcitabine; fluorouracil, capecitabine; ciplastin; irinotecan; oxaliplatin; 5-fluorouracil; folinic acid; and erlotinib.

The present invention is further illustrated by the following examples which in no way should be construed as being further limiting, The contents of all cited references, including literature references, issued patents, published patent applications, and co-pending patent applications, cited throughout this application are hereby expressly incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

The examples presented herein relate to the methods and compositions for efficient protein expression in a tissue in vivo, comprising contacting a tissue with a composition comprising a synthetic modified RNA (MOD-RNA) expressing a protein of interest. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Isolation of Human Fetal Cardiomyocytes

The hearts were digested with 300 U/ml of collagenase type II and 0.65 mg/ml proteinase, bacterial type XXIV at 37 C (with shaking at 150 rpm) for only 5-10 min. After that, the hearts were further digested with 300 U/ml of collagenase type II at 37° C. (with shaking at 150 rpm) for 90 min: after each 15 min digestion, the supernatant was collected and mixed with neonatal calf serum which was then centrifuged at 30×g for 2 minutes at 4 C. After centrifugation, the supernatant was collected—this was the "cardiac fibroblast (Fb)" fraction and the pellet was the "cardiomyocyte (CM)" fraction.

Both fractions can be further cultured for a differential plating step. From the pellet of CM and Fb, CMs were resuspend in dark media and the Fb in fibroblast media. Plate the CM in a gelatin-coated well and incubate O/N. Plate the Fb in a non-gelatinized tissue culture plate and incubate O/N at 37. Next morning, we can be able to see attached mesenchymal cells in the plate. The floating cells should contain slow mesenchymal cells and CM. Next, one can perform another differential plating step by collecting the supernatant and placing it in a new plate for another 3 hours. After this time, the supernatant should mostly contain only CM that we can still recover by plating them on a gelatin-coated plate overnight. There should be mesenchymal cells on the second plate as well. After each incubation time make sure to wash the plates with PBS with Ca2+ at least 5 times to detach loosen cells. Then, replace with the adequate media.

Concentration of Modified, Synthetic RNA (RNA-MOD) for Use In Vivo

For in vivo protein expression in a target tissue using a MOD-RNA, the inventors concentrated the MOD-RNA to at least 25 µg/µl. To concentrate the MOD-RNA, the MOD-RNA is precipitated as follows:

1:10 volume of 5M Ammonium Acetate (NH4Ac) was added to the purified MOD-RNA, the 2.75 volumes of 100% ethanol is added and mixed well, and incubated at −20° C. for 30 minutes. Next, the liquid was aliquoted into 1.7 ml RNAase-Free tubes and microcentrifuged at 13000 for 15 min at 4° C. After removal and discarding of the supernatant, the pellet was washed with 500 µL 70% cold ethanol, followed by a second centrifugation at 13000 for 15 min at 4° C. After centrifugation, the 70% ethanol supernatant is removed, and the pellet undergoes a second wash in 500 µl of 70% cold ethanol and repeat of a third centrifugation at 13000 for 15 min at 4° C. After centrifugation, the second wash of 70% ethanol supernatant is removed, and the pellet is air-dried for 2 hours. The pellet is resuspend using TE buffer to concentration of 25 µg/µl.

In Vivo Injection of Modified RNA

Open heart surgery was performed for injection into the heart, for both muscle and heart injection, about 100 µl of MOD-RNA was injected into the skeletal muscle and/or heart of each mouse. MOD-RNA was used with Lipofectamine™ as the delivery vehicle, and was directly injected into the heart and skeletal muscle.

Example 1

MOD-RNA Encoding Proteins Expressed in Muscle Cells

As shown in FIGS. 1A-3B, the inventors demonstrate efficient protein expression of eGFP from synthetic modified RNA (MOD-RNA) in mouse embryonic cardiomyocytes and human fetal cardiomyocytes in vitro. The inventors demonstrate that cardiomyocytes can express two or more proteins from transfected MOD-RNAs in the same transfected cell (data not shown).

Example 2

Protein Expression from MOD-RNA in Heart and Muscle Tissue In Vivo

Figure 5A:
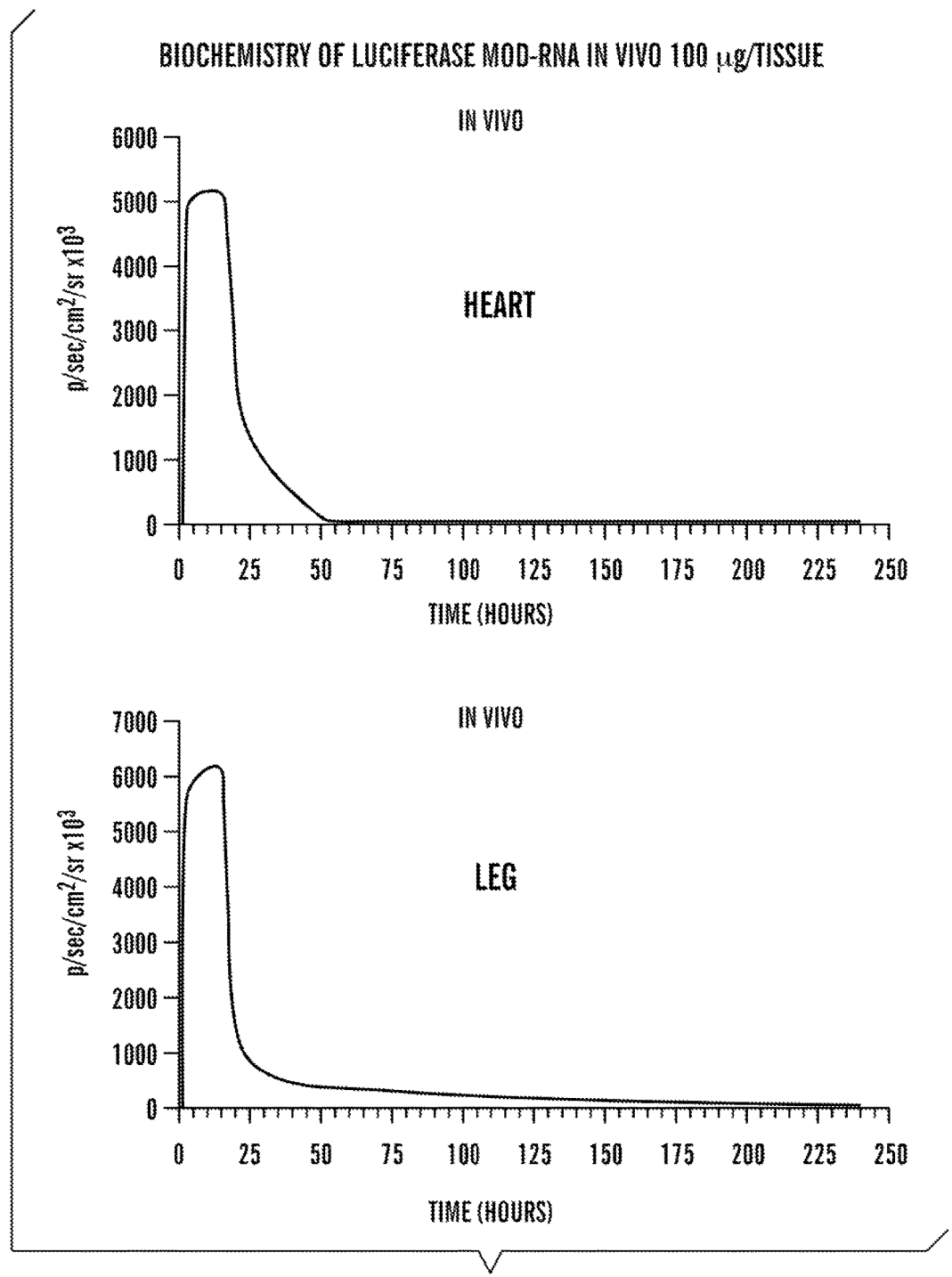
FIGS. 5A-5B shows in vivo transfection of mouse heart cells and mouse quadriceps femoris with luciferase MOD-RNA. Balb/c skeletal (leg) and heart muscles were injected in vivo with different doses of Luc MOD RNA.

High levels of in vivo protein expression was detected in mouse muscle and hearts at least 3 hours after direct injection of MOD-RNA expressing luciferase protein into the leg muscle or heart, as detected by bioluminescent imaging (data not shown). Protein expression in vivo lasted for about 4-5 days (FIG. 5A).

Figure 6:
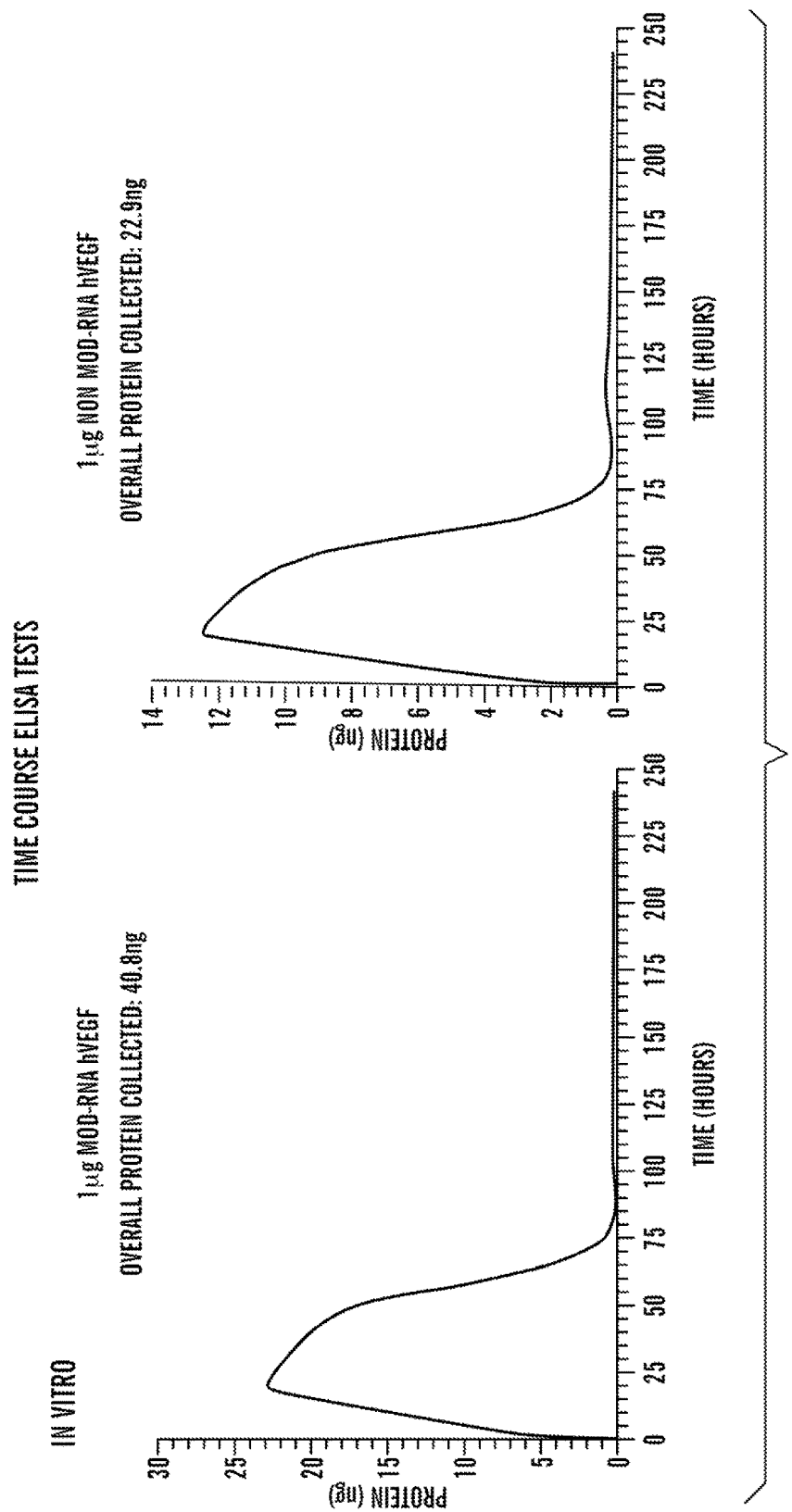
FIG. 6 shows the translation and functionality of hVEGF MOD-RNA in vitro. Human cardiac fibroblasts were transfected with hVEGF MOD-RNA and non-MOD RNA and hVEGF measured using ELISA. Shown is an in vitro comparison of cardiac fibroblasts (CF) transfection with 1 μg per well (100,000/well) of hVEGF MOD-RNA or Non-MOD-RNA, showing 2-fold higher expression of hVEGF protein from MOD-RNA as compared to from NonMOD-RNA indicates reduce translation in the latter. High VEGF protein expression was secreted from cardiomyocytes transfected with 1 μg hVEGF MOD-RNA (left panel, 40.8 ng total hVEGF). Lower hVEGF was expressed and secreted from cardiomyocytes transfected with 1 μg non-MOD RNA hVEGF (22.9 ng, right panel).
Figure 7:
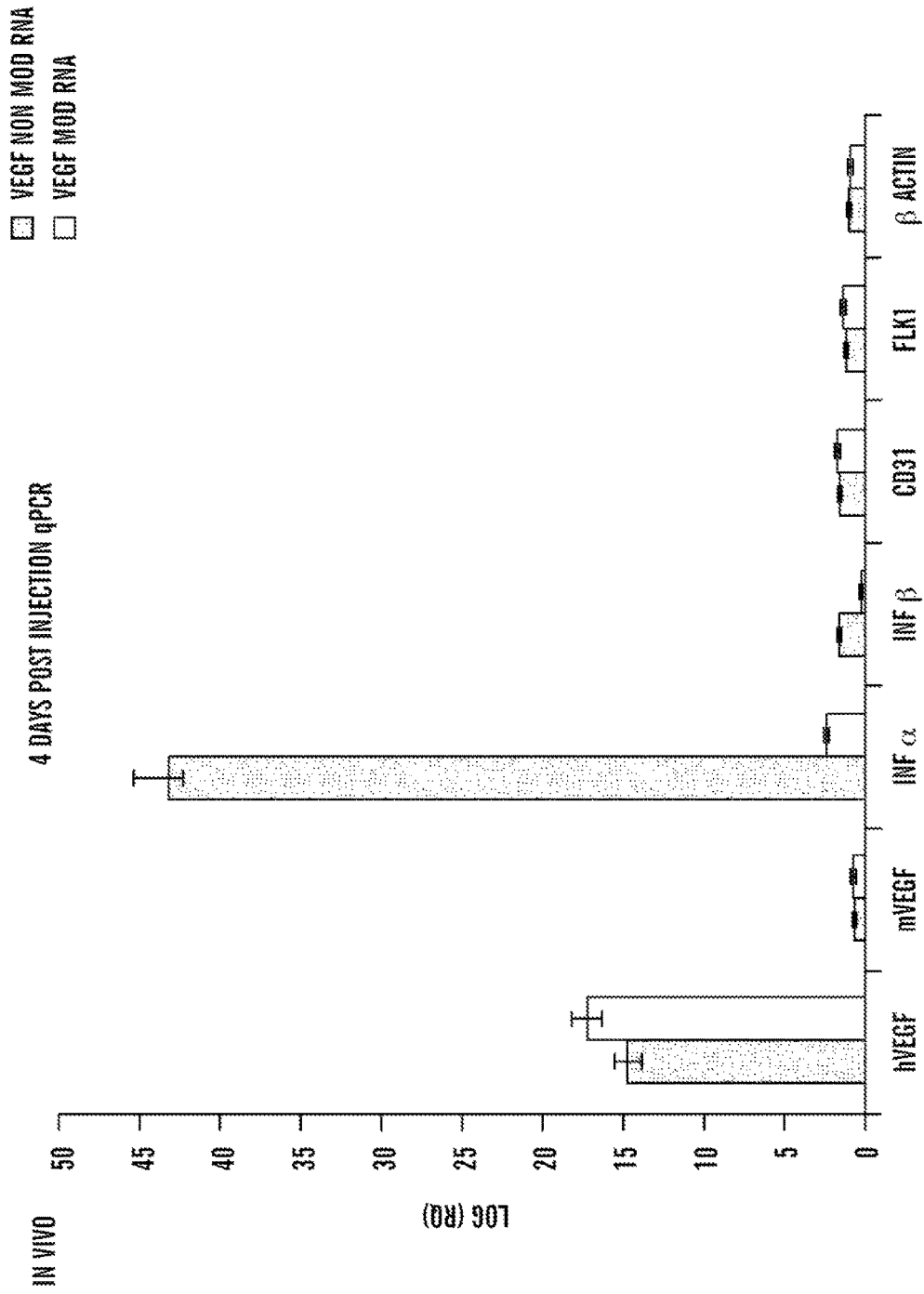
FIG. 7 shows MOD-RNA does not elicit an innate immune response in vivo. Shown is a histogram of results of levels of gene expression after mouse heart was transfected with hVEGF MOD-RNA and non-MOD RNA in vivo. Higher levels of hVEGF gene expression is detected after transfection of hVEGF MOD-RNA as compared with non-MOD RNA. Additionally, high levels of INFα gene expression, an signal that the innate immune response has been elicited, was detected in hVEGF Non-Mod RNA, but was absent after transfection with hVEGF RNA-MOD in vivo.

In vivo protein expression of cre-recombinase from MOD-RNA expressing cre could be used to induce beta-galactosidase expression in the heart and leg muscles in vivo (data not shown) and demonstrates that all different cell types on the surface of the heart take up the MOD-RNA and express the encoded protein (data not shown). Levels of in vivo protein expression from MOD-RNA was at least 2-fold higher than levels of protein from non-modified RNA (FIG. 6), and also did not elicit an innate immune response (FIG. 7).

Figure 8:
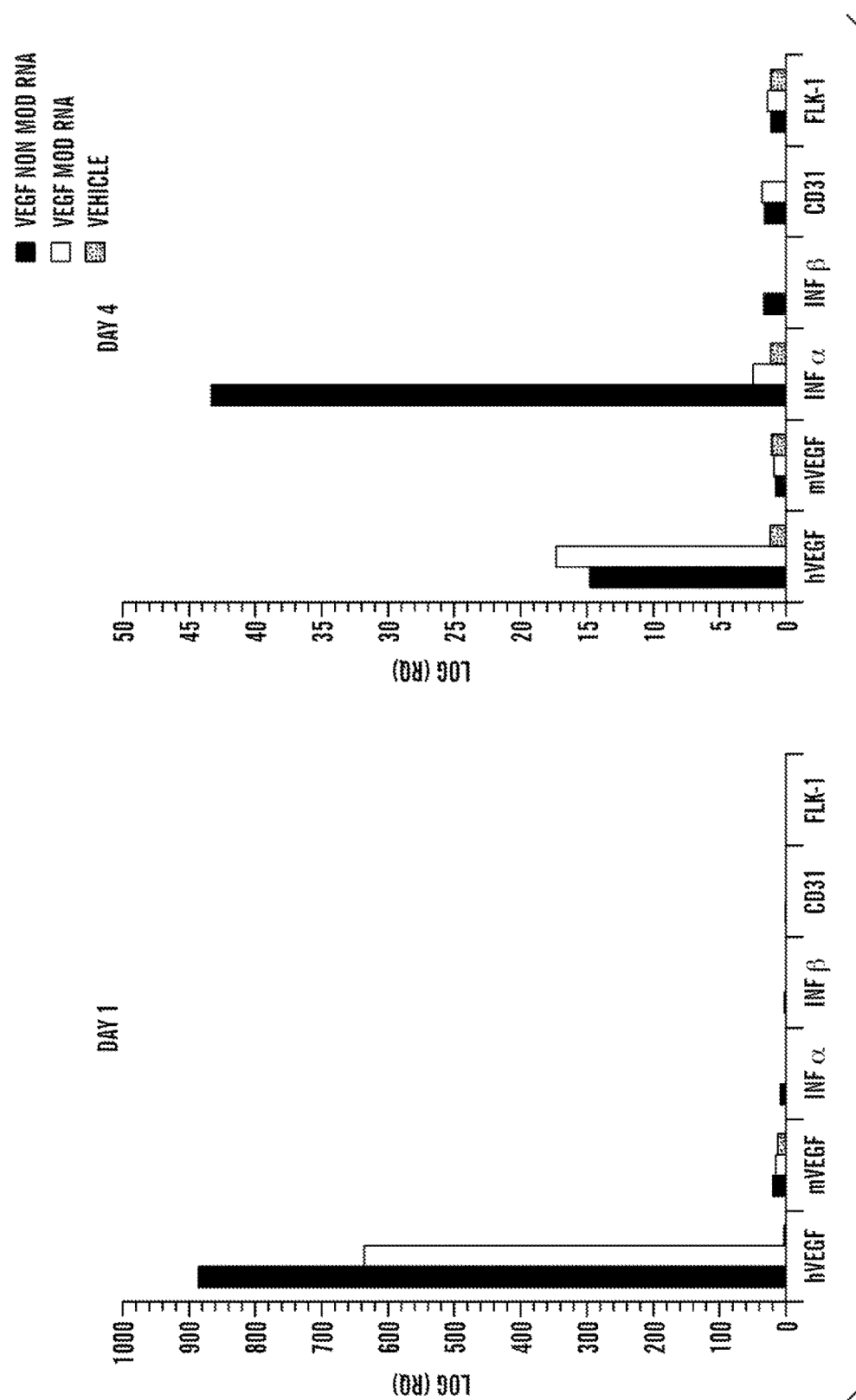
FIG. 8 shows the immunogenic and functionality of hVEGF MOD-RNA in vivo. Balb/c skeletal (leg) muscles were injected in vivo with 100 μg of hVEGF MOD-RNA or NonMOD-RNA. 1 or 4 days post delivery, muscles were removed and RNA was extracted and qPCR was preformed for hVEGF, mVEGF, INFα, INFβ, CD31 and Flk-1.

When MOD-RNA encoding hVEGF was injected into mouse muscles for 10 days (daily injections of 1 µg/day), in vivo protein expression of VEGF was functional and induced morphological changes in the muscle tissue (data not shown). Additionally, MOD-RNA encoding hVEGF was capable of repairing and preventing damage to the heart in a mouse model of myocardial infarction (FIG. 8). In particular, the inventors have demonstrated herein that the in vivo delivery a synthetic modified RNA encoding a hVEGF polypeptide to the heart of a mouse model of myocardial infarction prevents a myocardial infarct from occurring and significantly prevents damage to the heart after ischemic insult. In some embodiments, in vivo delivery a synthetic modified RNA encoding a hVEGF polypeptide also promoted recovery of the heart from ischemia. In some embodiments, the synthetic modified RNA encoding VEGF can be delivered to the myocardium via direct intramyocardial injection.

Example 3

Driving Heart Progenitor Cell Fate and Regeneration In Vivo Via Chemically Modified mRNA Background A family of multipotent heart progenitors is responsible for the diversification and expansion of distinct cardiac muscle, vascular smooth muscle, and endothelial cell lineages during cardiogenesis. Unlocking the potential of these progenitors for cell-based regenerative therapeutics has been hampered by difficulties with scalability, grafting, survival, rejection, and electrical coupling. Recent studies have identified a rare number of post-natal heart progenitors, along with developmental cues that control their renewal, fate, and function during in vitro cardiogenesis in pluripotent stem cells and clonal assays. If the authentic in vivo paracrine factors could be identified and delivered in an efficient, localized, and transient manner in the injured adult heart, the in vivo cardiac delivery of paracrine factors might represent a viable alternative therapeutic strategy, akin to the known clinical utility of erythropoietin and GM-CSF to selectively augment specific blood cell lineages.

In support of this concept, recent studies have suggested the presence of endogenous paracrine signals that can expand these progenitors following cardiac injury in vivo, although the precise subset of progenitors and the exact paracrine signals are largely unclear. Herein, the inventors have identified VEGF-A as a key fate-switch protein factor in the human fetal heart that expands the vascular progenitor pool in the family of multipotent human heart progenitors during ES cell cardiogenesis, and have utilized chemically modified mRNA to transiently and efficiently express the corresponding protein at high levels in human and murine cardiomyocytes in vitro, as well as in the adult murine heart following injury. A combination of lineage tracing and FACS analyses in three independent genetically engineered mouse model systems document that VEGF-A is expanding and driving rare pre-existing WT-1 epicardial progenitors away from a previously described interstitial fibroblast like state and towards a cardiac and vascular fate following myocardial infarction. The therapeutic effect includes a marked increase in WT1+ epicardial progenitors and their vascular cell lineages, an increase in capillary density, a marked reduction in cardiac fibrosis, an improvement in global cardiac function, and generation of islands of de novo cardiomyocytes. In summary, modRNA allows the rapid in vivo assay of known or novel paracrine protein factors that can drive the expansion and fate of endogenous heart progenitors following heart injury. In addition, VEGF-A modRNA represents a novel heart progenitor cell fate switch following injury, and indicates a new cell-free therapeutic paradigm to achieve the in vivo recruitment and subsequent differentiation of endogenous heart progenitors for cardiovascular regeneration.

Results

Figure 9A:
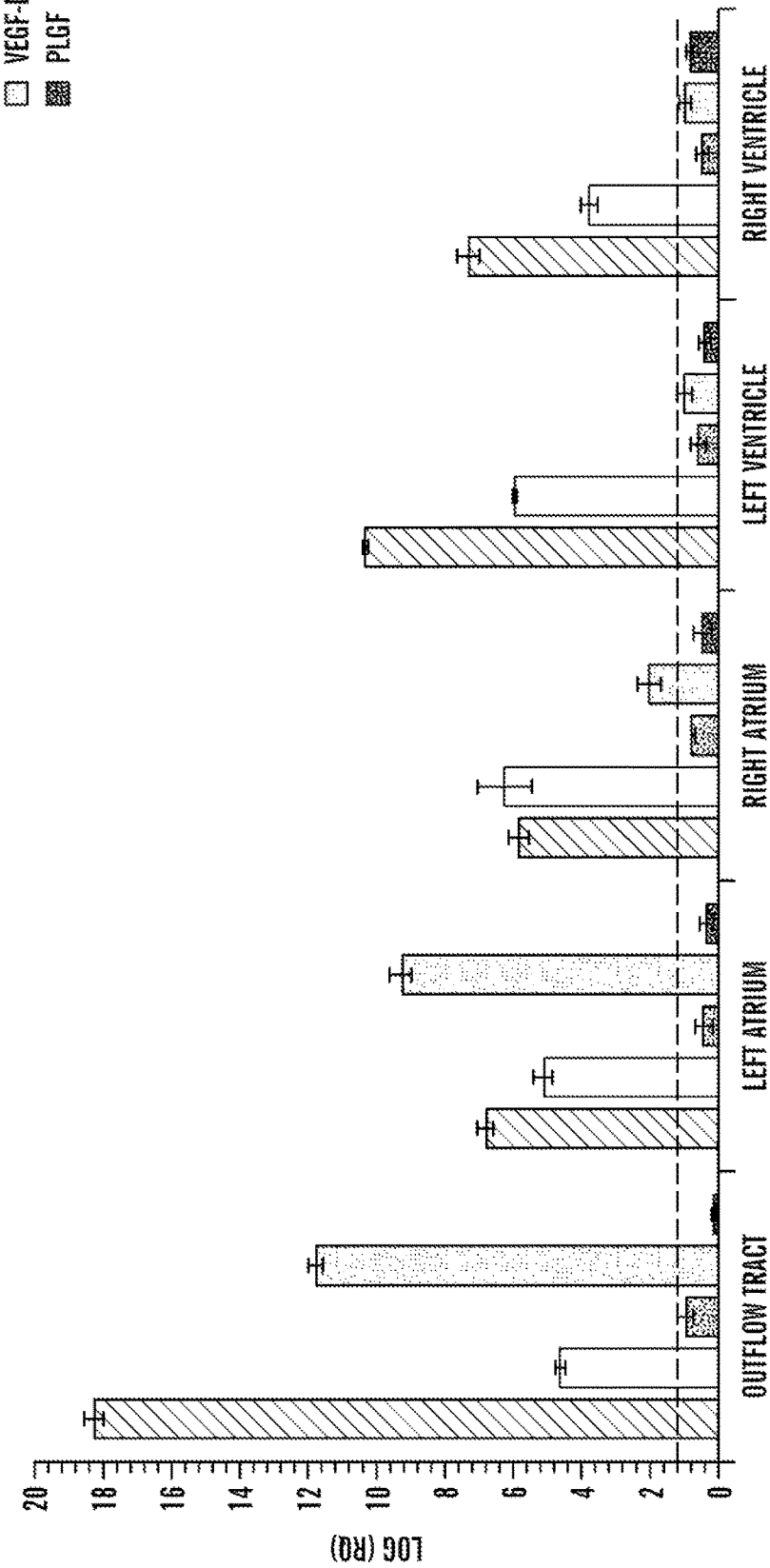
FIGS. 9A-9E show highly efficient transfection of cardiomyocytes with MOD RNA and hVEGF-A MOD RNA in vitro.

To identify candidate paracrine signals that might serve as cell-fate switches for multipotent heart progenitors, the inventors identified a panel of paracrine factors in the human fetal heart and then tested them in a genetically engineered human ES cell based assay system that allows the tracking of primordial ISL1+ progenitors towards vascular lineages, including the WT-1+ progenitor pool. VEGF-A was the most abundant angicrine factors in the human fetal heart (FIG. 9A), and independent studies documented its ability to markedly augment the number of WT-1 progenitors and their subsequent conversion to vascular endothelial lineages. While in vivo delivery of VEGF-A$^{165}$ to the heart to induce cardiac vascularization is known in the art, many studies using different delivery systems such as naked DNA plasmids, recombinant proteins or viruses, were hampered by constant protein expression and low efficiency of transfecting cardiomyocytes, short half-life of the protein, generation of neutralizing antibodies against the protein or anti-viral immune responses, respectively. Chemically modified mRNA (modRNA) can be effectively used to express reprogramming factors in somatic cells by escaping innate immunity signals and consequent marked interferon and cytokine release. To date, the most effective non-viral transfection of murine neonatal cardiomyocytes has yielded ~8% transfection efficiency.

Figure 9B:
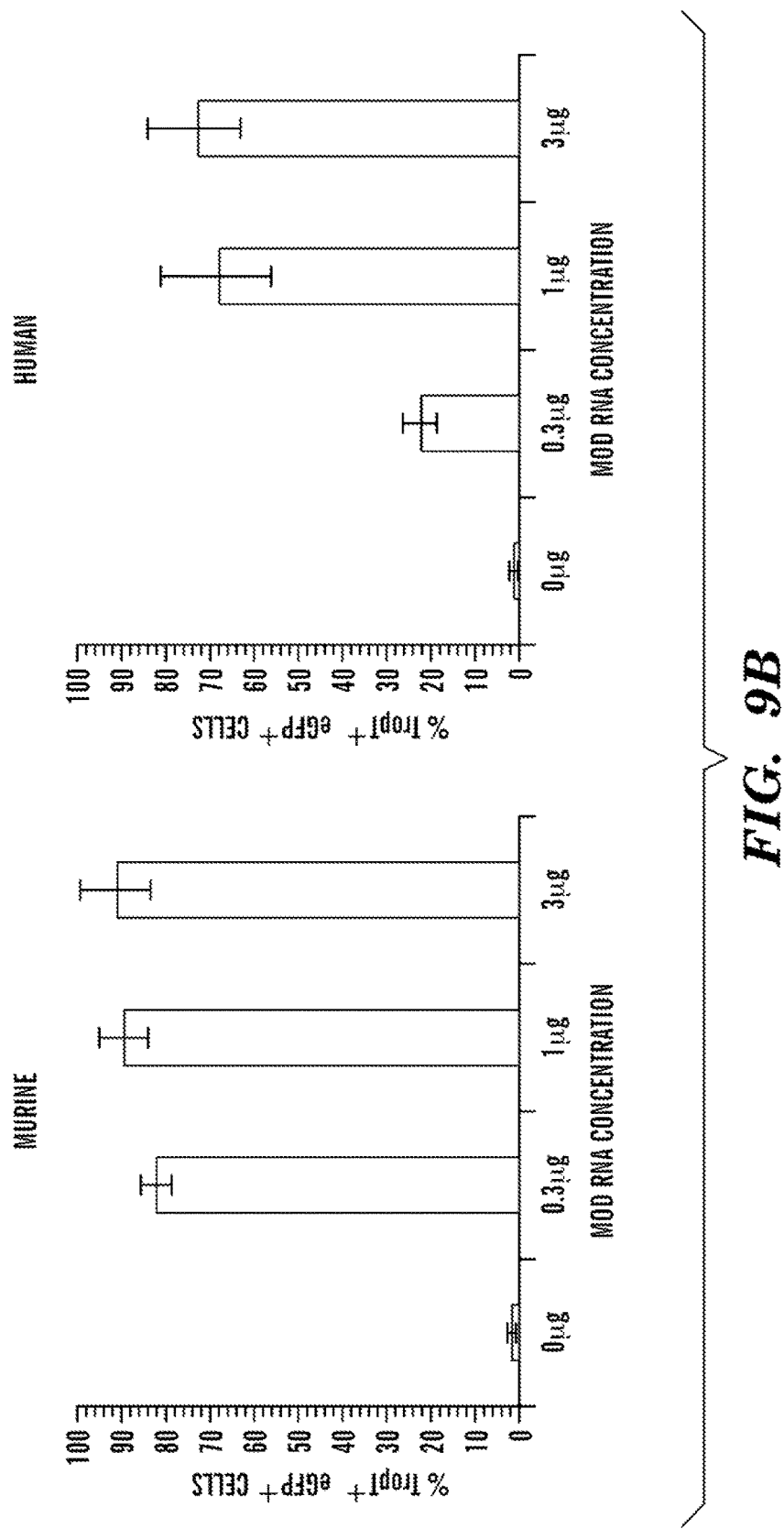
Figure 9C:
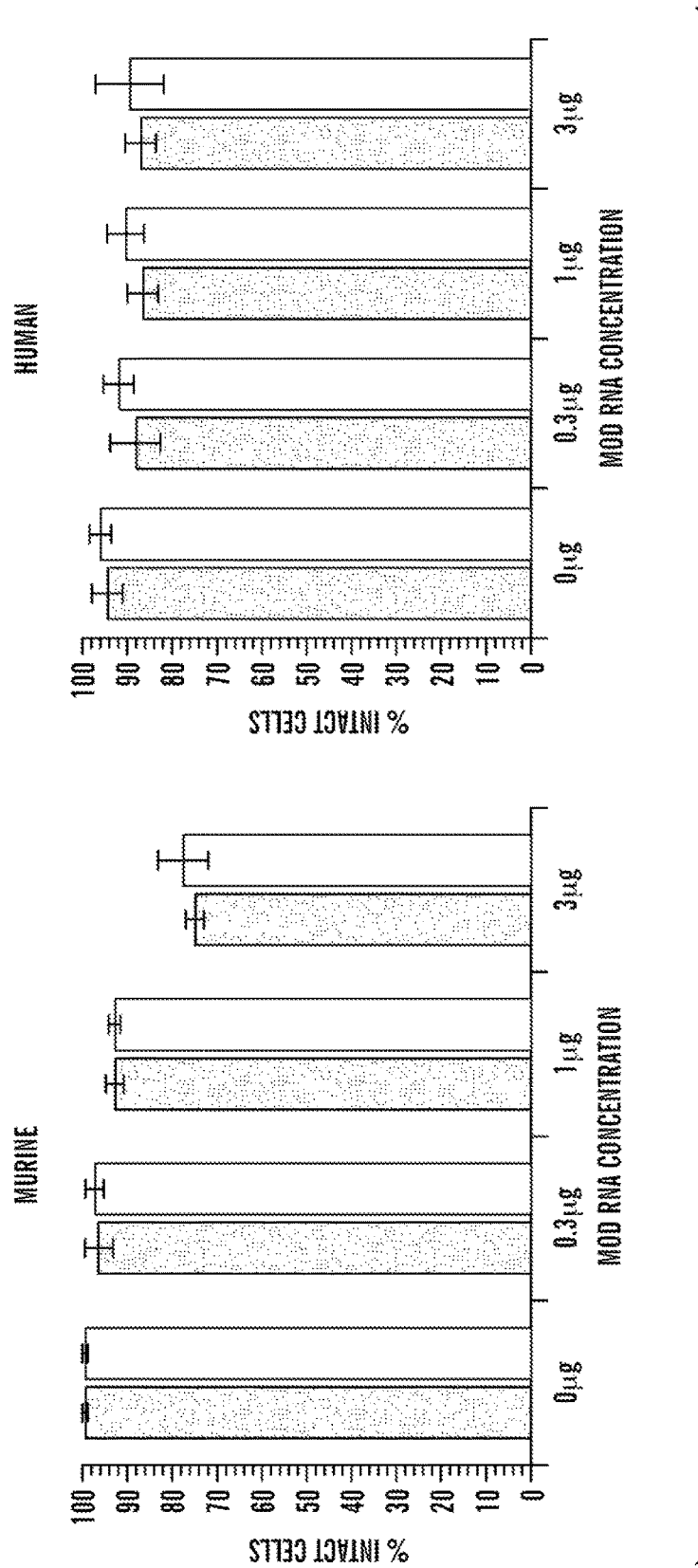
Figure 9D:
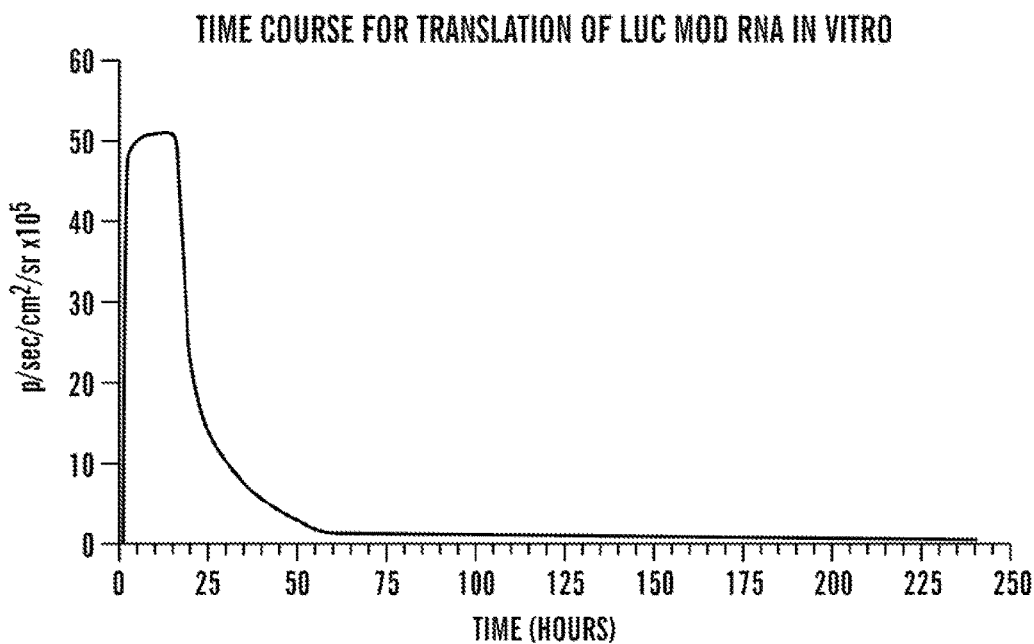
Figure 9E:
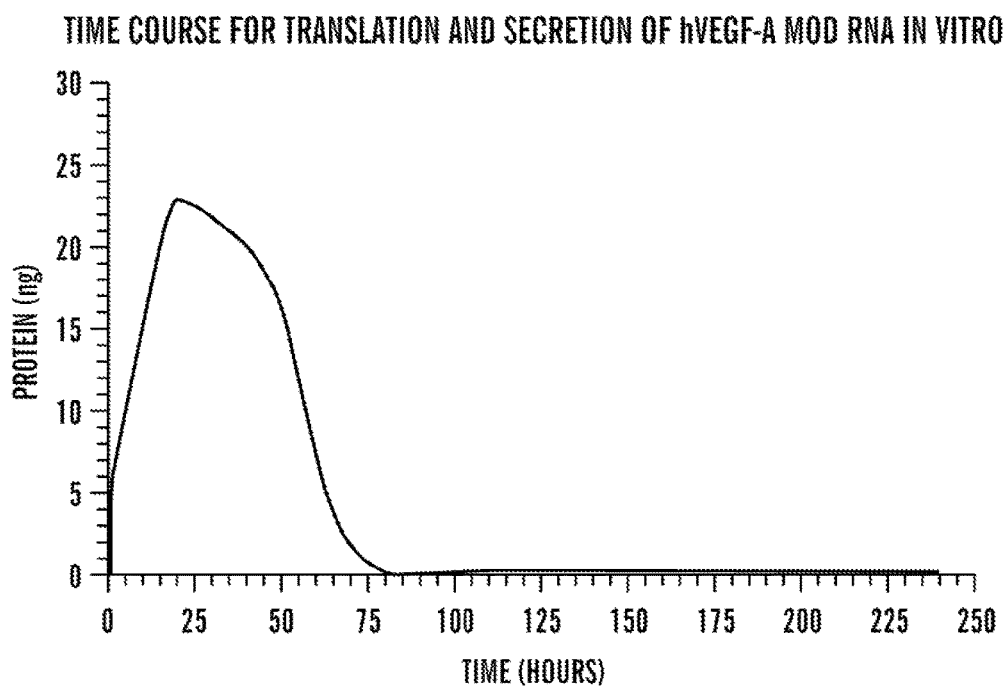
Figure 10A:
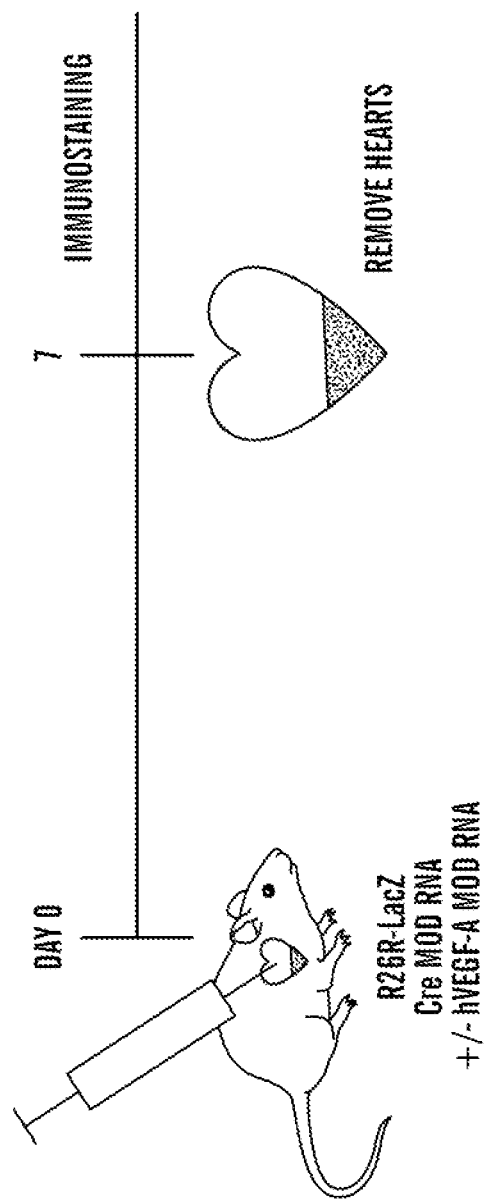
FIGS. 10A-10F show cardiac regeneration via hVEGF-A MOD RNA in adult hearts after MI.
Figure 10B:
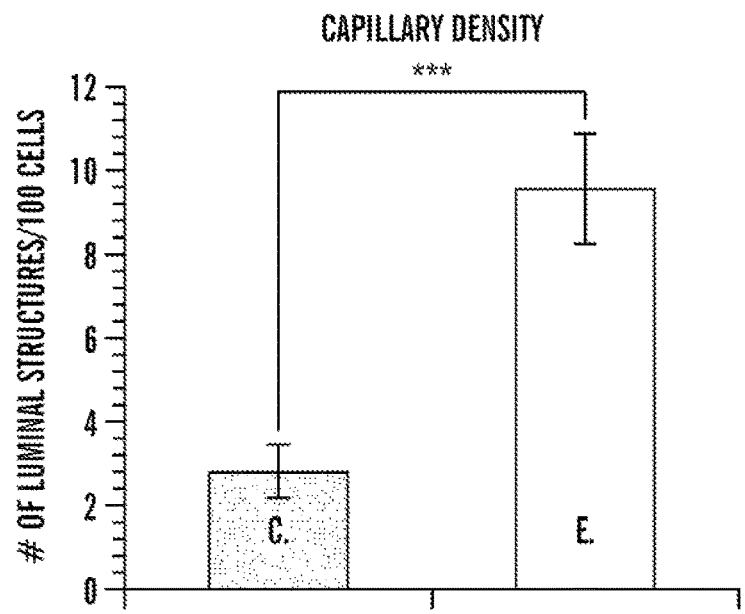
Figure 10C:
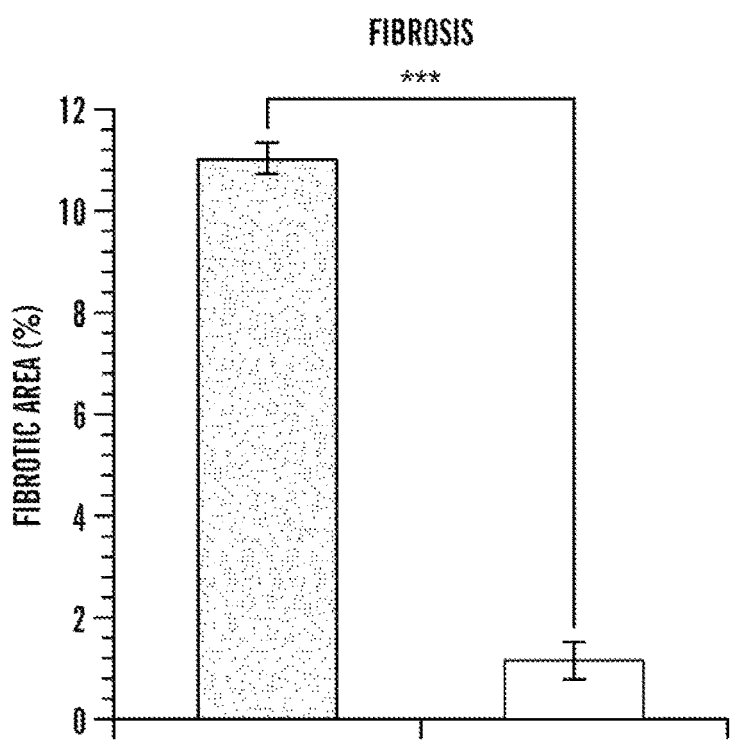
Figure 10D:
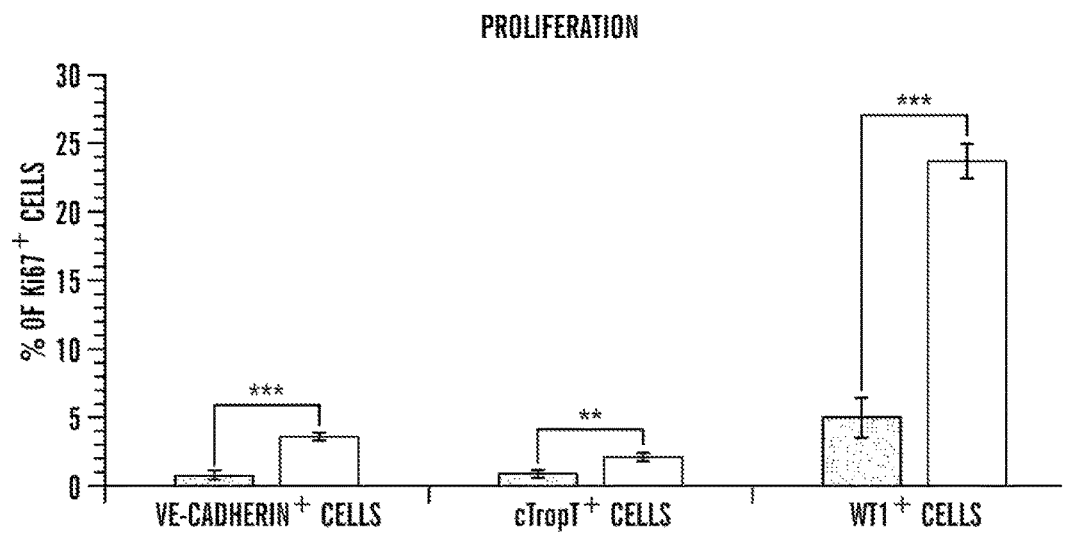
Figure 10E:
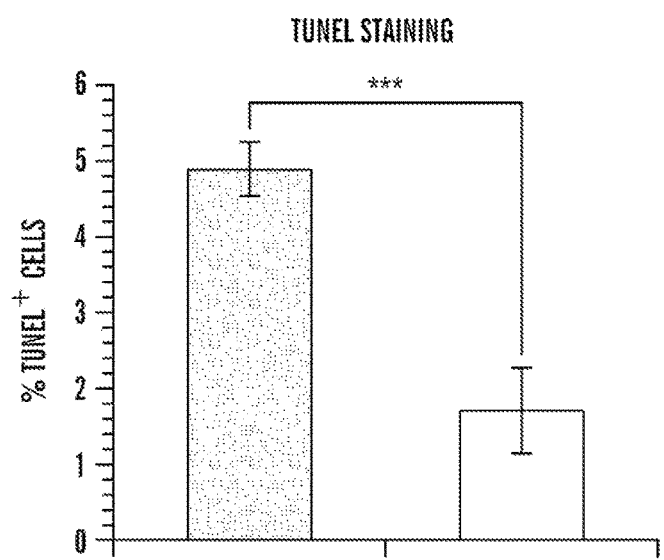
Figure 10F:
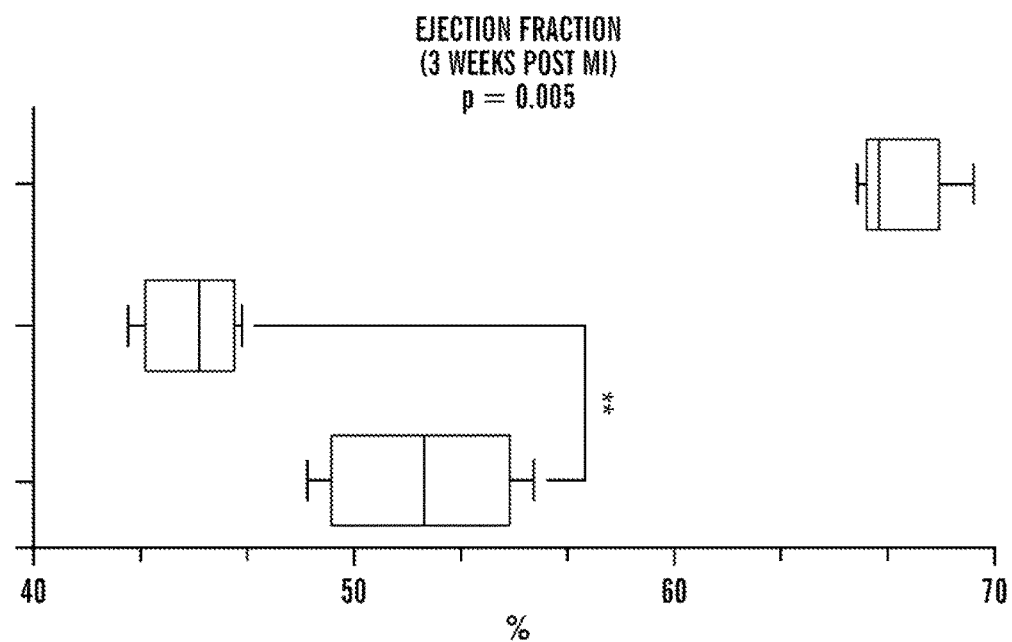

The inventors explored whether a non-viral modRNA approach would be advantageous in cardiomyocytes. Cardiomyocytes derived from both murine and human can be efficiently transfected with modRNA, with an efficiency of approximately 89 or 72%, respectively and with minimal toxicity (FIG. 9B). The time course for luciferase (Luc) expression (FIG. 9D) or hVEGF-A (FIG. 9E) were followed using a bioluminescence assay or ELISA assay for up to 100 hours. In the tube formation assay on fibronectin, it was observed that hVEGF-A may drive differentiation of cardiac cells into a endothelial cell fate in vitro (data not shown).

Figure 5B:
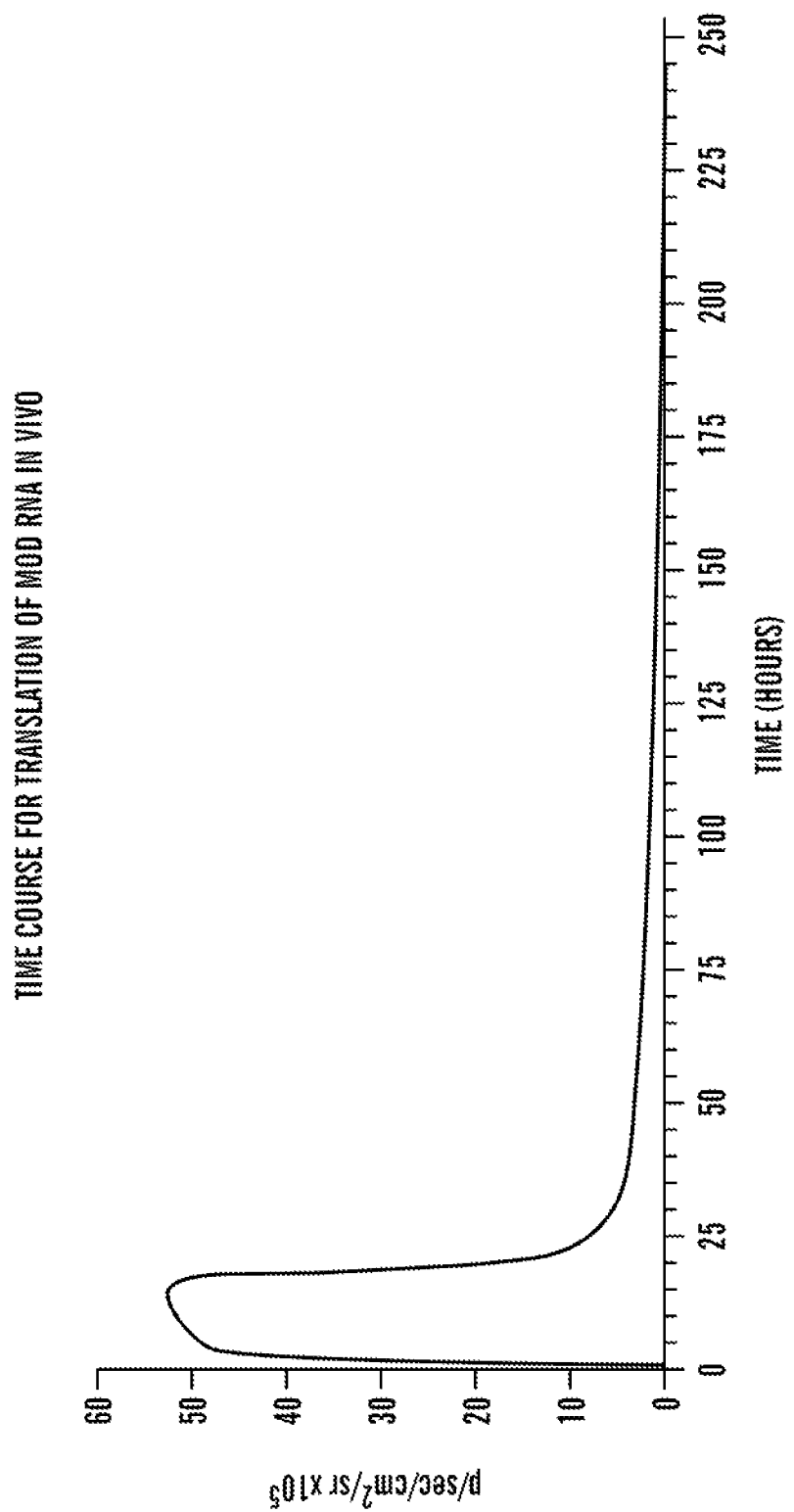

Moreover, transfecting human fetal cardiomyocytes with two distinct modRNAs resulted in co-transfection with both or none modRNA, showing that cells cannot distinguish between the different modRNA (data not shown). In vivo delivery of non-viral DNA plasmid resulted in a low cardiomyocytes transfection efficiency (~1%). Therefore, the transfection efficiency of cardiomyocytes with modRNA was examined in vivo. modRNA drives the time- and dose-dependent expression of the Luc reporter in the adult murine heart with just a single epicardial injection (data not shown). Expression could be detected by 3 hours, with a peak of a 50× fold increase at 24 hours, and returned to the baseline level by 72 hours (FIG. 5B).

Figure 12A:
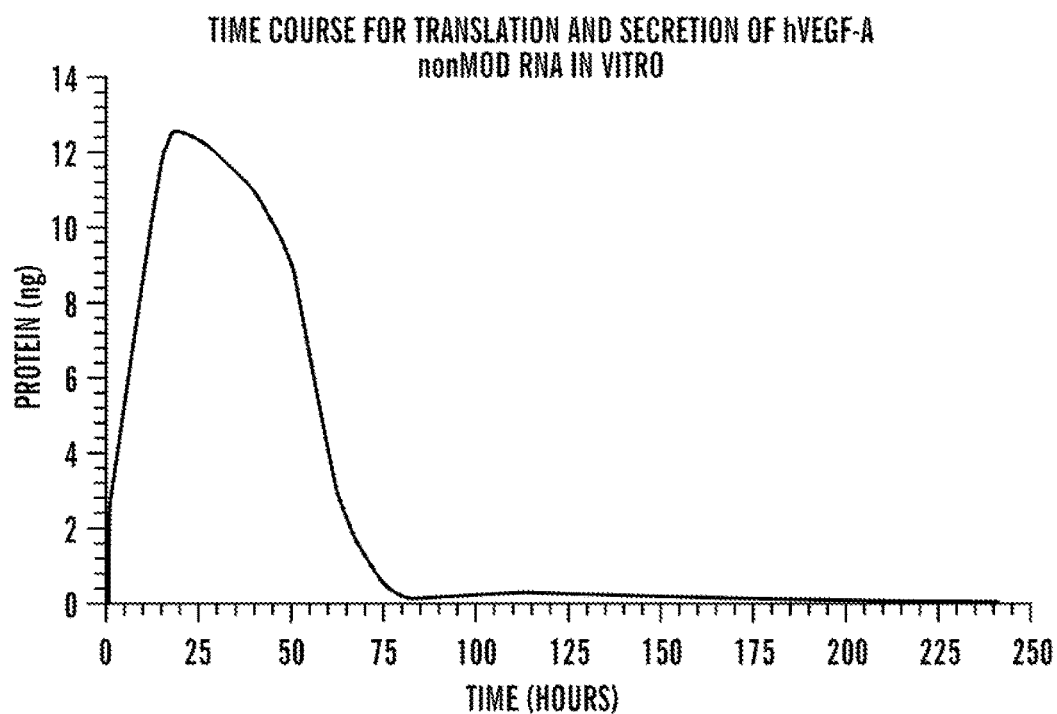
FIGS. 12A-12F show that hVEGF-A MOD RNA exhibits lower immunogenicity than the non-modified RNA.
Figure 12B:
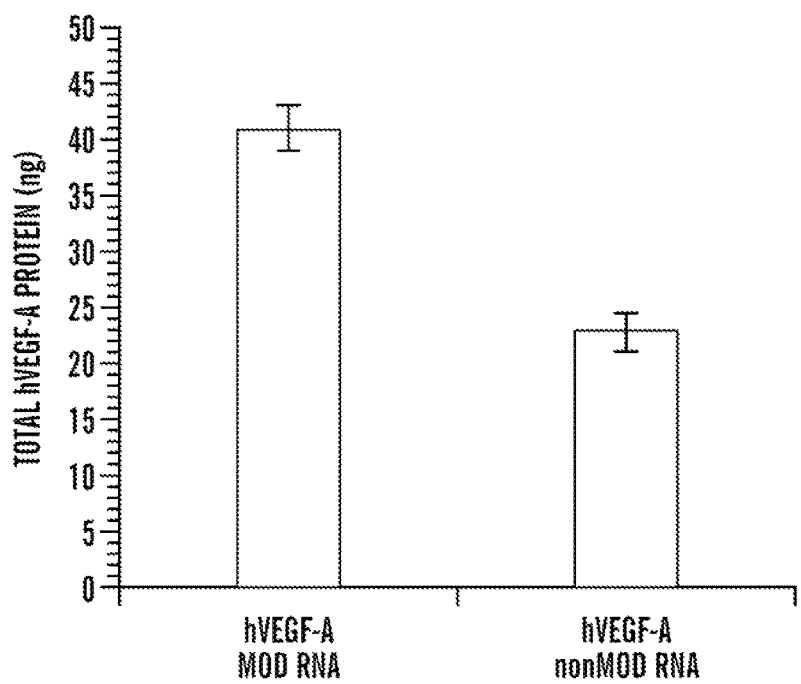
Figure 12C:
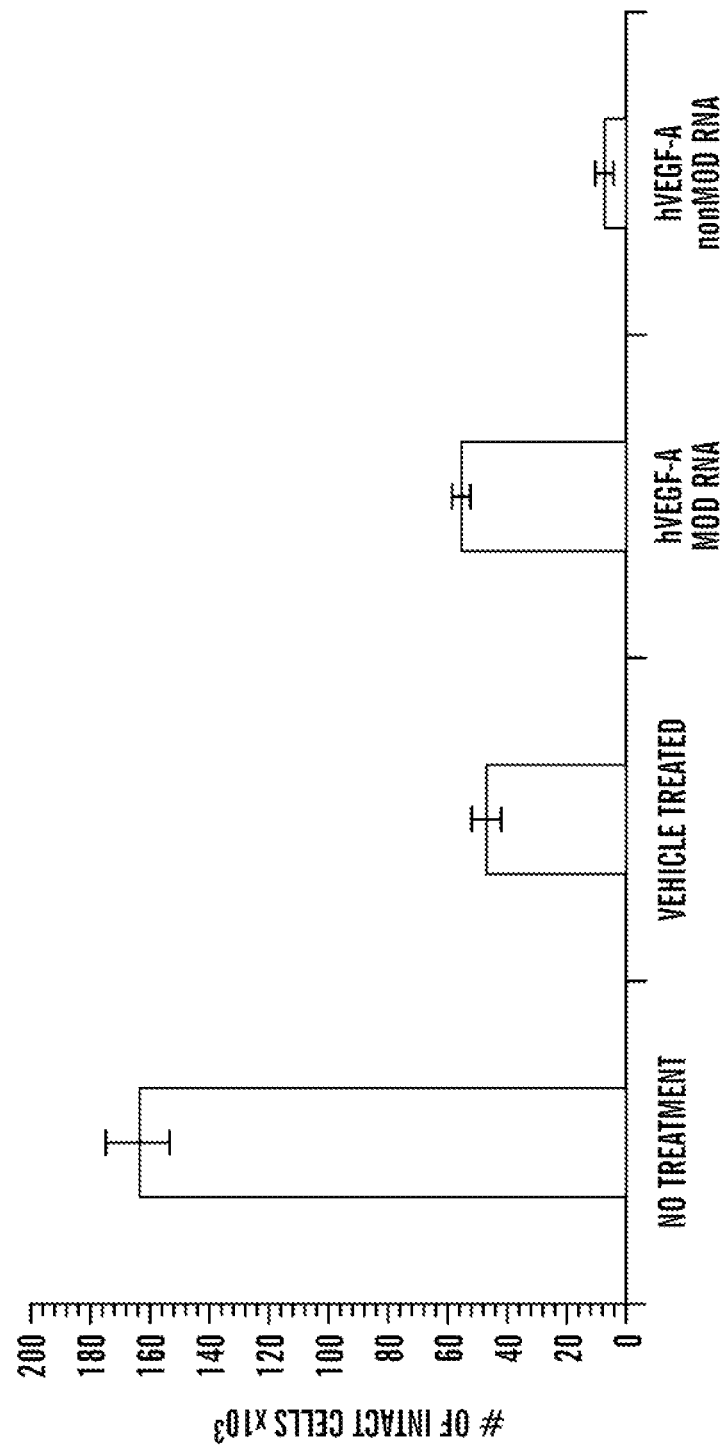
Figure 12D:
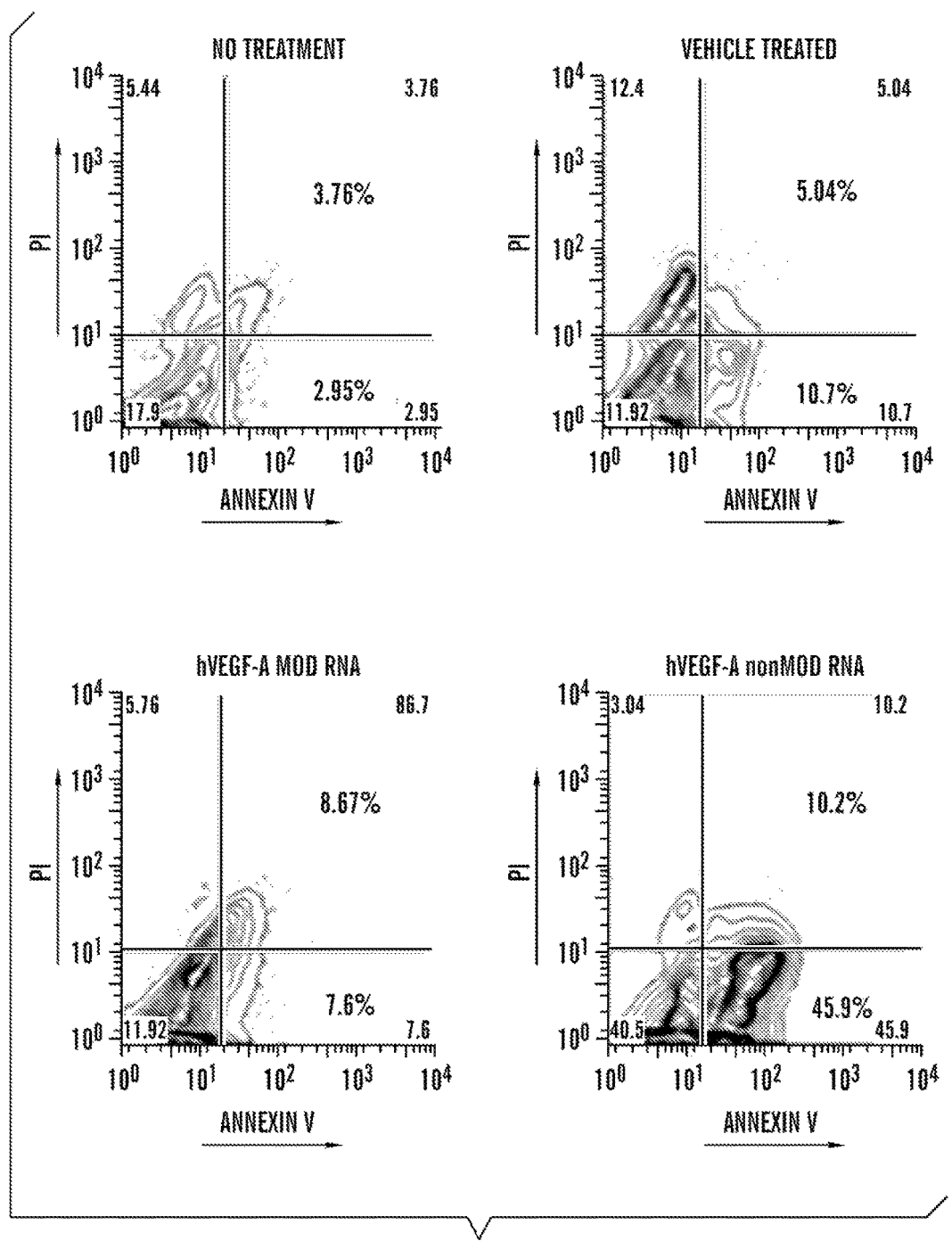
Figure 12E:
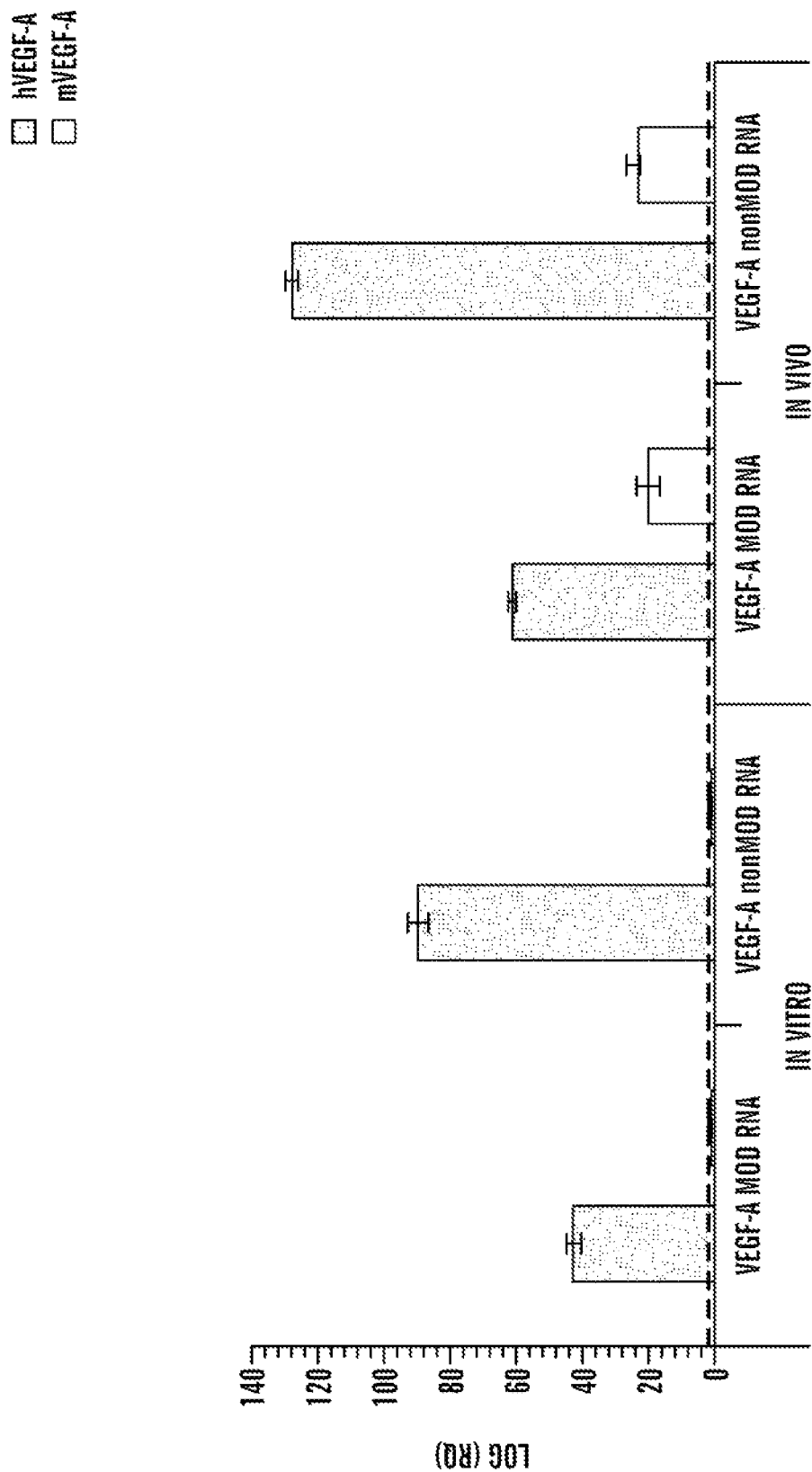
Figure 12F:
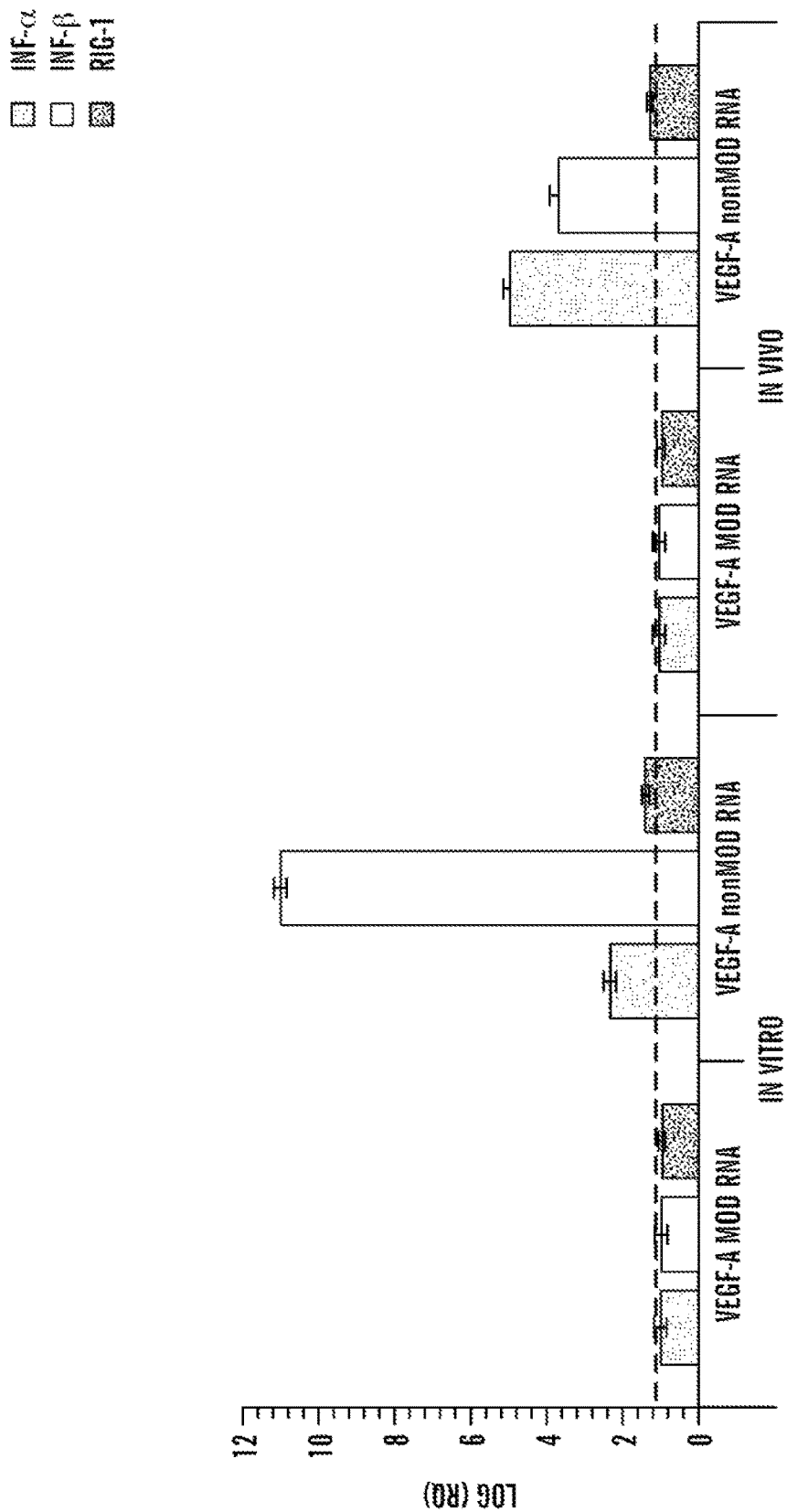

Injection of the Cre recombinase modRNA in ROSA26-LacZ mice (data not shown) revealed a remarkably high efficiency of uptake in around 15% of the left ventricle with a single epicardial injection, which are several orders of magnitude higher than the previous documented studies using naked nucleic acids and expression of foreign proteins was also low following intramyocardial injection. In addition, most cells in the area of injection, including cardiomyocytes (~80%) (data not shown), were transfected successfully with modRNA. The immunogenicity level of modRNA was examined and compared to non-modified mRNA (nonmod RNA) after transfection in vitro and in vivo. As shown in FIGS. 12A-12F, modRNA was less immunogenic compared to nonmodRNA in vitro and in vivo, which resulted in higher protein secretion and cell viability after transfection. In fact, nonmod RNA but not modRNA elicited an immune response and induced apoptosis via the secretion of interferons (IFN) such as IFN-a and IFN-b (FIGS. 12C and 12E). Taken together, these results indicate that an in vivo epicardial delivery of VEGF-A modRNA might lead to mobilization, expansion, and/or differentiation of rare heart progenitors following myocardial infarction (MI).

Three independent mouse model systems were utilized to determine the effects of VEGF-A modRNA on the ability to expand and drive rare heart progenitors into differentiated lineages and consequent cardiovascular regeneration. In Rosa26-LacZ mice, the role of hVEGF-A modRNA in cardiac regeneration was examined in vivo after MI. Delivery of hVEGF-A modRNA after MI resulted in a higher capillary density (d., 9.6 luminal structure per 100 cells were counted after injection of hVEGF-A modRNA compared with 2.7 in the vehicle-treated controls); less fibrotic area (d.1, 1.2% fibrotic area with hVEGF-A modRNA Vs. 11% in controls); enhanced proliferation of endothelial cells (3.7% VE-cadherin$^+$, Ki67$^+$ cells in hVEGF-A modRNA Vs. 0.9% in controls), cardiomyocytes (2.3% cTropT+, Ki67$^+$ cells in hVEGF-A modRNA Vs. 1.0% in controls i), and Wt1+ epicardial cells (23.6% WT1+ and Ki67$^+$ cells in hVEGF-A modRNA Vs. 4.9% in controls) (d.2); improved survival of cardiac cells (d.3, 1.7% TUNEL+ cells in hVEGF-A modRNA Vs. 4.8% in controls) (data not shown).

Figure 13A:
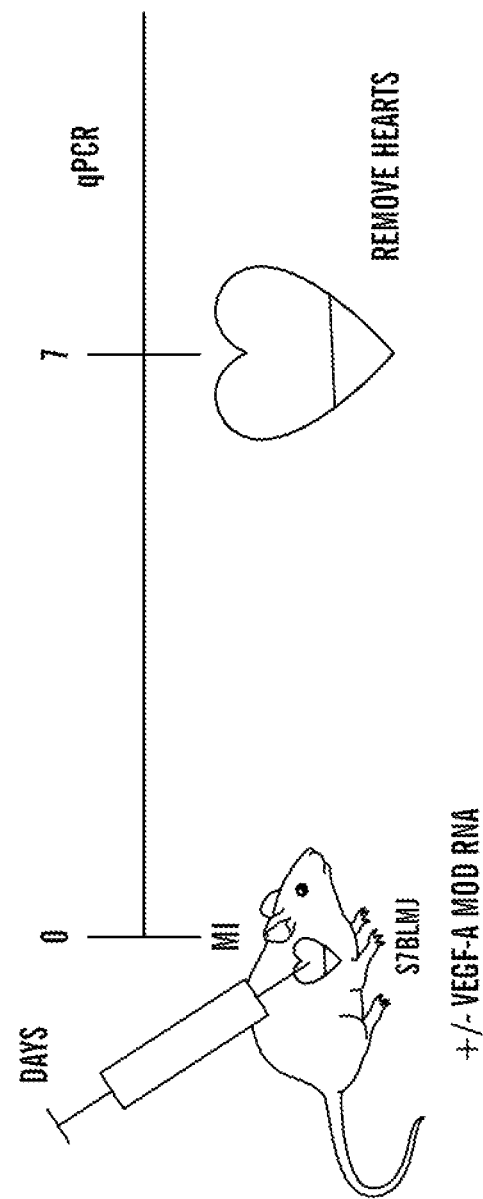
FIGS. 13A-13D show effects of delivery of hVEGF-A MOD RNA into murine hearts after MI results in upregulation of capillary density and reduction of fibrosis but not in sham hearts.
Figure 13B:
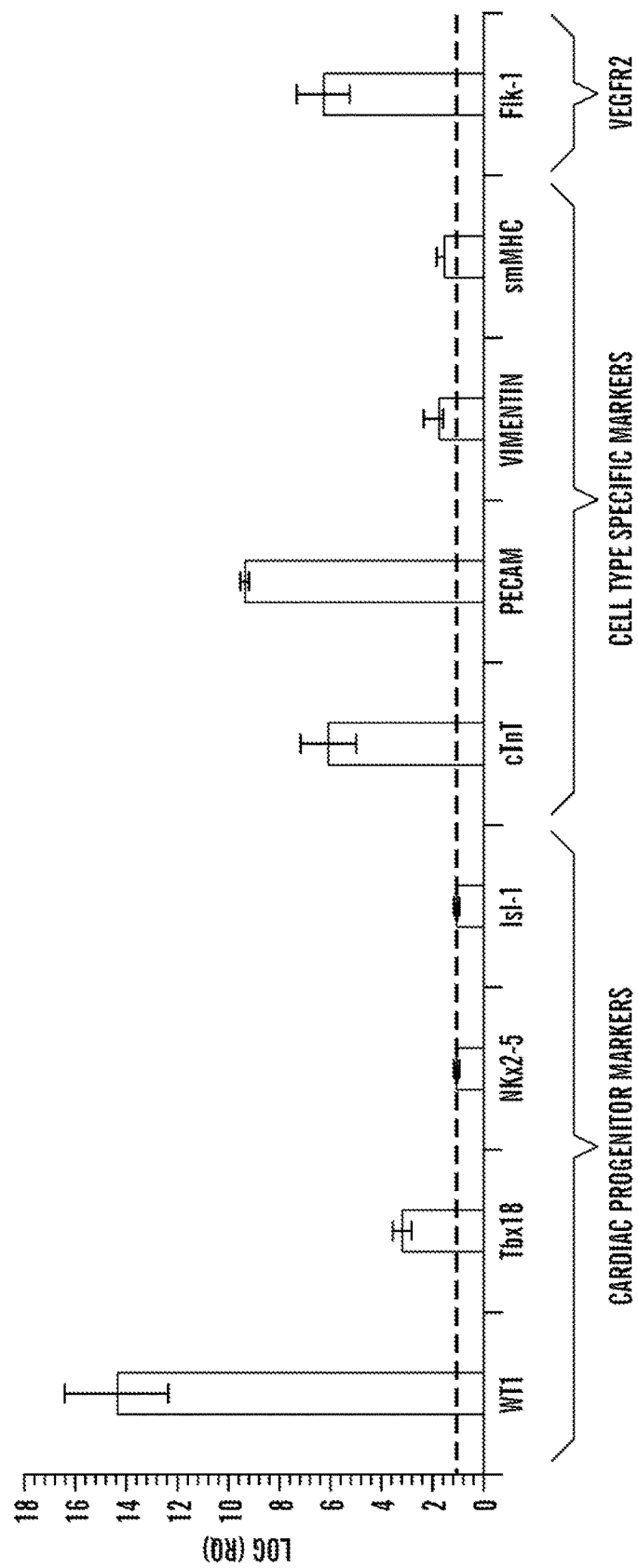
Figure 13C:
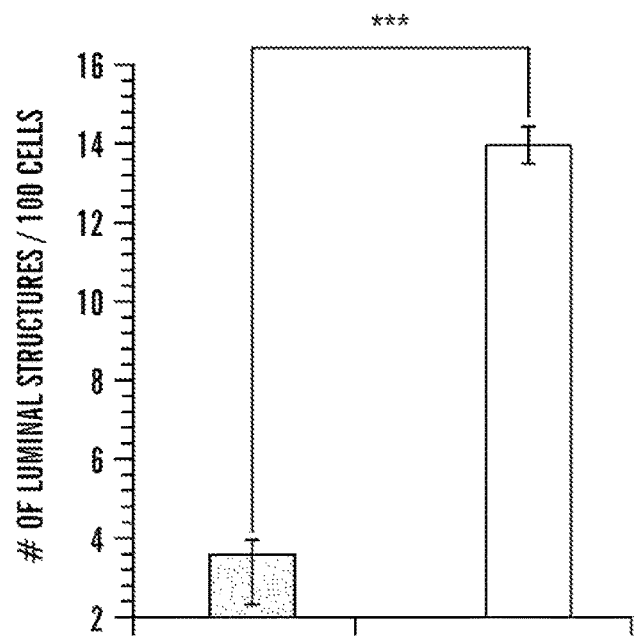
Figure 13D:
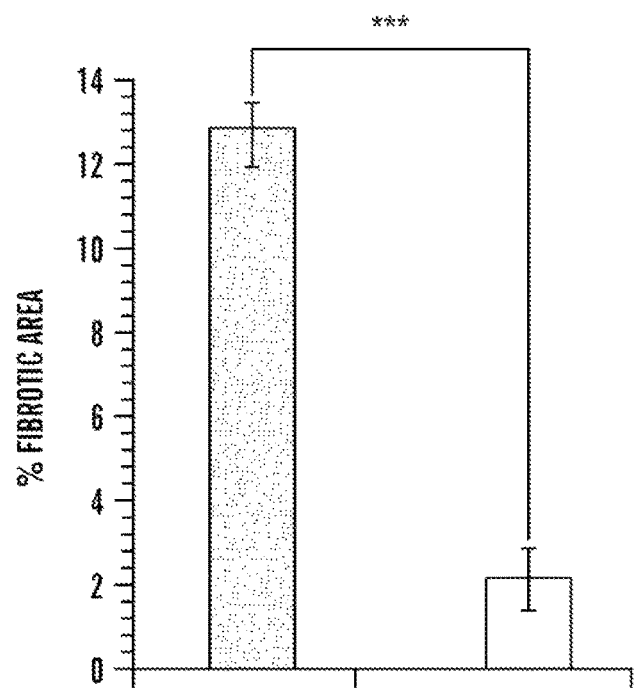

Moreover, the MRI results showed significant improvements in the ejection fraction (e, p=0.005) with 65.5% in sham controls (pericardium was opened but LAD was not ligated), 45% in vehicle-treated hearts and 52% in hVEGF-A modRNA-treated hearts). There was also better heart contraction performance after hVEGF modRNA treatment (data not shown). Furthermore, qPCR revealed a selective, 15 fold increase in WT-1 expression, with no change in other heart progenitor markers, such as Islet-1 and NKX2.5, suggesting that WT-1+ epicardial progenitors may be selectively activated (FIG. 13B). Also, PECAM ( ), Vimentin ( ) and collagen type I ( ) immunostaining indicated that VEGF-A mod RNA treated hearts have more endothelial-like cells and less fibrotic area in compared to vehicle-treated hearts (data not shown). The injection of hVEGF-A modRNA has little or no effect on the WT-1+ epicardial progenitor pool in the absence of MI, indicating a key requirement of injury itself to mobilize the WT-1 epicardial progenitors from their naturally occurring cardiac niche (data not shown).

Figure 11A:
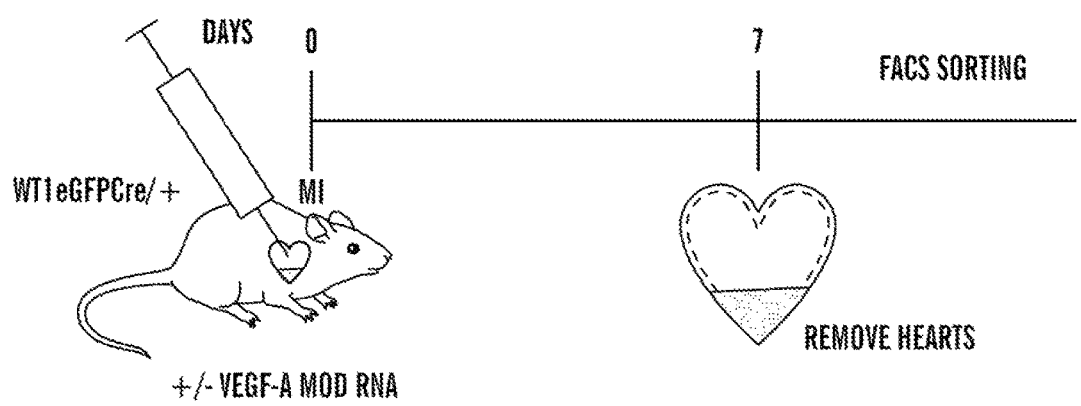
FIGS. 11A-11G show hVEGF-A MOD RNA induces proliferation and a cell fate switch of EPDCs toward the cardiovascular lineage. p<0.01; * p<0.001
Figure 11B:
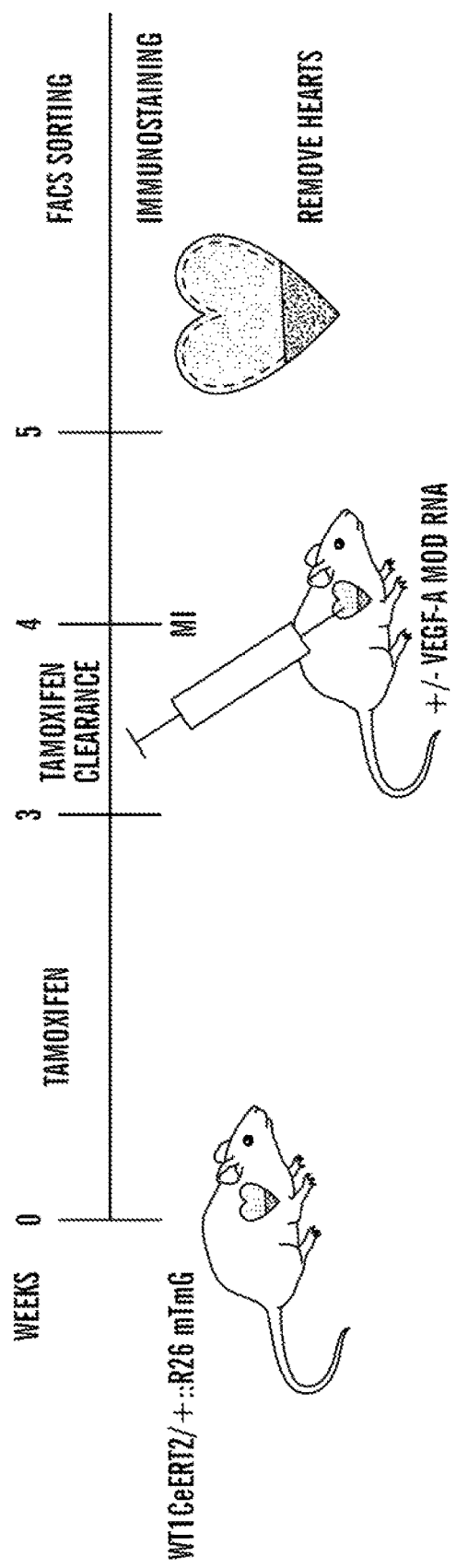
Figure 11C:
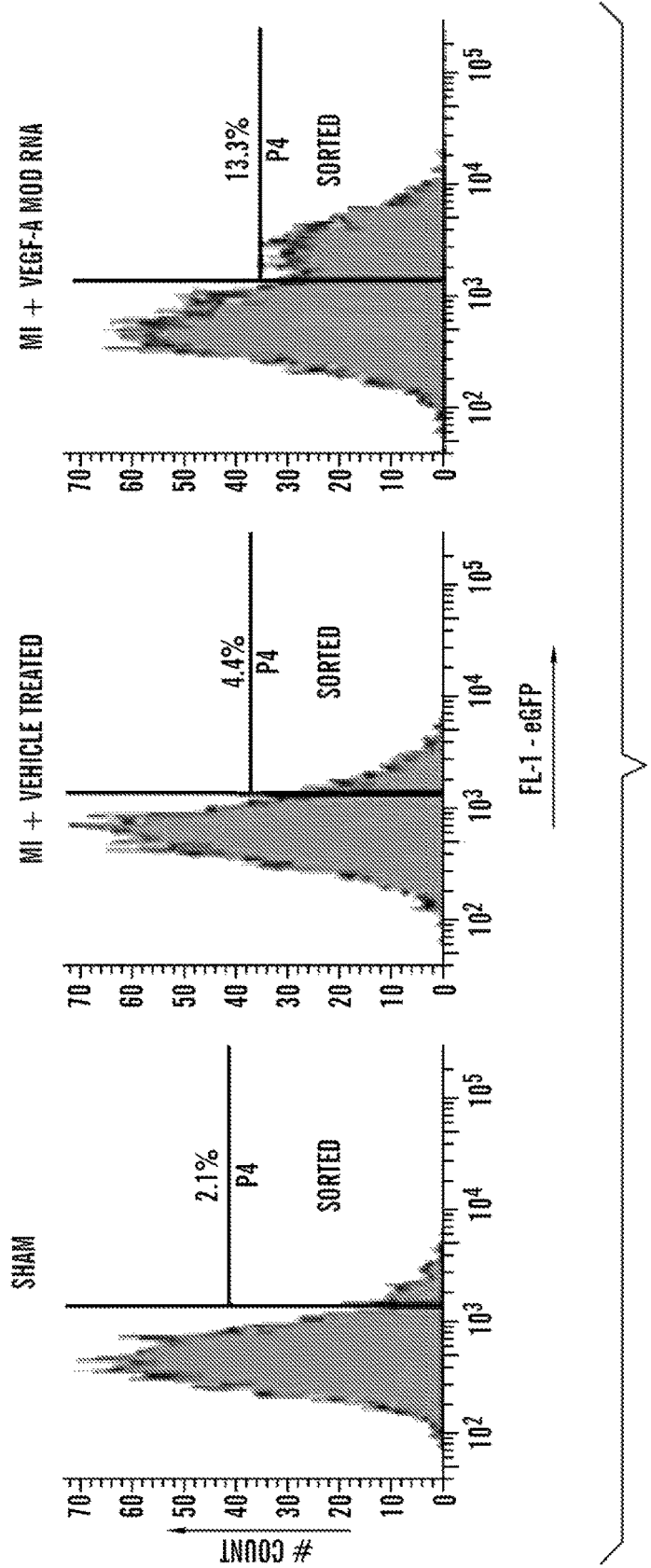
Figure 11D:
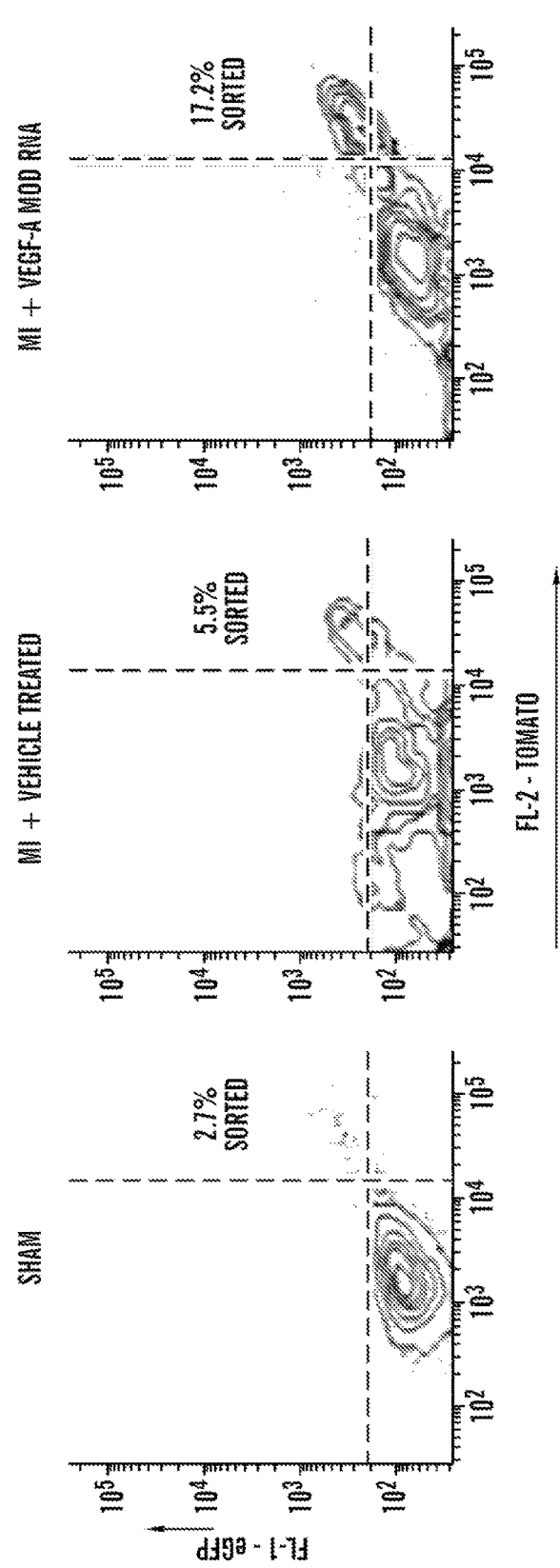
Figure 14A:
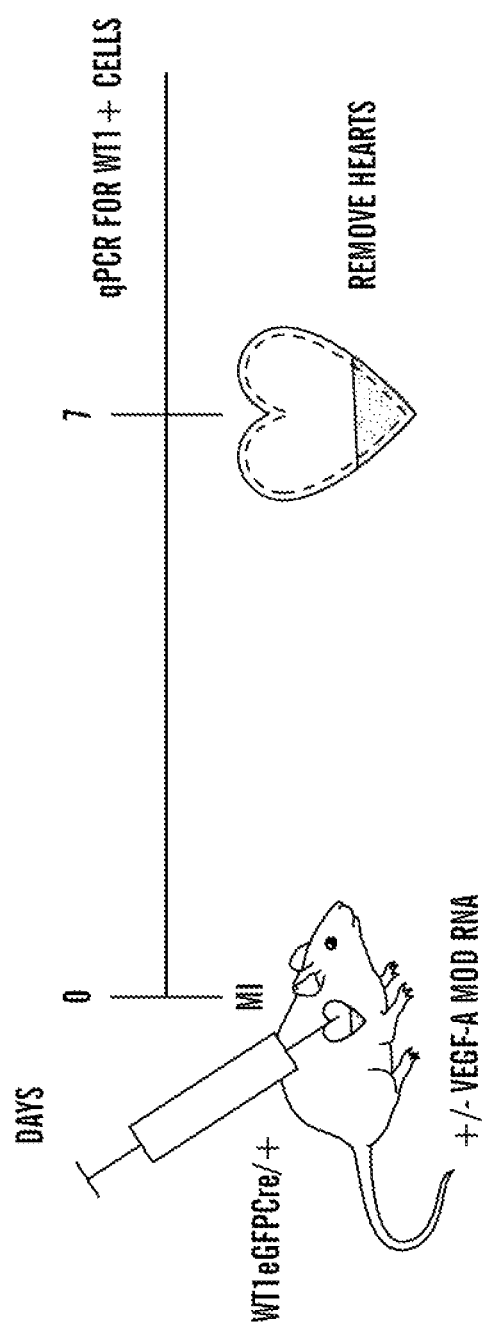
FIGS. 14A-14F show hVEGF-A MOD RNA induces cell fate switch of EPDCs from the fibroblastic lineage towards the cardiovascular lineage.
Figure 14B:
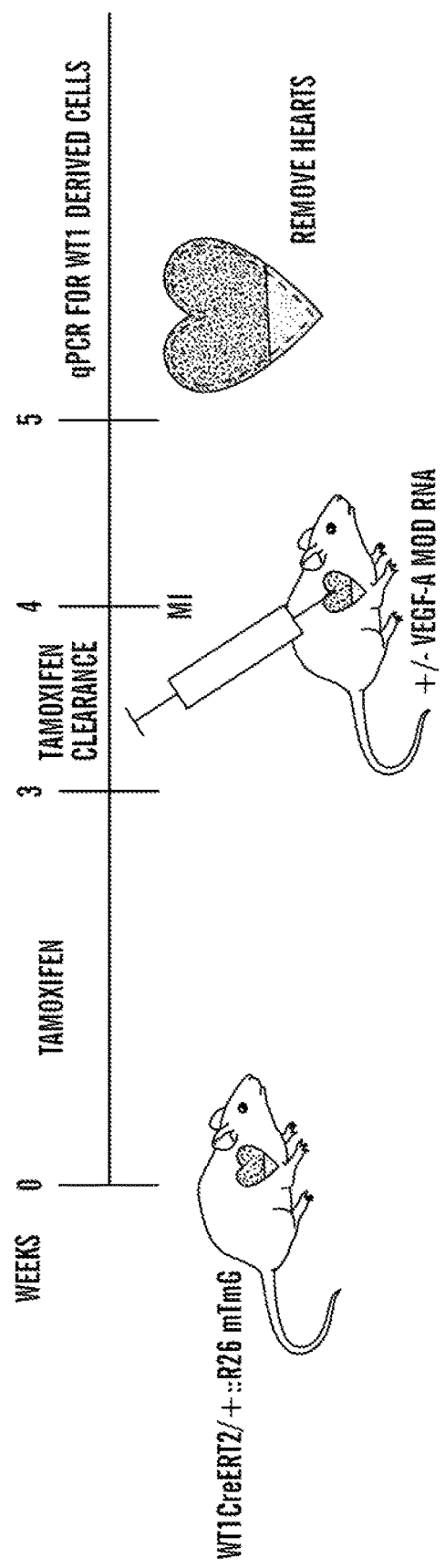
Figure 14C:
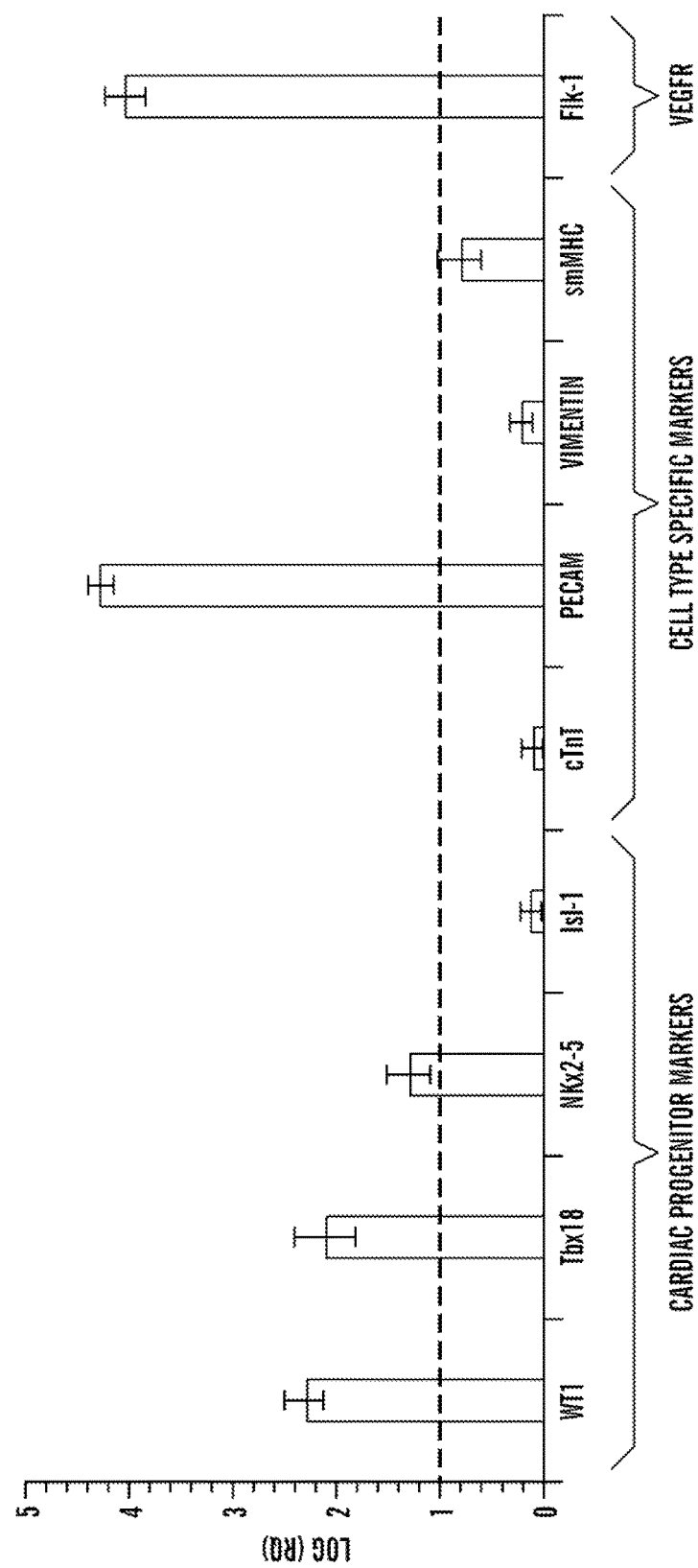
Figure 14D:
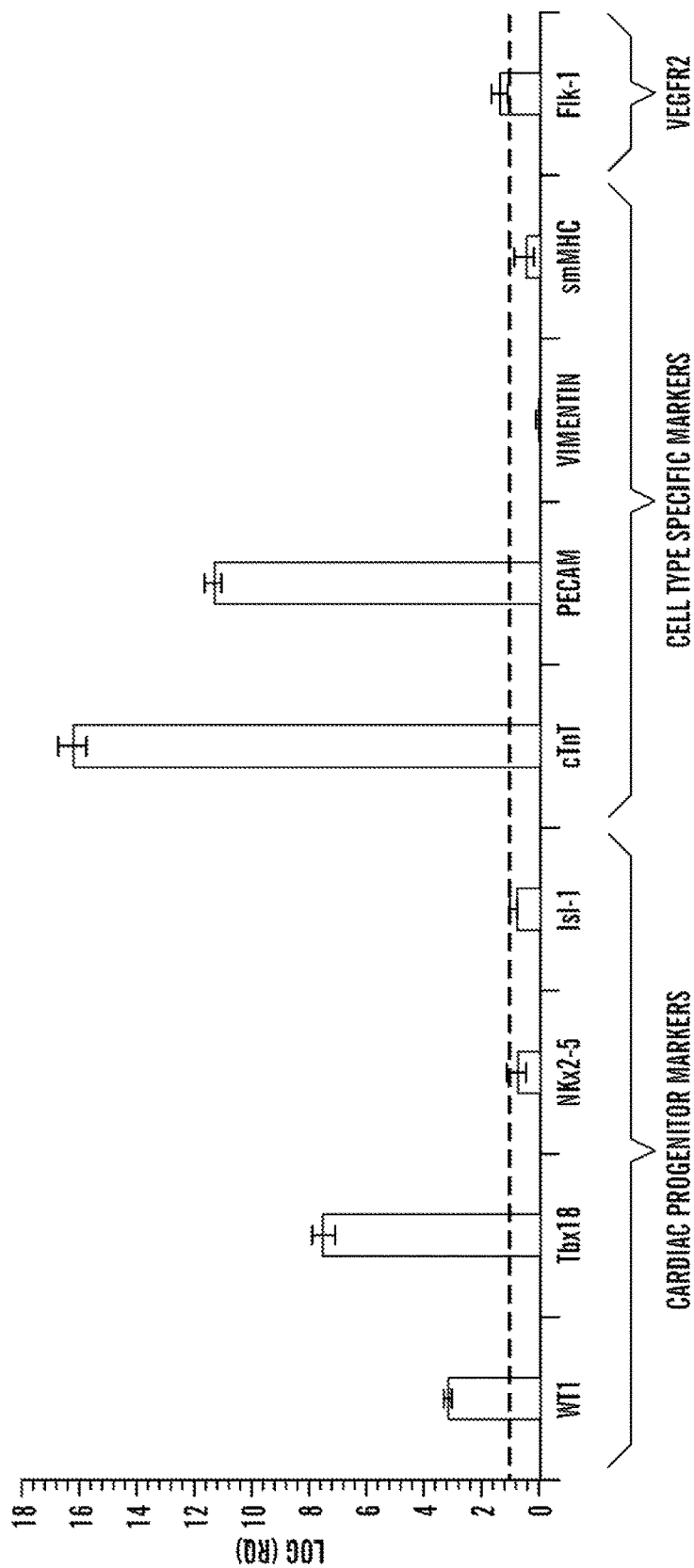
Figure 14E:
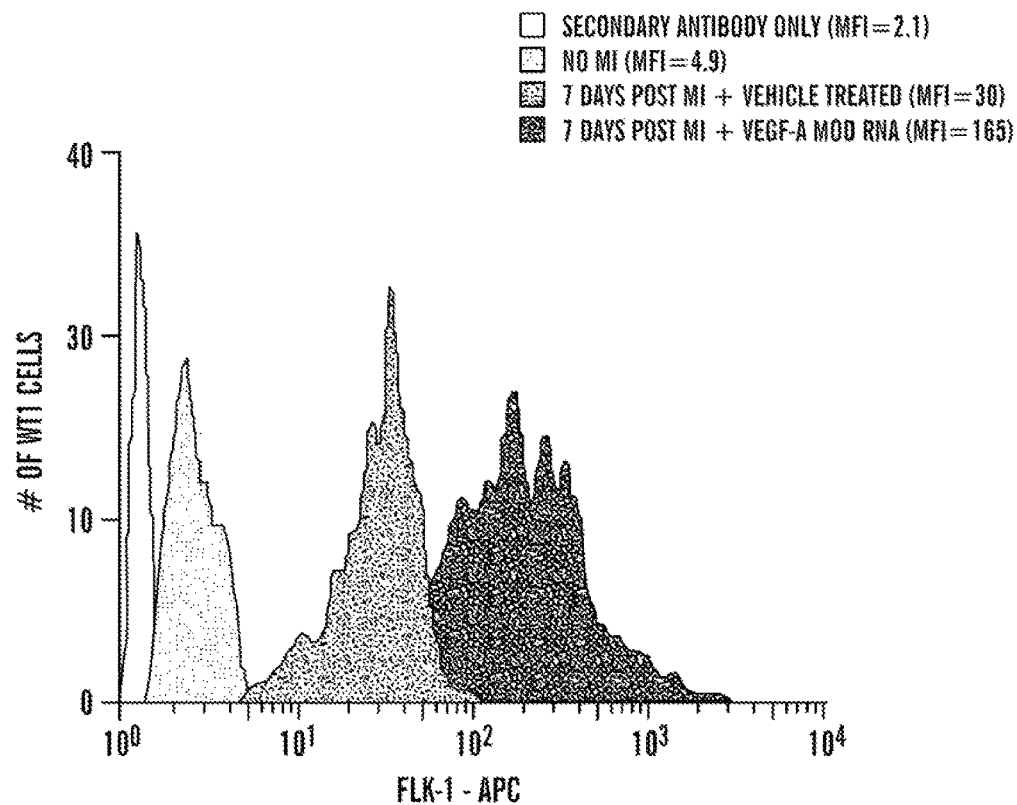
Figure 14F:
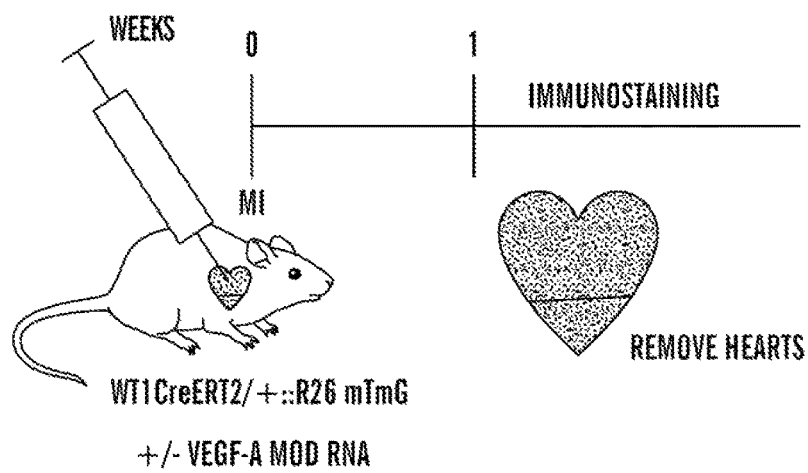

To directly document the ability of hVEGF-A modRNA to expand the number of WT-1+ cells, the inventors utilized mice which harbored a eGFP knock-in to the endogenous WT-1 locus. Following MI, the number of WT1+ cells doubled in compared to SHAM controls (FIG. 11C.1, 4.4% Vs. 2.1%). Moreover, upon MI and delivery of hVEGF-A modRNA, the number of WT1+ cells raised to 13.3% (~7 folds increase in compared to the SHAM controls). eGFP+ sorted cells were also examined using qPCR which showed an increase in expression of PECAM and Flk-1 and a reduction of vimentin in the WT1+ cells treated with hVEGF-A modRNA in compared to the vehicle-treated hearts (FIG. 14C). Furthermore, immunostaining of Flk-1 on the WT1+ cells revealed that WT1+ cells are also positive for the VEGF2 receptor upon delivery of hVEGF modRNA (FIG. 14E, 6 fold after MI in the vehicle-treated hearts vs. 33 fold after MI in the hVEGF-A modRNA-treated hearts).

Figure 4:
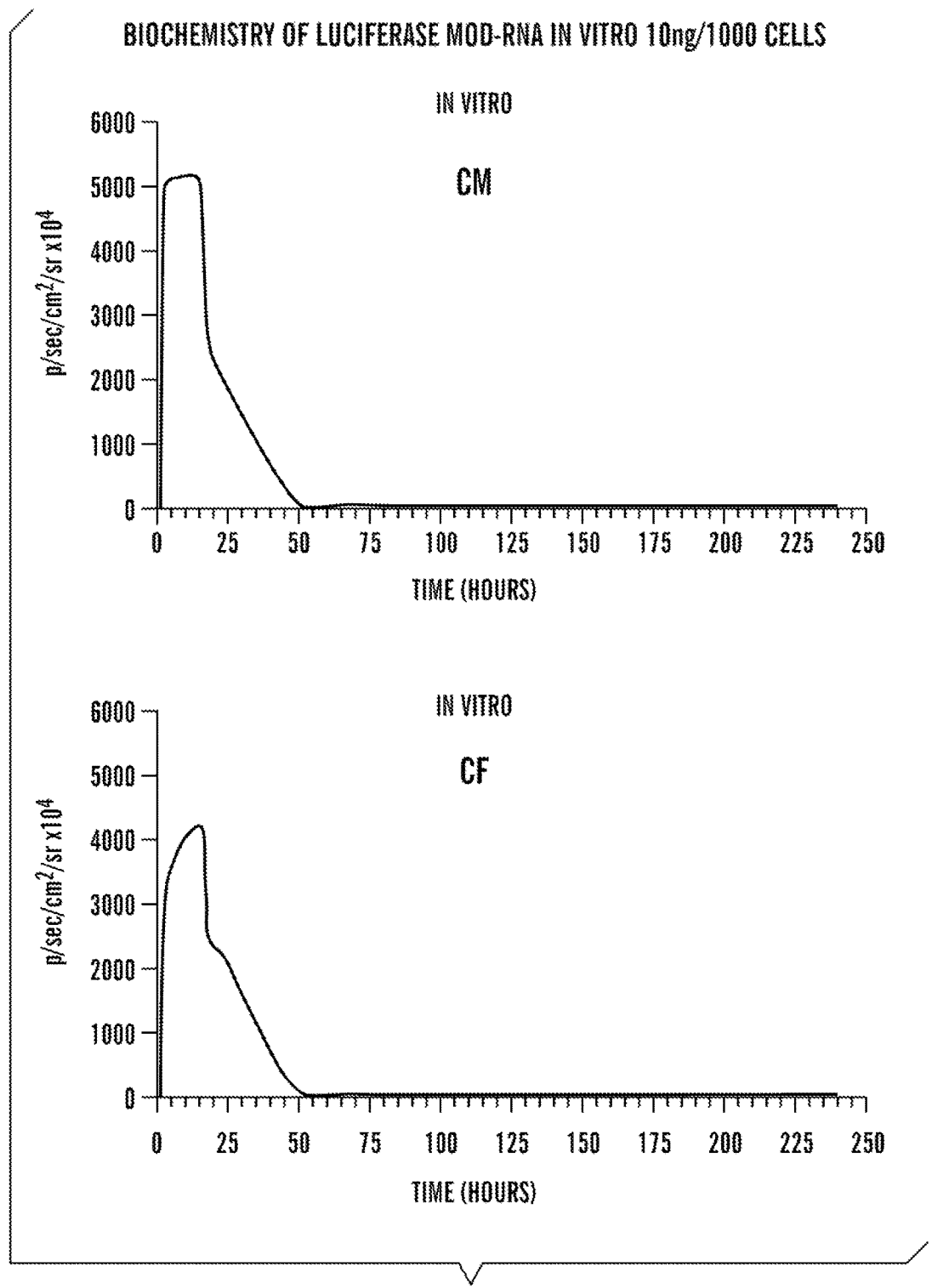
FIG. 4 shows in vitro transfection of luciferase MOD-RNA to mouse cardiomyocytes (CM) or cardiac-fibroblasts (CF). Neonatal mouse cardiomyocytes (CM) and cardio-fibroblasts (CF) were transfected in vitro with 1 μs per well (100000/well) Luciferase (Luc) MOD-RNA.
Figure 11E:
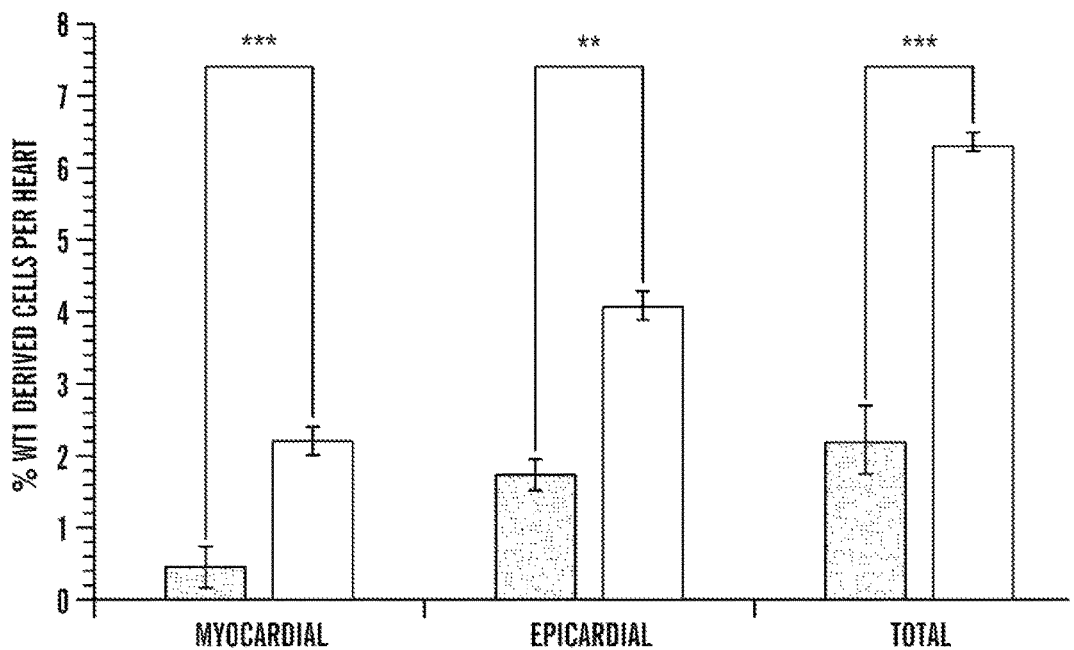

Using a similar approach, the inventors utilized the WT1 lineage tracing transgenic mice (Wt1/CreERT2/+::R26 mTmG) to study the cell fate of differentiated cells from the WT1+ epicardial progenitors upon in vivo delivery of modRNA. Following MI, the number of WT1 derived cells doubled in compared to the SHAM controls (FIG. 4 b.1, 2.7% Vs. 5.5%). In addition, upon MI and delivery of hVEGF-A modRNA, the number of WT1 derived cells raised to 17.4% (~6 fold increase in compared to the SHAM controls). eGFP+ sorted cells were examined using qPCR, which also showed increased expression of PECAM and cTropT with a reduction in expression of vimentin in the WT1 cells in hearts treated with hVEGF-A modRNA in compared to those treated with vehicle (FIG. 14D). hVEGF-A can directly lead to the expansion of WT-1+ heart progenitors and their subsequent conversion into the vascular endothelial cells in an in vitro human cardiogenesis model system, consistent with a direct effect as a progenitor cell fate switch. Indeed, immunostaining of the WT1 derived cells indicated a 3 fold increase in the number of WT1 derived cells upon delivery of hVEGF-A modRNA (data not shown). This increase was found on the epicardium (2 fold increase) and also in the myocardium (~5 fold increase; FIG. 11E). Double immunostaining for the WT1 derived cells with different markers showed that upon delivery of hVEGF-A modRNA, WT1+ cells may have differentiated into different cardiac cell types.

Previous studies have suggested that epicardial progenitors can be found in the post ischemic heart and they mostly contribute to fibroblasts and interstitial cells which maintain mostly on the epicardial surface. It is shown herein that hVEGF-A modRNA can mobilize these progenitors and change their cell fate toward a cardiovascular endpoint. The effects are associated with an increased conversion of WT-1 to all three major cardiovascular cell types (endothelial and vascular smooth muscle), and cardiomyocytes, with the former being the predominant response (FIG. 11). Due to the viable information received using the WT1 lineage tracing transgenic mice model (Wt1/CreERT2/+::R26 mTmG), the level of leakiness in the system was also examined. It was found that there might be a slight chance of 0.025%, if any, leakiness existed in this system (data not shown).

Figure 11F:
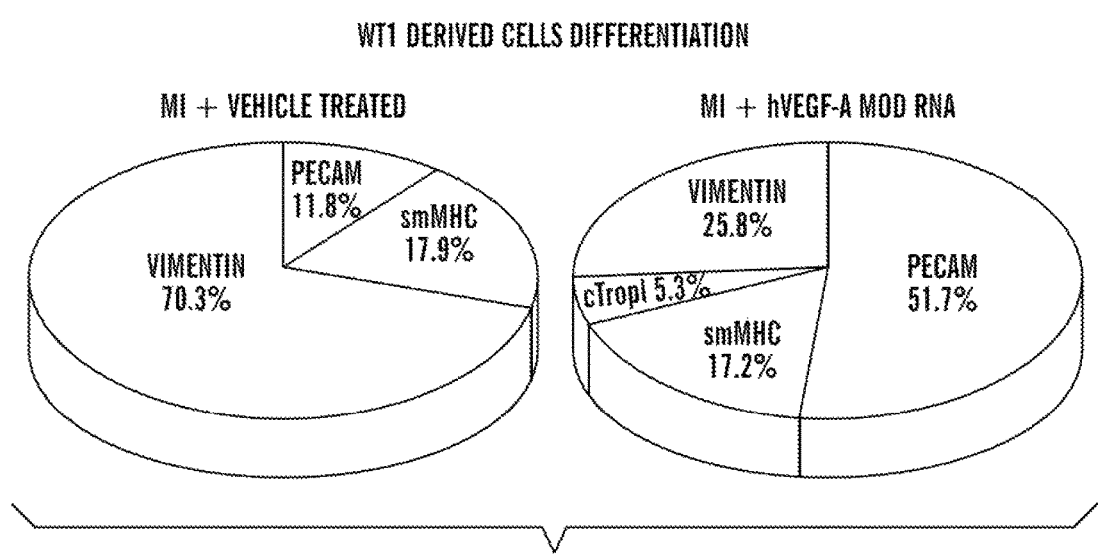
Figure 11G:
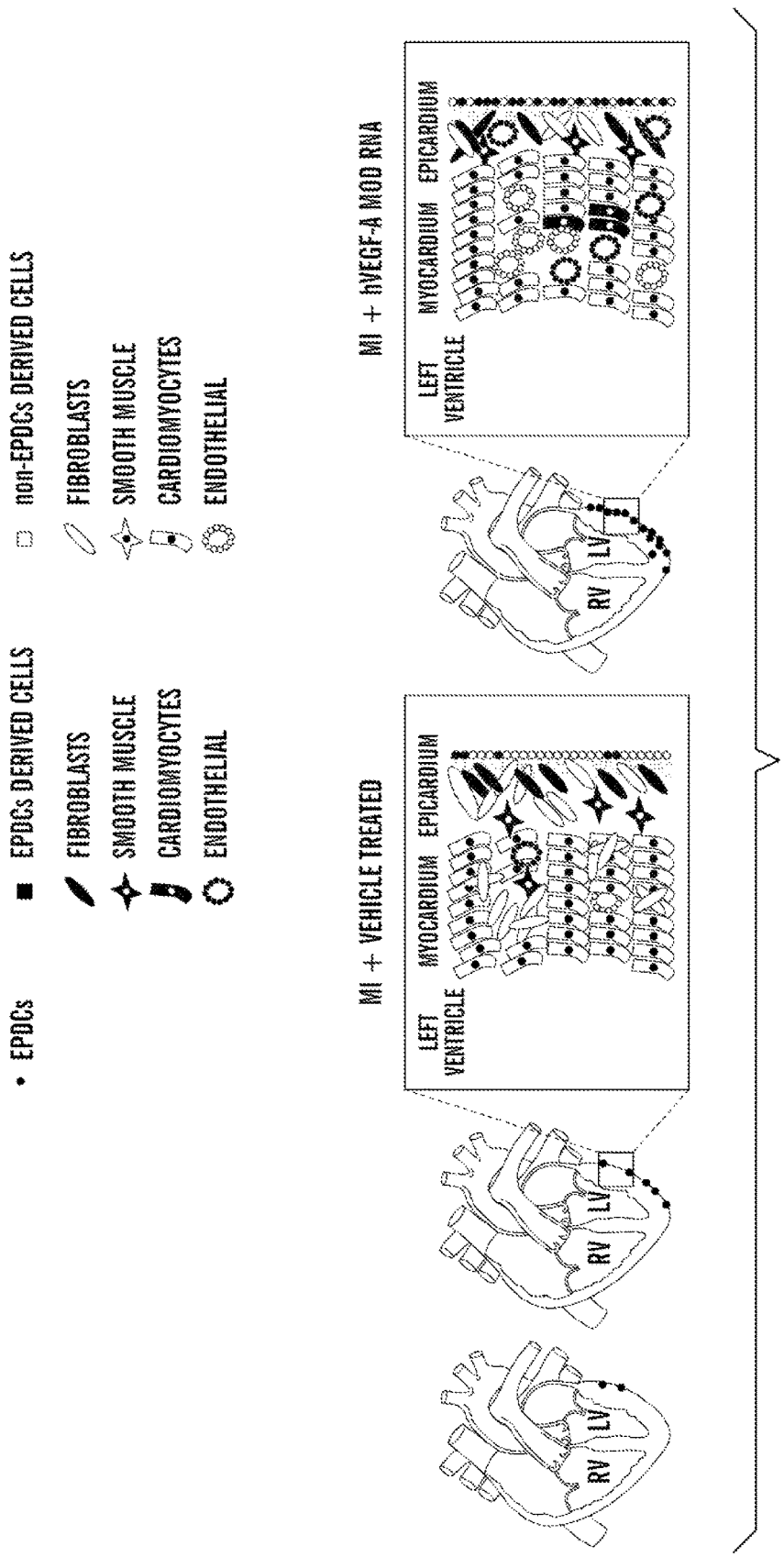

In summary, hVEGF-A modRNA seems to have a direct effect on expanding the pool of WT-1+ epicardial heart progenitors and switching their fate from an interstitial fibroblast response towards differentiated cardiovascular cell lineages, including cardiac, endothelial, and smooth muscle cells, following myocardial infarction (FIG. 11F). Accordingly, modRNA can identify endogenous paracrine therapeutic agents, and, in light of the routine ability to access the human epicardial surface via percutaneous catheter technology, represents a cell-free approach to drive rare heart progenitors towards a regenerative therapeutic response. It is also contemplated that these studies will permit parallel paracrine therapeutic approaches to drive regeneration of other solid organs and degenerative diseases.

Methods Summary

Construction of in vitro transcription templates and synthesis of MODRNA has been described previously and is known to one of skill in the art. Briefly, ORF PCRs were templated from plasmids bearing eGFP, mCherry, luciferase, Cre and hVEGFA. For in vivo experiments, Cre was used to label the injection sites of hVEGF in R261acZ mice after Xgal or β-galactosidase immunostaining. MODRNA was synthesized using the MEGAscript T7 kit (Ambion™) with a custom blend of 3'-0-Me-m7G(5')ppp(5')G ARCA cap analog, adenosine triphosphate and guanosine triphosphate, 5-methylcytidine triphosphate and pseudouridine triphosphate, and was treated with Antarctic Phosphatase to remove residual 5'-triphosphates. Cardiomyocytes isolated from the MLC2v-YFP mice and human fetal hearts were isolated for in vitro transfections with eGFP, mCherry, luciferase or hVEGFA MODRNA. Transfections of MODRNA were carried out with vehicle containing RNAiMAX (Invitrogen™) and Opti-MEM™ medium.

Wt1eGFPCre/+ mice have been described previously. The inducible Wt1/CreERT2/+::R26 mTmG mice were generated by crossing Rosa26R-mTmG mice with Wt-1Cre-ERT2/+ mice. WO expression in adult epicardium was achieved through daily intraperitoneal injection of 4 mg tamoxifen 2-3 weeks before myocardial infarction (MI). MI was induced through permanent left anterior descending artery (LAD) ligation in adult R261acZ, Wt1eGFPCre/+ or Wt1/CreERT2/+::R26 mTmG mice, and vehicle or hVEGF-A modRNA was given at the same time post-MI. Hearts were digested with collagenase II, GFP+ cells quantified (FACS Aria II) and Flk-1 expression determined (FACS Aria II). Vehicle- or hVEGFA-treated hearts, harvested at 7, 14 or 28 days post-MI, were processed for immunofluorescence. Immunofluorescence quantification was performed on cryosections of post-MI hearts using ImageJ™. Total RNA, isolated from post-MI hearts of the injection area, of the FACS-sorted GFP+ cells from the Wt1eGFPCre/+ or Wt1/CreERT2/+::R26 mTmG mice was reverse transcribed for real-time qPCR using SYBR Green™ with Gapdh and bActin as endogenous controls. Fold-change was determined by the 22DDCT method and presented relative to the vehicle-treated hearts. MRI analyses were performed on days 7 and 21 post-MI of the R261acZ mice injected either with vehicle or hVEGFA modRNA to determine temporal changes in infarct size and cardiac function.

Methods

Construction of IVT Templates and Synthesis of modRNA. Production of in vitro transcription (IVT) template constructs and subsequent RNA synthesis have been described previously. The oligonucleotide sequences were synthesized by Integrated DNA Technologies™ (Coralville). Open reading frame (ORF) PCRs were templated from plasmids bearing eGFP, mCherry™, luciferase, Cre and human VEGF-A from Addgene™. PCR reactions were performed with HiFi Hotstart™ (KAPA Biosystems™) according to the manufacturer's instructions. Splint-mediated ligations were carried out with Ampligase™ Thermostable DNA Ligase (Epicenter Biotechnologies™). UTR ligations were conducted in the presence of 200 nM UTR oligos and 100 nM splint oligos. All intermediate PCR and ligation products were purified with QIAquick™ spin columns (Qiagen™) before further processing. Template PCR amplicons were subcloned with the pcDNA 3.3-TOPO TA cloning Kit™ (Invitrogen™) Plasmid inserts were excised by restriction digest and recovered with SizeSelect™ gels (Invitrogen™) before being used to template tail PCRs. RNA was synthesized with the MEGAscript™ T7 kit (Ambion™), with 1.6 mg of purified tail PCR product to template each 40 mL reaction. A custom ribonucleoside blend was used comprising 30-O-Me-m7G(50)ppp(50)G ARCA cap analog (New England Biolabs™), adenosine triphosphate and guanosine triphosphate (USB), 5-methylcytidine triphosphate and pseudouridine triphosphate (TriLink Biotechnologies™). Final nucleotide reaction concentrations were 6 mM for the cap analog, 1.5 mM for guanosine triphosphate, and 7.5 mM for the other nucleotides. RNA was purified with Ambion™ MEGAclear™ spin columns and then treated with Antarctic Phosphatase (New England Biolabs™) for 30 min at 37 C to remove residual 50-triphosphates. Treated RNA was repurified, quantitated by Nanodrop™ (Thermo Scientific™).

modRNA Transfection. modRNA transfections were carried out with RNAiMAX™ (Invitrogen™). modRNA and reagent were first diluted in Opti-MEM™ basal media (Invitrogen™). 100 ng/mL modRNA was diluted and 5 mL of RNAiMAX™ per microgram of MODRNA was diluted, then these components were pooled and incubated 15 min at room temperature before being dispensed to culture media. MODRNA transfections were performed in Opti-MEM™ plus 2% FBS for all in vitro experiments and in Opti-MEM™ alone for all in vivo experiments.

Murine and Human Primary Cell Isolation and Culture. MLC2v-YFP mice have been described previously. Murine neonatal and human fetal hearts were dissociated to single cells by collagenase II (Sigma™) as described previously. Cardiac cells were cultured in DMEM containing 5% FBS, 10% horse serum and 1 ug/ml insulin. Murine adult hearts were digested using collagenase IV (Sigma™) and cardiac cells were cultured in Mesenchymal Stem Cell Growth Medium (Lonza™) containing 10% FBS. Transfection of these cardiac cells with eGFP, mCherry™, luc or hVEGF-A MODRNA was performed using a vehicle containing a mixture of RNAiMAX™ (Invitrogen™) and Opti-MEM™ basal media. Secretion of the translated hVEGF-A proteins was quantified using ELISA (R&D Systems™). All cardiac cells resemble endothelial cells after transfection with hVEGF-A modRNA (1 μg) whereas the vehicle-treated cells failed to adopt an endothelial fate (data not shown). Human outgrowth endothelial cells (OEC) used as control for cardiac endothelial gene profiling (FIG. 9a) were generated as described previously.

Detection of Luciferase+ Cells In Vivo Using the IVIS System. Vehicle (a mixture of RNAiMAX™ and opti-MEM™ basal medium) or luc MODRNA (100 ug/heart) was administrated into the left ventricle of hearts of wildtype Balb/c mice. Bioluminescence imaging of the injected mice was taken at different time points (3-240 hours). To visualize Luc+ cells, luciferin (150 lg/g body weight; Sigma™) was injected intraperitoneally (i.p.). After 10-20 minutes, mice were anesthetized with xylazine (20 mg/ml) and ketamine (100 mg/ml), and imaged using an IVIS100™ charge-coupled device imaging system for 2 minutes. Imaging data were analyzed and quantified with the Living Image Software™. The strength of the signal (representing the number of cells) is indicated by the spectrum of different colors. As expected, Luc+ cells could be observed in hearts injected with the luc MODRNA in a concentration and time-dependent manner (data not shown), whereas in hearts that were injected with the vehicle only didn't show any signal (data not shown).

Generation of Epicardial Trace Mice. Wt1 eGFPCre/+ mice have been described previously. Inducible Wt1CreERT2/+::R26 mTmG mice were generated by crossing the Wt-1CreERT2/+ strain with Rosa26 mTmG reporter mice and genotyping as previously shown. Adult mice were treated with intraperitoneal (i.p.) injection of 4 mg tamoxifen (Tam) twice weekly for 2-3 weeks to induce Cre. One week after completion of Tam dosing, myocardial infarction (MI) was induced by ligation of left anterior descending artery (LAD) coronary artery as described below. Hearts were subsequently assessed using a combination of FACS, immunofluorescence and real-time qPCR analyses for eGFP expression and myocardial markers after 7 days. With respect to monitoring cell fate switch of the epicardial progenitors, the focus was on the inducible Wt1CreERT2/+::R26 mTmG model to ensure specific temporal labeling of Wt1-eGFP+ derivatives. Mice that were vehicle treated with tamoxifen in the presence or absence of MI were used as controls and importantly eGFP+ cardiomyocyte-like cells were never observed in these hearts.

Induction of Myocardial Infarction. All surgical and experimental procedures with mice were performed in accordance with protocols approved by the Institutional Animal Care and Use Committees of Massachusetts General Hospital. MI was induced in isoflurane-anaesthetized wildtype C57B1/6, Rosa26-LacZ, Wt1eGFPCre/+ or Wt1CreERT2/+::R26 mTmG mice (6-8 week old) by permanent ligation of the LAD. In order to determine the effect of hVEGF-A MODRNA in cardiovascular regeneration, vehicle or hVEGF-A MODRNA (100 ug/heart) were injected into the infarct zone immediately after LAD ligation. Sham controls (pericardium was opened but LAD was not ligated) were also included per experiment. Hearts were harvested at 7 days after ligation. The infarct zone near the apex was either snap frozen for RNA isolation and subsequent real-time qPCR studies or was fixed in 4% PFA for cryosectioning and immunostaining analyses.

Wt1-eGFP+ Cell Isolation and Characterization. The apex of hearts collected from Wt1eGFPCre/+ or Wt1CreERT2/+::R26 mTmG mice treated with vehicle or hVEGF-A MODRNA post-MI, as described earlier, were harvested 7 days after LAD ligation and processed by enzymatic digestion using a collagenase II (Sigma™) to achieve a single-cell suspension. Viable eGFP+ cells were isolated from the total cardiac cell population using a FACSAria II™ cell sorter with a 488 nm laser beam used to excite eGFP (collected in the 520/30 nm channel) and a 536 nm laser beam used to excite PI (collected in the 610/620 nm channel). As a control, hearts from uninjured Wt1eGFPCre/+ or Wt1CreERT2/+::R26 mTmG mice treated either with vehicle or hVEGF-A MODRNA were also analyzed after 7 days. Cells were incubated with the APC-conjugated Flk-1 antibody (BD Biosciences™) at 4° C. for 30 minutes followed by 3 washes with PBS/2% FBS and resuspended in Hank's balanced salt solution. Cell sorting and flow cytometric analysis were performed using a FACSAria II™ cell sorter and the FlowJo™ Software. eGFP+ fibroblasts, cardiomyocytes, smooth muscle and endothelial cells were assessed by immunostaining and cell counts through serial sections as described below.

RNA Isolation and Gene Expression Profiling. Total RNA was isolated from the apex of collected hearts using the RNeasy™ mini kit (Qiagen™) and reversely transcribed using Superscript III™ RT (Invitrogen™), according to the manufacturer's instructions. Real-time qPCR analyses were performed on a Mastercycler realplex 4 Sequence Detector™ (Eppendorff™) using SYBR Green™ (Quantitect™ SYBR Green PCR Kit™, Qiagen™). Data were normalized to Gapdh and β-Actin expression, where appropriate (endogenous controls). Fold-changes in gene expression were determined by the 22DDCT method and are presented relative to vehicle-treated hearts. Complementary DNA PCR primer sequences are shown herein in Table 2. To characterize eGFP+ progenitors, total RNA was obtained from FACS-sorted eGFP+ cells isolated after collagenase digestion of the hVEGF-A MODRNA- or the vehicle-treated hearts derived from Wt1eGFPCre/+ or Wt1CreERT2/+::R26 mTmG mice at 7 days following LAD ligation using a FACSAria II™ cell sorter.

Immunodetection methods. Immunostaining was performed on murine neonatal and adult cardiac cell cultures, human fetal cardiac cell cultures and on cryosections of SHAM hearts, post-MI hearts treated with vehicle or hVEGF MODRNA using standard protocols with the following antibodies: cardiac cTnT (NeoMarkers™), cardiac MHC, vimentin (R&D Systems™), β-galactosidase, collagen I, cardiac cTNI, CD31, CD144, vWF, SMMHC, Wt1, and Ki67 (Abcam™) and Flk1 (BD Biosciences™) The specificity of the anti-eGFP antibody was ascertained by immunostaining on SHAM hearts with very few, if any, eGFP+ cells in the epicardial region (which might be the "leakiness" of the system). Immunostaining with isolectin B4 (Vector Lab™) was performed on cryosections to determine capillary density and TUNEL staining (Roche™) was performed to detect apoptosis, according to the manufacturer's instructions. To examine the degree of fibrosis, picrosirius red staining was employed on cryosections which binds specifically to collagen fibrils. Quantification of immunostaining images was performed by the ImageJ™ Software.

Magnetic Resonance Imaging (MRI). Wildtype C57B1/6, Rosa26-LacZ, Wt1 eGFPCre/+ or Wt1CreERT2/+::R26 mTmG mice (6-8 week old) were treated with vehicle or hVEGF-A MODRNA were subjected to MRI assessment at 1 and 21 days after LAD ligation. Where infarct size was within the range of 15-40%, follow-up MRI analyses were performed on the same mice at 21 days post-MI to determine temporal changes in infarct size and cardiac function. Mice were anaesthetized with 1-2% isofluorane/air mixture. EKG, respiratory, and temperature probes were placed on the mouse which was warmed on a heating pad. Images were acquired on a 4.7 T Bruker Biospec™. A stack of short-axis slices covering the heart from the apex to the base and an orthogonal long-axis slice was acquired with an ECG triggered and respiratory-gated Flash-CINE sequence with the following parameters: repetition time (TR) 25 msec, echo time (TE) 2.8 msec, 4 averages, slice thickness, 1 mm, matrix size 192×192 (2.56×2.56 cm), 5-7 frames per sequence (depending on RR interval). The resulting acquisition time per slice was approximately 5 min. Five short-axis slices were acquired from the apex to the base to cover the left ventricle. Left ventricular (LV) ejection fraction was calculated as the difference in diastolic and systolic LV volumes, divided by the diastolic LV volume. CINE-MRI acquisition and analyses were performed blinded to treatment group.

Statistical Analyses. Unless otherwise described, statistical significance was determined using Student's t-test with $P<0.05$ as significant. Values were reported as mean±standard error of the mean. In the box and whisker plot, boxes and bars indicate 25, 50, and 75 percentiles, and whiskers indicate extreme values.

Example 4

Preclinical testing of a cardiac regenerative therapeutic strategy, based on hVEGF-A modRNA, in rabbit. Experiments with rabbits can establish an intermediate animal model (rabbit) for ModRNA to facilitate preclinical testing. Experiments to optimize safety of ModRNA introduction and evaluate an alternate method for delivering ModRNA to the epicardial surface (hydrogel or other biopolymer that does not require injection into myocardium and therefore reduces risk of systemic introduction of ModRNA) can also be performed. Experiments can assess whether or not hVEGF-A ModRNA can be utilized to treat chronic, as well as acute, MI.

ModRNA-driven gene expression can be examined in native rabbit hearts, validating that the system functional in mouse is also functional in rabbit. The dose-response of LacZ ModRNA (100 ug, 500 ug, 1 mg) in rabbit heart can be determined using epicardial injection and compared to the LacZ ModRNA dose-response in rabbit heart when delivered via calcium alginate gel or other biopolymer at a 1:1 dose comparison with injection. For both delivery methods, visualize ModRNA-induced LacZ expression can be visualized using both superficial and cross-sectional views to assess area versus depth of expression with the two methods. For both delivery methods, a cross-sectional staining plan to co-stain beta galactosidase versus troponin, PECAM, vimentin, and smMHC can confirm that all cell types are transfected. Furthermore, a comparative assessment of peripheral hemangioma formation, for both ModRNA introduction methods, can be performed in order to assess safety vis-à-vis systemic introduction of the agent.

hVEGF-A ModRNA Injected in the Context of Acute MI in Rabbit. MI can be performed through ligation of mid-segment of anterior interventricular artery. Co-transfection of hVEGF-A and LacZ can be performed at the time MI is planned. Cells marked by durable LacZ expression can thus mark those cells into which VEGF ModRNA was injected (both injection and superficial gel application can be used). After MI, RT-PCR of treated cardiac tissue (for both injection and gel introduction of modRNA) for the following genes (as compared with thoracotomy/pericardiectomy with no MI control) can be performed: Wt1, Tbx18, NRx2.5, Isl1, TnT, PECAM, vimentin, smMHC, and Flk1. Myocardial cross-sectional staining can assess for co-localization of Wt1/LacZ/Ki67 as indirect fate mapping for epicardial Wt1 cells that differentiate and migrate from the epicardial surface into the myocardium. Myocardial cross-sectional staining can assess capillary density (PECAM), fibroblast density (vimentin), cardiomyocytes, and cell death (TUNEL). Short-axis cross-sectional view of treated and untreated hearts with trichrome stain can assess scar burden in treated (two application methods) versus untreated hearts. Cardiac MR imaging can also be performed in treated and untreated animals in order to assess effect of ModRNA treatment of contractile function of the heart after MI.

Determination of the Duration of Wt1" Cell Upregulation after Myocardial Infarction. Programmed myocardial infarctions can be created in genetically modified mice in which GFP is present in one of the alleles of the Wt1 locus. Animals infarcted can be sacrificed weekly out to 8 weeks to determine a time course for Wt1 cell activation (FACS). A second set of the same mouse strain can be infarcted with hVEGF-A ModRNA treatment as a series of intervals after MI (versus simultaneous with MI, as described previously). VEGF ModRNA treatment can be carried out in different animals in one-week intervals after MI, out to 8 weeks, or until an effect is no longer seen as assessed with immunohistochemical assessments of scar burden as described above herein. Left ventricular ejection fraction can also be assessed with cardiac magnetic resonance imaging. Negative controls, in which mod-RNA is not administered, can provide an assessment of how long the post-MI proliferation of Wt1-expressing cells persists, a parameter which is not currently known. These analyses can assess the extent to which the results observed at one week post-MI are durable, and whether any regression occurs. Without wishing to be limited by theory, multiple treatments might be necessary. In order to determine whether or not sub-acute or chronic infarct can be effectively treated with hVEGF-A mod-RNA, hVEGF-A mod-RNA can be administered after MI (from 1 to 8 weeks, in one-week increments). Magnitude of effect on Wt1+ cell stimulation and subsequent scar size can be assessed as described as described above herein. Once the window of therapeutic opportunity is defined in the mouse, the same experiments can be repeated in the rabbit.

Example 5

Enhancement of pancreatic adenocarcinoma drug treatment through local delivery of chemically modified mRNA for hVEGF-A and other factors involved in tumor growth.

The mortality rate associated with pancreatic ductal adenocarcinoma (PDAC) is 95% within 5 years of initial diagnosis. Cytotoxic chemotherapeutic agents, such as gemcitabine, are highly effective against adenocarcinoma cells in vitro, but exhibit limited effectiveness in the clinical setting. This suboptimal response is suspected to be secondary to the inability of such drugs to traverse the desmoplastic layer of stromal cells that surround adenocarcinoma cells in many tumors.[1, 2] The presence of this stromal mass, which is proliferated by the tumor and may comprise 80% of an individual tumor's mass, is correlated with poor clinical response to chemotherapy.[3] Alternate treatment strategies for advanced PDAC, notably use of VEGF inhibitors to reduce tumor blood supply, were also unsuccessful in the clinical setting.[4-7] Permeabilization and/or shrinking of this desmoplastic layer to enhance efficacy of cytotoxic chemotherapeutics may therefore represent a novel adjunct to treatment of pancreatic adenocarcinoma.[1, 2] Since VEGF inhibition was not successful, it may be that local delivery of VEGF, either alone or in combination with existing cytotoxic chemotherapeutics, represents a novel paradigm for inhibition of PDAC growth. Several other molecular targets may be utilized for reduction of PDAC desmoplasia, notably Hedgehog (Hh), which has been shown to be central to the proliferation of desmoplastic tissue associated with PDAC tumors.[8] Inhibition of Hh ligand-dependent signaling is a promising strategy for inhibiting growth of pancreatic ductal carcinoma.[1, 9] Several Hh ligands have been targeted, including Hg binding partners Smoothened (Smo) and Patched 1 (Ptc1).[8, 10] Downstream effectors, notably Gli, have also been targeted.[11, 12] Although mechanistically promising, the targeting of VEGF and Hh-related factors using systemically delivered agents is challenging due to concerns for untoward side effects.

The presence of a desmoplastic tissue surrounding PDAC tumors inhibits entry of chemotherapeutic agents and leads to the clinical failure of cytotoxic chemotherapeutics that target adenocarcinoma cells. Local delivery of chemically modified mRNA for VEGF-A into (and around) PDAC tumors can lead to neovascularization that may bypass this desmoplastic capsule and improve drug delivery to adenocarcinoma tissue, thus decreasing rate of response failure.[13] This local delivery strategy may help avoid the risk of metastatic dissemination associated with systemic VEGF expression. Local delivery of chemically modified RNA may also be helpful for inhibiting Hedgehog-related signaling, which has been shown to be involved in tumor growth and proliferation of this desmoplastic tissue.[8] Described herein are compositions and methods relating to the use of chemically modified antisense RNA for Hh ligands (such as Smo and Ptc1) and downstream effectors (such as Gli) to similarly alter the properties of PDAC desmoplastic tumor stroma and improve clinical response to treatment.[9-12]

Described herein is the establishment of an in vivo procedure for introducing chemically modified RNA into the pancreas to drive the local expression of proteins.° This protein expression system can be evaluated as an alternative to existing chemotherapeutics for PDAC.

Expression of luciferase in wild-type mouse pancreas by direct parenchymal injection of modified RNA. LacZ and Luciferase can be expressed in vivo in mouse pancreas using chemically modified RNA. This procedure can involve surgical exposure of the pancreas, with eversion and direct injection of modified RNA into tissue. Optimal dose to achieve expression can be evaluated.

In vivo expression of Luciferase in mouse pancreas can be accomplished according to the procedure described in the preceding paragraph. Dose can be informed by the LacZ experiment. The purpose of performing this experiment is to determine the time course of protein expression after injection. IVIS imaging can be used to track expression.

Expression of VEGF-A in wild-type mouse pancreas by direct parenchymal injection of modified RNA. Feasibility can be determined by in vivo injection of VEGF-A modified RNA. Dose can be determined by the results of the experiments described above in this Example. Protein expression can be measured within 48 hours of injection using immunohistochemistry.

In vivo injection of VEGF-A modified RNA can be analyzed to determine physiologic "readout" of protein expression. Vascularization of treated versus sham treated animals can be compared using gross inspection and basic H+E staining, performed 3 weeks after injection.

Expression of VEGF-A in pancreatic adenocarcinoma tumors in a mouse model for PDAC (LSL-KrasG12D; p53 L/+).[14], with assessment of tumor neovascularization and putative effect on gemcitabine levels within thus treated tumors. The impact of in vivo injection of VEGF-A into pancreatic tumors and surrounding tissue can be determined by tumor histology (neovascularization, size of tumor, size of desmoplastic capsule) assessed with histological analysis at several time points after injection (1, 2, and 3 weeks).

VEGF-A can be injected into pancreatic tumors and surrounding tissue. Gemcitabine can be administered at several time points (simultaneous, as well as 1, 2, and 3 weeks after modified RNA injection) in standard fashion. Impact on tumor histology (neovascularization, size of tumor, size of desmoplastic capsule) can be assessed with histological analysis at several time points after injection (1, 2, and 3 weeks). Direct assay of gemcitabine levels within treated versus untreated tumors will be performed to assess whether or not VEGF can increase drug levels within the tumors[1, 2] This series of experiments can determine the optimal timing between administration of VEGF-A and gemcitabine. These experiments can be repeated with chemically modified antisense RNA for Hh ligands Smo, Ptc1 as well as Hh downstream effector Gli. Using a mouse model for pancreatic adenocarcinoma, chemically modified antisense RNA for Smo, Ptc1, and Gli can be injected. Reduction in protein expression in the injected area can be confirmed with immunohistochemistry. Tissue blocks can also be assessed with Western blot. Once it is confirmed that chemically modified antisense RNA can reduce protein expression levels, testing of the effects of such reduction on tumors can be performed in the aforementioned model system, as described above herein.

REFERENCES

1. Neesse A, Michl P, Frese K, Feig C, Cook N, Jacobetz M, Lolkema M, Buchholz M, Olive K, Gress T, Tuveson D. Stromal biology and therapy in pancreatic cancer. *Gut.* 2011; 60:861-868.
2. Bapiro T, Richards F, Goldgraben M, Olive K, Madhu B, Frese K, Cook N, Jacobetz M, Smith D, Tuveson D, Griffiths J, Jodrell D. A novel method for quantification of gemcitabine and its metabolites 2',2'-difluorodeoxyuridine and gemcitabine triphosphate in tumour tissue by LC-MS/MS: comparison with (19)F NMR spectroscopy. *Cancer Chemother Pharmacol.* 2011; 68:1243-1253.
3. Erkan M, Reiser-Erkan C, Michalski C, Kong B, Esposito I, Friess H, Kleeff J. The Impact of the Activated Stroma on Pancreatic Ductal Adenocarcinoma Biology and Therapy Resistance. *Curr Mol Med.* 2012; Jan. 19 Epub ahead of print.
4. Albrecht I, Kopfstein L, Strittmatter K, Schomber T, Falkevall A, Hagberg C, Lorentz P, Jeltsch M A, K, Eriksson U, Christofori G, Pietras K. Suppressive effects of vascular endothelial growth factor-B on tumor growth in a mouse model of pancreatic neuroendocrine tumorigenesis. *PLoS One.* 2010; 5:e14109.
5. Olson P, Chu G, Perry S, Nolan-Stevaux O, Hanahan D. Imaging guided trials of the angiogenesis inhibitor sunitinib in mouse models predict efficacy in pancreatic neuroendocrine but not ductal carcinoma. *PNAS.* 2011; 108:E1275-E1284.
6. Ko A, Youssoufian H, Gurtler J, Dicke K, Kayaleh O, Lenz H, Keaton M, Katz T, Ballal S, Rowinsky E. A phase II randomized study of cetuximab and bevacizumab alone or in combination with gemcitabine as first-line therapy for metastatic pancreatic adenocarcinoma. *Invest New Drugs.* 2011; Epub ahead of print.
7. Kindler H, Ioka T, Richel D, Bennouna J, Létourneau R, Okusaka T, Funakoshi A, Furuse J, Park Y, Ohkawa S, Springett G, Wasan H, Trask P, Bycott P, Ricart A, Kim S, Van Cutsem E. Axitinib plus gemcitabine versus placebo plus gemcitabine in patients with advanced pancreatic adenocarcinoma: a double-blind randomised phase 3 study. *Lancet Oncol.* 2011; 12:256-262.
8. Kelleher F. Hedgehog signaling and therapeutics in pancreatic cancer. *Carcinogenesis.* 2011; 32:445-451.
9. Olive K, Jacobetz M, Davidson C, Gopinathan A, McIntyre D, Honess D, Madhu B, Goldgraben M, Caldwell M, Allard D, Frese K, Denicola G, Feig C, Combs C, Winter S, Ireland-Zecchini H R, S, Howat W, Chang A, Dhara M, Wang L, Rückert F, Grützmann R, Pilarsky C, Izeradjene K, Hingorani S, Huang P, Davies S, Plunkett W, Egorin M, Hruban R, Whitebread N, McGovern K, Adams J, Iacobuzio-Donahue C, Griffiths J, Tuveson D. Inhibition of Hedgehog signaling enhances delivery of chemotherapy in a mouse model of pancreatic cancer. *Science.* 2009; 324:1457-1461.
10. Nakamura M, Tanaka H, Nagayoshi Y, Nakashima H, Tsutsumi K, Ohtsuka T, Takahata S, Tanaka M, Okada H. Targeting the hedgehog signaling pathway with interacting peptides to Patched-1. *J. Gastroenterol.* 2011; Dec. 15 Epub ahead of print.
11. Hyman J, Firestone A, Heineb V, Zhaoc Y, Ocasio C, Han K, Sun M, Rack P, Sinha S, Wue J, Solow-Cordero D, Jiang J, Rowitch D, Chen J. Small-molecule inhibitors reveal multiple strategies for Hedgehog pathway blockade. *PNAS.* 2009; 106:14132-14137.
12. Jung I, Jung D, Park Y, Song S, Park S. Aberrant Hedgehog Ligands Induce Progressive Pancreatic Fibrosis by Paracrine Activation of Myofibroblasts and Ductular Cells in Transgenic Zebrafish. *PLoS One.* 2011; 6:e27941.
13. Warren L, Manos P, Ahfeldt T, Loh Y, Li H, Lau F, Ebina W, Mandal P, Smith Z, Meissner A, Daley G, Brack A, Collins J, Cowan C, Schlaeger T, Rossi D. Highly efficient reprogramming to pluripotency and directed differentiation of human cells with synthetic modified mRNA. *Cell Stem Cell.* 2010; 7:618-630.
14. Bardeesy N, Aguirre A, Chu G, Cheng K, Lopez L, Hezel A, Feng B, Brennan C, Weissleder R, Mahmood U, Hanahan D, Redston M, Chin L, Depinho R. Both p16 (Ink4a) and the p19(Arf)-p53 pathway constrain progression of pancreatic adenocarcinoma in the mouse. *PNAS.* 2006; 103:5947-5952.

TABLE 8

Source of Antibodies

| Name | Company |
| --- | --- |
| β-Galectosidase | Abcam |
| Cardiac Troponin T | NeoMarkers |
| Cardiac Troponin I | Abcam |
| Collagen type I | Abcam |
| cMHC | R&D systems |
| CD144 | Abcam |
| SMMHC | Abcam |
| Ki67 | Abcam |
| Isolectin B4 | Vector Lab |
| WT1 | Abcam |
| CD31 | Abcam, BD biosciences |
| Flk1 | BD Biosciences |
| vWF | Abcam |
| Vimentin | R&D systems |
| Tunel | Roche |
| Alexa-488 | Invitrogen |
| Alexa-594 | Invitrogen |
| Alexa-650 | Invitrogen |
| DAPI | Sigma |

TABLE 9

PCR primers

| Genes | Forward | SEQ ID NO | Reverse | SEQ ID NO |
| --- | --- | --- | --- | --- |
| hGapdh | TGTTGCCATCAATGACCCCTT | 0100 | CTCCACGACGTACTCAGCG | 0120 |
| hVegfa | AAGGAGGAGGGCAGAATCAT | 0101 | CCAGGCCCTCGTCATTG | 0121 |
| hVegfb | CCCAGCCTGATGCCCCTG | 0102 | TGCCCATGAGCTCCACAG | 0122 |
| hVegfc | AACAAACTCTTCCCCAGCCA | 0103 | TTTAACAAGCATTTCTGTGGAC | 0123 |
| hVegfd | GCAGGAGGAAAATCCACTTG | 0104 | GGGTGCTGGATTAGATCTTTG | 0124 |
| hPlgf | TGCAGCTCCTAAAGATCCGT | 0105 | GGGAACAGCATCGCCGCA | 0125 |
| mCd31 | CTGCCAGTCCGAAAATGGAAC | 0106 | CTTCATCCACCGGGGCTATC | 0126 |
| mcTnt | CTGAGACAGAGGAGGCCAAC | 0107 | TTCCGCTCTGTCTTCTGGAT | 0127 |
| mFlk1 | AGAACACCAAAGAGAGGAACG | 0108 | GCACACAGGCAGAAACCAGTAG | 0128 |
| mGapdh | TTGTCTCCTGCGACTTCAAC | 0109 | GTCATACCAGGAAATGAGCTTG | 0129 |
| mIsl1 | AGCACCAGCATCCTCTCTGT | 0110 | TGAAGCCTATGCTGCACTTG | 0130 |
| mInfa | ATGGCTAGRCTCTGTGCTTTCCT | 0111 | AGGGCTCTCCAGAYTTCTGCTCTG | 0131 |
| mInfb | AAGAGTTACACTGCCTTTGCCATC | 0112 | CACTGTCTGCTGGTGGAGTTCATC | 0132 |
| mRig1 | GGACGTGGCAAACAAATCAG | 0113 | GCAATGTCAATGCCTTCATCA | 0133 |
| mSmmhc | AAGCTGCGGCTAGAGGTCA | 0114 | CCCTCCCTTTGATGGCTGAG | 0134 |
| mNkx2.5 | CCAGTCTGGGTCCTAATGCGGGTGCGTCT | 0115 | GATAGGGCCTTTTTAAATAGCTCCGAGTTT | 0135 |
| mTbx18 | AACAGAATGGGTTTGGAAGC | 0116 | ACTTGTGTTGCCTTGCTTTG | 0136 |
| mVegfa | CTGTGCAGGCTGCTGTAACG | 0117 | GTTCCCGAAACCCTGAGGAG | 0137 |
| mVimentin | GACATTGAGATCGCCACCTA | 0118 | GGCAGAGAAATCCTGCTCTC | 0138 |
| mWt1 | AGACACACAGGTGTGAAACCA | 0119 | ATGAGTCCTGGTGTGGGTCT | 0139 |

REFERENCES

The references are each incorporated herein by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10086043B2). An electronic copy of the "Sequence Listing" will also be available from the USPTO upon request and payment of the fee set forth in 37 CFR 1.19(b)(3).

The invention claimed is:

1. A method for increasing capillary density in cardiac tissue in a subject by expressing a VEGF-A protein in a cardiac tissue in vivo, the method comprising contacting the cardiac tissue in vivo with a composition comprising a synthetic, modified RNA molecule encoding a VEGF-A polypeptide,
wherein the synthetic, modified RNA molecule comprises one or more modifications selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2, N2, 7-trimethylguanosine (m2,2,7G), and inosine (I),
such that introducing said synthetic, modified RNA molecule to a cell in the cardiac tissue in vivo results in increased capillary density in the cardiac tissue, and also results in a reduced innate immune response relative to a cell in the cardiac tissue in vivo contacted with a synthetic RNA molecule encoding the polypeptide not comprising said one or more modifications.

2. The method of claim 1, wherein the cardiac tissue is in a subject having a disease or disorder.

3. The method of claim 2, wherein the disease or disorder is selected from the group consisting of: acute coronary syndrome, congestive heart failure, cardiomyopathy, myocardial infarction, tissue ischemia, cardiac ischemia, vascular disease, acquired heart disease, atherosclerosis, dysfunctional conduction systems, pulmonary heart hypertension, structural heart disease, or disease or disorder characterized by insufficient cardiac function, coronary artery disease, myocardial ischemia, atherosclerosis, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis and congenital heart disease or a symptom of hypertension; blood flow disorders; symptomatic arrhythmia; pulmonary hypertension; dysfunction in conduction system; dysfunction in coronary arteries; dysfunction in coronary arterial tree and coronary artery colaterization.

4. The method of claim 1, wherein the cardiac tissue has a reduced capillary density and is in a subject with, or at risk of having heart failure.

5. The method of claim 1, wherein the VEGF-A protein is a VEGF-A$^{165}$ protein.

* * * * *